(12) United States Patent
Chang et al.

(10) Patent No.: US 10,450,573 B2
(45) Date of Patent: Oct. 22, 2019

(54) COMPOSITIONS AND METHODS FOR REGULATION OF GENE EXPRESSION WITH, AND DETECTION OF, FOLINIC ACID AND FOLATES

(71) Applicant: The Board of Trustees of the Leland Stanford Junior University, Stanford, CA (US)

(72) Inventors: Andrew L. Chang, Redwood City, CA (US); Christina D. Smolke, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 13 days.

(21) Appl. No.: 15/502,694

(22) PCT Filed: Aug. 13, 2015

(86) PCT No.: PCT/US2015/045120
§ 371 (c)(1),
(2) Date: Feb. 8, 2017

(87) PCT Pub. No.: WO2016/025750
PCT Pub. Date: Feb. 18, 2016

(65) Prior Publication Data
US 2018/0237781 A1 Aug. 23, 2018

Related U.S. Application Data

(60) Provisional application No. 62/037,015, filed on Aug. 13, 2014.

(51) Int. Cl.
*C12N 15/11* (2006.01)
*C12N 15/115* (2010.01)

(52) U.S. Cl.
CPC ........ *C12N 15/115* (2013.01); *C12N 2310/11* (2013.01); *C12N 2310/12* (2013.01);
(Continued)

(58) Field of Classification Search
CPC .............. C12N 15/115; C12N 2310/11; C12N 2310/12; C12N 2310/121; C12N 2310/16; C12N 2310/351; C12N 2310/3519
See application file for complete search history.

(56) References Cited

U.S. PATENT DOCUMENTS 7,960,102 B2   6/2011  Epstein et al.
2007/0077571 A1   4/2007  Ellington et al.
(Continued)

OTHER PUBLICATIONS

Yvonne Chen (Caltech PhD Thesis, Dec. 23, 2010, Genetic Control of T-Cell Proliferation with Synthetic RNA Regulatory Systems. Chapter 2 and Chapter 6, pp. 32-102 and pp. VI-1 through VI-59, respectively.*

(Continued)

*Primary Examiner* — Terra C Gibbs
(74) *Attorney, Agent, or Firm* — Pamela J. Sherwood; Bozicevic, Field & Francis LLP

(57) ABSTRACT

Aptamers that specifically bind to ligands of folinic acid, a folate, and derivatives thereof (which may be referred to herein as ligands) are provided, and compositions and methods of use thereof. The aptamers and switches of the invention provide biological sensing capability for detecting the ligands, and are effective in sensing in vitro and in vivo. By specific sensing of the ligand, the aptamers of the invention provide a means of engineering an inducible gene regulatory system that enables dose-dependent control over gene expression in response to the ligand, in vivo and in vitro.

13 Claims, 29 Drawing Sheets
(25 of 29 Drawing Sheet(s) Filed in Color)
Specification includes a Sequence Listing.

(52) U.S. Cl.
CPC .. *C12N 2310/121* (2013.01); *C12N 2310/122* (2013.01); *C12N 2310/14* (2013.01); *C12N 2310/141* (2013.01); *C12N 2310/16* (2013.01); *C12N 2310/20* (2017.05); *C12N 2310/351* (2013.01); *C12N 2310/3519* (2013.01); *C12N 2320/33* (2013.01)

(56) References Cited

U.S. PATENT DOCUMENTS

| | | |
|---|---|---|
| 2012/0263691 A1 | 10/2012 | Galloway et al. |
| 2014/0148503 A1 | 5/2014 | Giangrande et al. |

OTHER PUBLICATIONS

Trausch et al., "A Disconnect between High-Affinity Binding and Efficient Regulation by Antifolates and Purines in the Tetrahydrofolate Riboswitch," Chemistry & Biology, Jan. 2, 2014, pp. 205-216, vol. 21, Iss. 2, Cell Press, Cambridge, MA.

* cited by examiner

FAt8-4

FAt8-11

FAt8-3

FAt6-8

FAt8-16

FAt8-18

FAt10-7

FA8-14

FIG. 5A   FIG. 5B
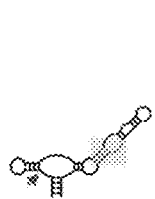
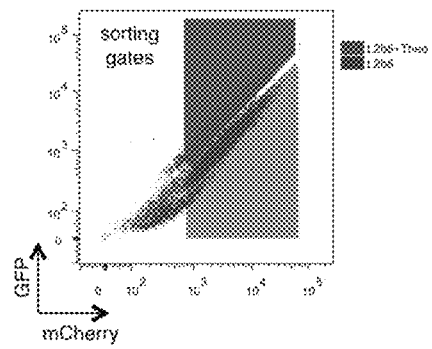
FIG. 5C
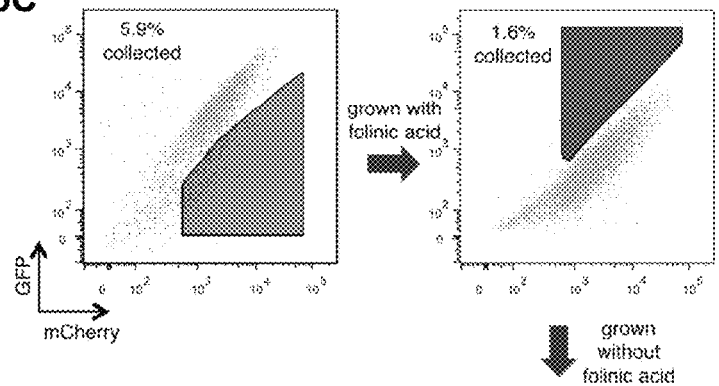
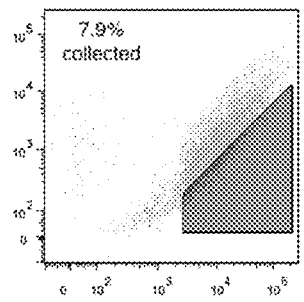 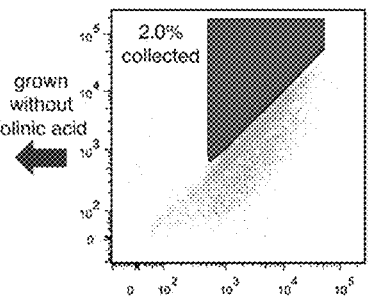 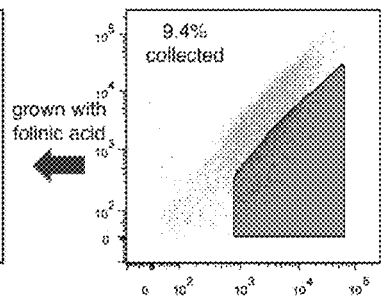

(6R)-FA-switch1

(6R)-FA-switch2

FIG. 8A
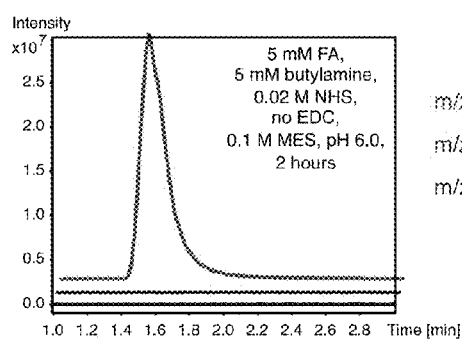
FIG. 8B
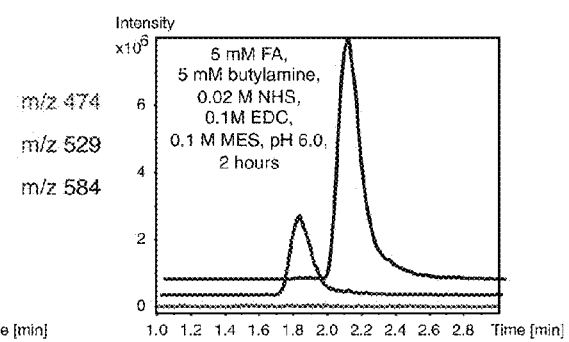
FIG. 8C
| Product | Extracted Ion Chromatogram (m/z) | Retention Time (min.) | 5 mM FA, 5 mM butylamine, 0.02 M NHS | 5 mM FA, 5 mM butylamine, 0.02 M NHS, 0.1 M EDC |
|---|---|---|---|---|
| unconjugated | 474 | 1.5 | 3.02E+08 | n.d. |
| single addition | 529 | 1.8 | n.d. | 2.09E+07 |
| double addition | 584 | 2.1 | n.d. | 7.13E+07 |

FIG. 10A
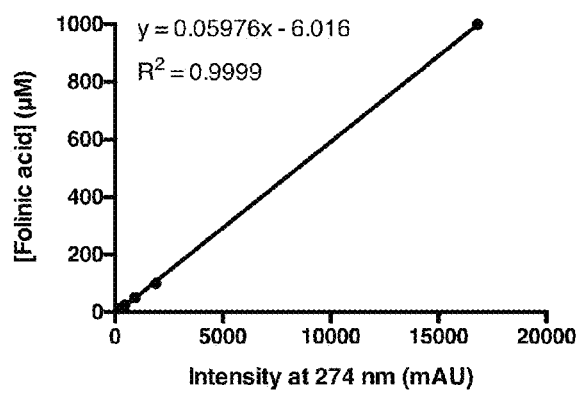
FIG. 10B
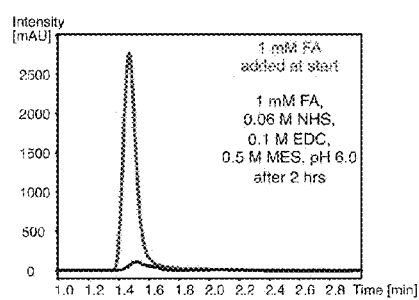
FIG. 10C
| Reaction time | RT (min.) | Intensity (mAU) | [Folinic acid] in reaction solution from standard curve (µM) | Percentage folinic acid reacted | [Folinic acid] conjugated onto beads (µM) |
|---|---|---|---|---|---|
| Added at start | 1.5 | 16822.00 | 999.94 | - | - |
| After 2 hrs | 1.5 | 1044.80 | 56.46 | 94.35% | 1886.96 |

FAt8-14

— 2 µM (6S)-FA
— 1 µM (6S)-FA
— 500 nM (6S)-FA
— 250 nM (6S)-FA
— 125 nM (6S)-FA

FAt8-4-stem1

A→C
C→A
G→U
U→G

FAt8-4-stem2

FAt8-4-stem3

FAt8-4-stem4

— 5 µM (6R,S)-FA
— 500 nM (6R,S)-FA
— 50 nM (6R,S)-FA

FA8-4  FA8-11

FA8-3  FA10-7

6bpL1FA8-11/4bpL2N6 (ANAGRG)
from 6bpL1FA8-11/4bpL2N6 library

6bpL1FA8-11/5bpL2N3 (NRR)
from 6bpL1FA8-11/3bpL2N7 library

|  | sTRSV | FA-58 | FA-7 | FA-19 |
|---|---|---|---|---|
| A.R. in (6S)-FA: | 1.0 | 1.2 | 2 | |
| A.R. in (6R)-FA: | 1.0 | 25.2 | 17.3 | 15.3 |

|  | FA-27 | FA-4 | FA-6 | FA-11 | FA-14 | FA-18 | FA-34 |
|---|---|---|---|---|---|---|---|
| A.R. in (6S)-FA: | 1.0 | | | | | | |
| A.R. in (6R)-FA: | 25.2 | 7.6 | 13.1 | 18.4 | 18.2 | 9.2 | 9.2 |

6bpL1FA8-4/4bpL2N4-5 (ARA(R)G)
from 6bpL1FA8-4/3bpL2N6 and
6bpL1FA8-4/3bpL2N7 libraries 6bpL1N7 (GGUGUAG)/4bpL2FA8-4
from 6bpL1N7/4bpL2FA8-4 library

|  | FA-9 | FA-32 | FA-12 | FA-22 |
|---|---|---|---|---|
| A.R. in (6S)-FA: | 1.0 | 1.0 | 0.9 | 1.0 |
| A.R. in (6R)-FA: | 6.8 | 11.8 | 9.0 | 5.4 |

```
                            SEQUENCE LISTING

<160> NUMBER OF SEQ ID NOS: 134

<210> SEQ ID NO 1
<211> LENGTH: 134
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (22)..(91)
<223> OTHER INFORMATION: n is a, c, g, or t

<400> SEQUENCE: 1
gtgtccgcct atctcgtctc cnnnnnnnnn nnnnnnnnnn nnnnnnnnnn nnnnnnnnnn    60
nnnnnnnnnn nnnnnnnnnn nnnnnnnnnn nggaaggagg cgggcagaag tccctatagt   120
gagtcgtatt agaa                                                     134

<210> SEQ ID NO 2
<211> LENGTH: 114
<212> TYPE: RNA
<213> ORGANISM: Artificial sequence
<220> FEATURE:
<223> OTHER INFORMATION: Synthetic nucleic acid

<400> SEQUENCE: 2
gggacuucug cccgccuccu uccugcucgu gucaaaauga auggcgcucg gcguugcgug    60
guacguuaua uuccggccaa gcagccauuc augggagacg agauaggcgg acac         114

<210> SEQ ID NO 3
<211> LENGTH: 115
<212> TYPE: RNA
<213> ORGANISM: Artificial sequence
<220> FEATURE:
<223> OTHER INFORMATION: Synthetic nucleic acid

<400> SEQUENCE: 3
gggacuucug cccgccuccu uccgcugagg acucggcacc gaauuugcca acgucugguc    60
acgaccguag uacacuaccc cucgaaauca cgagggagac gagauaggcg gacac        115

<210> SEQ ID NO 4
<211> LENGTH: 114
<212> TYPE: RNA
<213> ORGANISM: Artificial sequence
<220> FEATURE:
<223> OTHER INFORMATION: Synthetic nucleic acid

<400> SEQUENCE: 4
gggacuucug cccgccuccu uccgcuuacc ggacgccuua aggcaucagc augcagugcu    60
ugguacguua uauucagcug caaucgggga ugcggagacg agauaggcgg acac         114

<210> SEQ ID NO 5
<211> LENGTH: 113
<212> TYPE: RNA
<213> ORGANISM: Artificial sequence
<220> FEATURE:
<223> OTHER INFORMATION: Synthetic nucleic acid
```

```
<400> SEQUENCE: 5
gggacuucug cccgccuccu uccgcuauaa gucggacuuc ccgucaggua cguuauauuc      60
gggggaguac gguuaaagca gauuuguuga auggagacga gauaggcgga cac            113

<210> SEQ ID NO 6
<211> LENGTH: 73
<212> TYPE: RNA
<213> ORGANISM: Artificial sequence
<220> FEATURE:
<223> OTHER INFORMATION: Synthetic nucleic acid

<400> SEQUENCE: 6
gggacuucug cccgccuccu uccggugacc uggacguuau uuccggccga agggagacga      60
gauaggcgga cac                                                        73

<210> SEQ ID NO 7
<211> LENGTH: 113
<212> TYPE: RNA
<213> ORGANISM: Artificial sequence
<220> FEATURE:
<223> OTHER INFORMATION: Synthetic nucleic acid

<400> SEQUENCE: 7
gggacuucug cccgccuccu uccuacuccc gacucgucaa ugcauaugua acguuacgg       60 cgcuaccugu acaaugcacg uuccgagcgc cggagacga gauaggcgga cac             113

<210> SEQ ID NO 8
<211> LENGTH: 114
<212> TYPE: RNA
<213> ORGANISM: Artificial sequence
<220> FEATURE:
<223> OTHER INFORMATION: Synthetic nucleic acid

<400> SEQUENCE: 8
gggacuucug cccgccuccu uccccgacac ggcgaagagu caaagcaucc ccugcaugga     60
gccaacaagc ccugccucca cgcagggccc gugggagacg agauaggcgg acac           114

<210> SEQ ID NO 9
<211> LENGTH: 114
<212> TYPE: RNA
<213> ORGANISM: Artificial sequence
<220> FEATURE:
<223> OTHER INFORMATION: Synthetic nucleic acid

<400> SEQUENCE: 9
gggacuucug cccgccuccu uccgcgcaag ugcauuaacg gugacaccga aagcuggaaa     60
gccugacauc gaacgcaaaa ggcugcgugg cauggagacg agauaggcgg acac           114

<210> SEQ ID NO 10
<211> LENGTH: 88
<212> TYPE: DNA
<213> ORGANISM: Artificial sequence
<220> FEATURE:
<223> OTHER INFORMATION: Synthetic nucleic acid

<400> SEQUENCE: 10
ttctaatacg actcactata ggggcttggc gttgcgtggt acgttatatt ccggccaagc    60
ccccaaaaaa aaaaaaaaaa aaaaaaaa                                        88

<210> SEQ ID NO 11
```

<211> LENGTH: 120
<212> TYPE: DNA
<213> ORGANISM: Artificial sequence
<220> FEATURE:
<223> OTHER INFORMATION: Synthetic nucleic acid

<400> SEQUENCE: 11
ttctaatacg actcactata gggtttgcca acgtctggtc acgaccgtag tacactaccc     60
ctcgaaatca cgagggagac gagataggcg gaccccaaaa aaaaaaaaaa aaaaaaaaaa    120

<210> SEQ ID NO 12
<211> LENGTH: 82
<212> TYPE: DNA
<213> ORGANISM: Artificial sequence
<220> FEATURE:
<223> OTHER INFORMATION: Synthetic nucleic acid

<400> SEQUENCE: 12
ttctaatacg actcactata gggtgcagtg cttggtacgt tatattcagc tgcaccccaa     60
aaaaaaaaaa aaaaaaaaaa aa                                              82

<210> SEQ ID NO 13
<211> LENGTH: 80
<212> TYPE: DNA
<213> ORGANISM: Artificial sequence
<220> FEATURE:
<223> OTHER INFORMATION: Synthetic nucleic acid

<400> SEQUENCE: 13
ttctaatacg actcactata gggttcccgt caggtacgtt atattcgggg gaccccaaaa     60
aaaaaaaaaa aaaaaaaaaa                                                 80

<210> SEQ ID NO 14
<211> LENGTH: 92
<212> TYPE: DNA
<213> ORGANISM: Artificial sequence
<220> FEATURE:
<223> OTHER INFORMATION: Synthetic nucleic acid

<400> SEQUENCE: 14
ttctaatacg actcactata gggctccttc cggtgacctg gacgttattt ccggccgaag     60
ggagccccaa aaaaaaaaaa aaaaaaaaaa aa                                   92

<210> SEQ ID NO 15
<211> LENGTH: 120
<212> TYPE: DNA
<213> ORGANISM: Artificial sequence
<220> FEATURE:
<223> OTHER INFORMATION: Synthetic nucleic acid

<400> SEQUENCE: 15
ttctaatacg actcactata gggctcgtca atgcatatgt aacgttaacg gcgctacctg     60
tacaatgcac gttccgagcg cccggagacg agccccaaaa aaaaaaaaaa aaaaaaaaaa    120

<210> SEQ ID NO 16
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 16
ttctaatacg actcactata gggacggcga agagtcaaag catcccctgc gaaagcaggg     60
cccgtcccca aaaaaaaaaa aaaaaaaaaa aaa                                    93

<210> SEQ ID NO 17
<211> LENGTH: 120
<212> TYPE: DNA
<213> ORGANISM: Artificial sequence
<220> FEATURE:
<223> OTHER INFORMATION: Synthetic nucleic acid

<400> SEQUENCE: 17
ttctaatacg actcactata gggccgcgca agtgcattaa cggtgacacc gaaagctgga      60
aagcctgaca tcgaacgcaa aaggctgcgt ggccccaaaa aaaaaaaaaa aaaaaaaaaa     120

<210> SEQ ID NO 18
<211> LENGTH: 37
<212> TYPE: RNA
<213> ORGANISM: Artificial sequence
<220> FEATURE:
<223> OTHER INFORMATION: Synthetic nucleic acid

<400> SEQUENCE: 18
gcuuggcguu gcgugguacg uuauauuccg gccaagc                                37

<210> SEQ ID NO 19
<211> LENGTH: 69
<212> TYPE: RNA
<213> ORGANISM: Artificial sequence
<220> FEATURE:
<223> OTHER INFORMATION: Synthetic nucleic acid

<400> SEQUENCE: 19
uuugccaacg ucuggucacg accguaguac acuaccccuc gaaaucacga gggagacgag      60
auaggcgga                                                              69

<210> SEQ ID NO 20
<211> LENGTH: 31
<212> TYPE: RNA
<213> ORGANISM: Artificial sequence
<220> FEATURE:
<223> OTHER INFORMATION: Synthetic nucleic acid

<400> SEQUENCE: 20
ugcagugcuu gguacguuau auucagcugc a                                     31

<210> SEQ ID NO 21
<211> LENGTH: 29
<212> TYPE: RNA
<213> ORGANISM: Artificial sequence
<220> FEATURE:
<223> OTHER INFORMATION: Synthetic nucleic acid

<400> SEQUENCE: 21
uucccgucag guacguuaua uucggggga                                        29

<210> SEQ ID NO 22
<211> LENGTH: 41
<212> TYPE: RNA
<213> ORGANISM: Artificial sequence
<220> FEATURE:
<223> OTHER INFORMATION: Synthetic nucleic acid

<400> SEQUENCE: 22
cuccuuccgg ugaccuggac guuauuuccg gccgaaggga g                          41

```
<210> SEQ ID NO 23
<211> LENGTH: 69
<212> TYPE: RNA
<213> ORGANISM: Artificial sequence
<220> FEATURE:
<223> OTHER INFORMATION: Synthetic nucleic acid

<400> SEQUENCE: 23
cucgucaaug cauauguaac guuaacggcg cuaccuguac aaugcacguu ccgagcgccc    60
ggagacgag                                                           69

<210> SEQ ID NO 24
<211> LENGTH: 42
<212> TYPE: RNA
<213> ORGANISM: Artificial sequence
<220> FEATURE:
<223> OTHER INFORMATION: Synthetic nucleic acid

<400> SEQUENCE: 24
acggcgaaga gucaaagcau ccccugcgaa agcagggccc gu                      42

<210> SEQ ID NO 25
<211> LENGTH: 69
<212> TYPE: RNA
<213> ORGANISM: Artificial sequence
<220> FEATURE:
<223> OTHER INFORMATION: Synthetic nucleic acid

<400> SEQUENCE: 25
ccgcgcaagu gcauuaacgg ugacaccgaa agcuggaaag ccugacaucg aacgcaaaag    60
gcugcgugg                                                           69

<210> SEQ ID NO 26
<211> LENGTH: 88
<212> TYPE: DNA
<213> ORGANISM: Artificial sequence
<220> FEATURE:
<223> OTHER INFORMATION: Synthetic nucleic acid

<400> SEQUENCE: 26
ttctaatacg actcactata gggtaggttc gttgcgtggt acgttatatt ccggaaccta    60
ccccaaaaaa aaaaaaaaaa aaaaaaaa                                      88

<210> SEQ ID NO 27
<211> LENGTH: 88
<212> TYPE: DNA
<213> ORGANISM: Artificial sequence
<220> FEATURE:
<223> OTHER INFORMATION: Synthetic nucleic acid

<400> SEQUENCE: 27
ttctaatacg actcactata gggtaggtta gttgcgtggt acgttatatt ccgtaaccta    60
ccccaaaaaa aaaaaaaaaa aaaaaaaa                                      88

<210> SEQ ID NO 28
<211> LENGTH: 102
<212> TYPE: DNA
<213> ORGANISM: Artificial sequence
<220> FEATURE:
<223> OTHER INFORMATION: Synthetic nucleic acid

<400> SEQUENCE: 28
ttctaatacg actcactata ggggcttggc gttgcgtgca gtgagcctac tggtacgtta    60
```
tattccggcc aagcccccaa aaaaaaaaaa aaaaaaaaaa aa                   102

<210> SEQ ID NO 29
<211> LENGTH: 102
<212> TYPE: DNA
<213> ORGANISM: Artificial sequence
<220> FEATURE:
<223> OTHER INFORMATION: Synthetic nucleic acid

<400> SEQUENCE: 29
ttctaatacg actcactata ggggcttggc gttgcgtggc agtgagccta ctgtacgtta   60
tattccggcc aagcccccaa aaaaaaaaaa aaaaaaaaaa aa                   102

<210> SEQ ID NO 30
<211> LENGTH: 43
<212> TYPE: DNA
<213> ORGANISM: Artificial sequence
<220> FEATURE:
<223> OTHER INFORMATION: Synthetic nucleic acid

<400> SEQUENCE: 30
ttctaatacg actcactata gggacttctg cccgcctcct tcc                  43

<210> SEQ ID NO 31
<211> LENGTH: 38
<212> TYPE: DNA
<213> ORGANISM: Artificial sequence
<220> FEATURE:
<223> OTHER INFORMATION: Synthetic nucleic acid

<400> SEQUENCE: 31
ttctaatacg actcactata gggacttctg cccgcctc                        38

<210> SEQ ID NO 32
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 32
gtgtccgcct atctcgtctc c                                          21

<210> SEQ ID NO 33
<211> LENGTH: 55
<212> TYPE: DNA
<213> ORGANISM: Artificial sequence
<220> FEATURE:
<223> OTHER INFORMATION: Synthetic nucleic acid

<400> SEQUENCE: 33
tccatggtat ggatgaattg tacaaataaa gcctaggggg acttctgccc gcctc      55

<210> SEQ ID NO 34
<211> LENGTH: 61
<212> TYPE: DNA
<213> ORGANISM: Artificial sequence
<220> FEATURE:
<223> OTHER INFORMATION: Synthetic nucleic acid

<400> SEQUENCE: 34
aagaaattcg cttatttaga agtggcgcgc cctctcgaga gtgtccgcct atctcgtctc   60
c                                                                61

```
<210> SEQ ID NO 35
<211> LENGTH: 49
<212> TYPE: DNA
<213> ORGANISM: Artificial sequence
<220> FEATURE:
<223> OTHER INFORMATION: Synthetic nucleic acid

<400> SEQUENCE: 35
tttttttttt tttttttttt ttttgggggt gtccgcctat ctcgtctcc          49

<210> SEQ ID NO 36
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 36
ttctaatacg actcactata ggg                                      23

<210> SEQ ID NO 37
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 37
tttttttttt tttttttttt ttttgggg                                 28

<210> SEQ ID NO 38
<211> LENGTH: 118
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (51)..(53)
<223> OTHER INFORMATION: n is a, c, g, or t
<220> FEATURE:
<221> NAME/KEY: misc_feature
<222> LOCATION: (79)..(86)
<223> OTHER INFORMATION: n is a, c, g, or t

<400> SEQUENCE: 38
aaacaaacaa agctgtcacc ggatgtgctt tccggtctga tgagtccgtt nnncgttgcg    60
tggtacgtta tattccggnn nnnnnnggag gacgaaacag caaaaagaaa aataaaaa    118

<210> SEQ ID NO 39
<211> LENGTH: 118
<212> TYPE: DNA
<213> ORGANISM: Artificial sequence
<220> FEATURE:
<223> OTHER INFORMATION: Synthetic nucleic acid

<400> SEQUENCE: 39
aaacaaacaa agctgtcacc ggatgtgctt tccggtctga tgagtccgtt ggtcgttgcg    60
tggtacgtta tattccgggc cgaacgggag gacgaaacag caaaaagaaa aataaaaa    118

<210> SEQ ID NO 40
<211> LENGTH: 117
<212> TYPE: DNA
<213> ORGANISM: Artificial sequence
<220> FEATURE:
<223> OTHER INFORMATION: Synthetic nucleic acid
```

<400> SEQUENCE: 40
aaacaaacaa agctgtcacc ggatgtgctt tccggtctga tgagtccgtt gctcgttgcg        60
tggtacgtta tattccgggg cgaacggagg acgaaacagc aaaaagaaaa ataaaaa          117

<210> SEQ ID NO 41
<211> LENGTH: 80
<212> TYPE: DNA
<213> ORGANISM: Artificial sequence
<220> FEATURE:
<223> OTHER INFORMATION: Synthetic nucleic acid

<400> SEQUENCE: 41
aaacaaacaa agctgtcacc ggatgtgctt tccggtctga tgagtccgtg aggacgaaac        60
agcaaaaaga aaaataaaaa                                                    80

<210> SEQ ID NO 42
<211> LENGTH: 80
<212> TYPE: DNA
<213> ORGANISM: Artificial sequence
<220> FEATURE:
<223> OTHER INFORMATION: Synthetic nucleic acid

<400> SEQUENCE: 42
aaacaaacaa agctgtcacc ggatgtgctt tccggtacgt gaggtccgtg aggacagaac        60
agcaaaaaga aaaataaaaa                                                    80

<210> SEQ ID NO 43
<211> LENGTH: 125
<212> TYPE: DNA
<213> ORGANISM: Artificial sequence
<220> FEATURE:
<223> OTHER INFORMATION: Synthetic nucleic acid

<400> SEQUENCE: 43
aaacaaacaa agctgtcacc ggatgtgctt tccggtctga tgagtccgtt gtccatacca        60
gcatcgtctt gatgcccttg gcagggacgg gacggaggac gaaacagcaa aagaaaaat       120 aaaaa                                                                   125

<210> SEQ ID NO 44
<211> LENGTH: 55
<212> TYPE: DNA
<213> ORGANISM: Artificial sequence
<220> FEATURE:
<223> OTHER INFORMATION: Synthetic nucleic acid

<400> SEQUENCE: 44
tccatggtat ggatgaattg tacaaataaa gcctagggggg acttctgccc gcctc            55

<210> SEQ ID NO 45
<211> LENGTH: 61
<212> TYPE: DNA
<213> ORGANISM: Artificial sequence
<220> FEATURE:
<223> OTHER INFORMATION: Synthetic nucleic acid

<400> SEQUENCE: 45
aagaaattcg cttatttaga agtggcgcgc cctctcgaga gtgtccgcct atctcgtctc        60
c                                                                        61

<210> SEQ ID NO 46

<211> LENGTH: 57
<212> TYPE: DNA
<213> ORGANISM: Artificial sequence
<220> FEATURE:
<223> OTHER INFORMATION: Synthetic nucleic acid

<400> SEQUENCE: 46
tccatggtat ggatgaattg tacaaataaa gcctaggaaa caaacaaagc tgtcacc    57

<210> SEQ ID NO 47
<211> LENGTH: 65
<212> TYPE: DNA
<213> ORGANISM: Artificial sequence
<220> FEATURE:
<223> OTHER INFORMATION: Synthetic nucleic acid

<400> SEQUENCE: 47
aagaaattcg cttatttaga agtggcgcgc cctctcgagt ttttattttt cttttgctg    60 tttcg    65

<210> SEQ ID NO 48
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 48
gacctaggaa acaaacaaag ctgtcacc    28

<210> SEQ ID NO 49
<211> LENGTH: 34
<212> TYPE: DNA
<213> ORGANISM: Artificial sequence
<220> FEATURE:
<223> OTHER INFORMATION: Synthetic nucleic acid

<400> SEQUENCE: 49
ggctcgagtt tttattttc tttttgctgt ttcg    34

<210> SEQ ID NO 50
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 50
ggtcacaaat tggaatacaa ctataactct    30

<210> SEQ ID NO 51
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 51
cggaattaac cctcactaaa ggg    23

<210> SEQ ID NO 52
<211> LENGTH: 122
<212> TYPE: DNA
<213> ORGANISM: Artificial sequence
<220> FEATURE:
<223> OTHER INFORMATION: Synthetic nucleic acid

<400> SEQUENCE: 52
aaacaaacaa agctgtcacc ggatgtgctt tccggtctga tgagtccgtt gctggcgttg      60
cgtggtacgt tatattccgg ccagttcagc ggaggacgaa acagcaaaaa gaaaaataaa    120
aa                                                                   122

<210> SEQ ID NO 53
<211> LENGTH: 142
<212> TYPE: DNA
<213> ORGANISM: Artificial sequence
<220> FEATURE:
<223> OTHER INFORMATION: Synthetic nucleic acid

<400> SEQUENCE: 53
aaacaaacaa atttgccaac gtctggtcac gaccgctgtc accggatgtg ctttccggtc      60
tgatgagtcc gtgaggacga acagcacag cccctcgaaa tcacgaggga gacgagatag    120
gcggaaaaaa gaaaaataaa aa                                             142

<210> SEQ ID NO 54
<211> LENGTH: 154
<212> TYPE: DNA
<213> ORGANISM: Artificial sequence
<220> FEATURE:
<223> OTHER INFORMATION: Synthetic nucleic acid

<400> SEQUENCE: 54
aaacaaacaa agctgtcacc ggatgtgctt tccggtctga tgagtccgtt gtcccaacgt      60
ctggtcacga ccgtagtaca ctacccctcg aaatcacgag ggagacgaga tagggacggg    120
acggaggacg aaacagcaaa agaaaaata aaaa                                 154

<210> SEQ ID NO 55
<211> LENGTH: 154
<212> TYPE: DNA
<213> ORGANISM: Artificial sequence
<220> FEATURE:
<223> OTHER INFORMATION: Synthetic nucleic acid

<400> SEQUENCE: 55
aaacaaacaa agctgtcacc ggatgtgctt tccggtctga tgagtccgtt gagtcaacgt      60
ctggtcacga ccgtagtaca ctacccctcg aaatcacgag ggagacgaga tagactgatt    120
acggaggacg aaacagcaaa agaaaaata aaaa                                 154

<210> SEQ ID NO 56
<211> LENGTH: 154
<212> TYPE: DNA
<213> ORGANISM: Artificial sequence
<220> FEATURE:
<223> OTHER INFORMATION: Synthetic nucleic acid

<400> SEQUENCE: 56
aaacaaacaa agctgtcacc ggatgtgctt tccggtctga tgagtccgtt gctgcaacgt      60
ctggtcacga ccgtagtaca ctacccctcg aaatcacgag ggagacgaga tagcagttca    120
gcggaggacg aaacagcaaa agaaaaata aaaa                                 154

<210> SEQ ID NO 57
<211> LENGTH: 210
<212> TYPE: DNA
<213> ORGANISM: Artificial sequence
<220> FEATURE:

<223> OTHER INFORMATION: Synthetic nucleic acid

<400> SEQUENCE: 57

```
aataaccggt gcgatcgcga acgggtcctc actacccctc gaaatcacga gggagacgag    60
ataagagcga cggcggagcg agcacaagct ggagtacaac tatagtgaag ccacagatgt   120
atagttgtac tccagcttgt gcccgccttg ccaaccataa cgtctggtca cgaccgtagt   180
aagggcccgt ttttaattaa atcgattatt                                    210
```

<210> SEQ ID NO 58
<211> LENGTH: 110
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (30)..(35)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 58

```
cctaggaaac aaacaaagct gtcaccggan nnnntccgg tctgatgagt ccgntgcgtg    60
gtacgttata ttccgggacg aaacagcaaa agaaaaata aaaactcgag              110
```

<210> SEQ ID NO 59
<211> LENGTH: 111
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (30)..(36)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 59

```
cctaggaaac aaacaaagct gtcaccggan nnnnntccg gtctgatgag tccgntgcgt    60
ggtacgttat attccgggac gaaacagcaa aagaaaaat aaaaactcga g            111
```

<210> SEQ ID NO 60
<211> LENGTH: 108
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (69)..(74)
<223> OTHER INFORMATION: n is a, c, g, or t

<400> SEQUENCE: 60

```
cctaggaaac aaacaaagct gtcaccggag ntgcgtggta cgttatattc cgtccggtct    60
gatgagtcnn nnngacgaa acagcaaaaa gaaaataaa aactcgag                 108
```

-continued

```
<210> SEQ ID NO 61
<211> LENGTH: 109
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (69)..(75)
<223> OTHER INFORMATION: n is a, c, g, or t

<400> SEQUENCE: 61
cctaggaaac aaacaaagct gtcaccggag ntgcgtggta cgttatattc cgtccggtct      60
gatgagtcnn nnnngacga aacagcaaaa agaaaaataa aaactcgag                 109

<210> SEQ ID NO 62
<211> LENGTH: 110
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (70)..(75)
<223> OTHER INFORMATION: n is a, c, g, or t

<400> SEQUENCE: 62
cctaggaaac aaacaaagct gtcaccggag ntgcgtggta cgttatattc cgtccggtct      60
gatgagtccn nnnnnggacg aaacagcaaa aagaaaaata aaaactcgag               110

<210> SEQ ID NO 63
<211> LENGTH: 106
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (30)..(35)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 63
cctaggaaac aaacaaagct gtcaccggan nnnnntccgg tctgatgagt ctgcntggta      60
cgttatattc rggacgaaac agcaaaaaga aaataaaaa ctcgag                    106

<210> SEQ ID NO 64
<211> LENGTH: 107
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (30)..(36)
<223> OTHER INFORMATION: n is a, c, g, or t
<220> FEATURE:
<221> NAME/KEY: misc_feature
<222> LOCATION: (56)..(56)
```

<223> OTHER INFORMATION: n is a, c, g, or t

<400> SEQUENCE: 64
cctaggaaac aaacaaagct gtcaccggan nnnnnntccg gtctgatgag tctgcntggt    60
acgttatatt crggacgaaa cagcaaaaag aaaaataaaa actcgag                  107

<210> SEQ ID NO 65
<211> LENGTH: 104
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (65)..(70)
<223> OTHER INFORMATION: n is a, c, g, or t

<400> SEQUENCE: 65
cctaggaaac aaacaaagct gtcaccggtg cntggtacgt tatattcrgc cggtctgatg    60
agtcnnnnnn gacgaaacag caaaagaaa ataaaaact cgag                       104

<210> SEQ ID NO 66
<211> LENGTH: 105
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (65)..(71)
<223> OTHER INFORMATION: n is a, c, g, or t

<400> SEQUENCE: 66
cctaggaaac aaacaaagct gtcaccggtg cntggtacgt tatattcrgc cggtctgatg    60
agtcnnnnnn ngacgaaaca gcaaaagaaa aataaaaac tcgag                     105

<210> SEQ ID NO 67
<211> LENGTH: 106
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (66)..(71)
<223> OTHER INFORMATION: n is a, c, g, or t

<400> SEQUENCE: 67
cctaggaaac aaacaaagct gtcaccggtg cntggtacgt tatattcrgc cggtctgatg    60
agtccnnnnn nggacgaaac agcaaaaaga aaaataaaaa ctcgag                   106

<210> SEQ ID NO 68
<211> LENGTH: 107
<212> TYPE: DNA
<213> ORGANISM: Artificial sequence

```
<220> FEATURE:
<223> OTHER INFORMATION: Synthetic nucleic acid
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (67)..(73)
<223> OTHER INFORMATION: n is a, c, g, or t

<400> SEQUENCE: 68
cctaggaaac aaacaaagct gtcaccgggn tgcgtggtac gttatattcc gccggtctga      60
tgagtcnnnn nnngacgaaa cagcaaaaag aaaaataaaa actcgag                  107

<210> SEQ ID NO 69
<211> LENGTH: 107
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (27)..(33)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 69
cctaggaaac aaacaaagct gtcaccnnnn nnnggtctga tgagtcccgn tgcgtggtac      60
gttatattcc ggggacgaaa cagcaaaaag aaaaataaaa actcgag                  107

<210> SEQ ID NO 70
<211> LENGTH: 103
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (63)..(69)
<223> OTHER INFORMATION: n is a, c, g, or t

<400> SEQUENCE: 70
cctaggaaac aaacaaagct gtcaccgtgc ntggtacgtt atattcrgcg gtctgatgag      60
tcnnnnnnng acgaaacagc aaaagaaaa ataaaaactc gag                       103

<210> SEQ ID NO 71
<211> LENGTH: 103
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (27)..(33)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 71
```

```
cctaggaaac aaacaaagct gtcaccnnnn nnnggtctga tgagtcctgc ntggtacgtt      60
atattcrggg acgaaacagc aaaagaaaaa ataaaaactc gag                      103

<210> SEQ ID NO 72
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 72
aaacaaacaa agctgtcacc ggtgcatggt acgttatatt cagccggtct gatgagtcct      60 gggggggacga aacagcaaaa agaaaaataa aaa                                 93

<210> SEQ ID NO 73
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 73
aaacaaacaa agctgtcacc ggtgcttggt acgttatatt cagccggtct gatgagtctt      60
gaggagacga aacagcaaaa agaaaaataa aaa                                  93

<210> SEQ ID NO 74
<211> LENGTH: 94
<212> TYPE: DNA
<213> ORGANISM: Artificial sequence
<220> FEATURE:
<223> OTHER INFORMATION: Synthetic nucleic acid

<400> SEQUENCE: 74
aaacaaacaa agctgtcacc ggtgcttggt acgttatatt cagccggtct gatgagtcca      60
cagagggacg aaacagcaaa aagaaaaata aaaa                                 94

<210> SEQ ID NO 75
<211> LENGTH: 96
<212> TYPE: DNA
<213> ORGANISM: Artificial sequence
<220> FEATURE:
<223> OTHER INFORMATION: Synthetic nucleic acid

<400> SEQUENCE: 75
aaacaaacaa agctgtcacc ggagatgcgt ggtacgttat attccgtccg gtctgatgag      60
tccagaggga cgaaacagca aaagaaaaa taaaaa                                96

<210> SEQ ID NO 76
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 76
aaacaaacaa agctgtcacc ggtgcttggt acgttatatt cagccggtct gatgagtctt      60
ggagagacga aacagcaaaa agaaaaataa aaa                                  93

<210> SEQ ID NO 77
<211> LENGTH: 97
<212> TYPE: DNA
<213> ORGANISM: Artificial sequence
```

<220> FEATURE:
<223> OTHER INFORMATION: Synthetic nucleic acid

<400> SEQUENCE: 77
aaacaaacaa agctgtcacc ggagttgcgt ggtacgttat attccgtccg gtctgatgag     60
tccaaagggg acgaaacagc aaaagaaaa ataaaaa                              97

<210> SEQ ID NO 78
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 78
aaacaaacaa agctgtcacc ggtgcttggt acgttatatt cagccggtct gatgagtctt     60
gaagagacga aacagcaaaa agaaaaataa aaa                                 93

<210> SEQ ID NO 79
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 79
aaacaaacaa agctgtcacc ggtgcttggt acgttatatt cagccggtct gatgagtctt     60
caagagacga aacagcaaaa agaaaaataa aaa                                 93

<210> SEQ ID NO 80
<211> LENGTH: 94
<212> TYPE: DNA
<213> ORGANISM: Artificial sequence
<220> FEATURE:
<223> OTHER INFORMATION: Synthetic nucleic acid

<400> SEQUENCE: 80
aaacaaacaa agctgtcacc ggtgcttggt acgttatatt cagccggtct gatgagtcca     60 aaggggacg aaacagcaaa aagaaaaata aaaa                                 94

<210> SEQ ID NO 81
<211> LENGTH: 99
<212> TYPE: DNA
<213> ORGANISM: Artificial sequence
<220> FEATURE:
<223> OTHER INFORMATION: Synthetic nucleic acid

<400> SEQUENCE: 81
aaacaaacaa agctgtcacc ggaggtgtag tccggtctga tgagtccgtt gcgtggtacg     60
ttatattccg ggacgaaaca gcaaaagaa aaataaaaa                            99

<210> SEQ ID NO 82
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 82
aaacaaacaa agctgtcacc ggtgcttggt acgttatatt cagccggtct gatgagtcct     60
ggagggacga aacagcaaaa agaaaaataa aaa                                 93

<210> SEQ ID NO 83
<211> LENGTH: 97
<212> TYPE: DNA
<213> ORGANISM: Artificial sequence
<220> FEATURE:
<223> OTHER INFORMATION: Synthetic nucleic acid

<400> SEQUENCE: 83
aaacaaacaa agctgtcacc ggagttgcgt ggtacgttat attccgtccg gtctgatgag    60
tctagaagag acgaaacagc aaaaagaaaa ataaaaa    97

<210> SEQ ID NO 84
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 84
aaacaaacaa agctgtcacc ggtgcttggt acgttatatt cagccggtct gatgagtctt    60
aaagagacga acagcaaaa agaaaaataa aaa    93

<210> SEQ ID NO 85
<211> LENGTH: 94
<212> TYPE: DNA
<213> ORGANISM: Artificial sequence
<220> FEATURE:
<223> OTHER INFORMATION: Synthetic nucleic acid

<400> SEQUENCE: 85
aaacaaacaa agctgtcacc ggtgcttggt acgttatatt cagccggtct gatgagtcca    60 tagggacg aaacagcaaa aagaaaaata aaaa    94

<210> SEQ ID NO 86
<211> LENGTH: 80
<212> TYPE: DNA
<213> ORGANISM: Artificial sequence
<220> FEATURE:
<223> OTHER INFORMATION: Synthetic nucleic acid

<400> SEQUENCE: 86
aaacaaacaa agctgtcacc ggatgtgctt tccggtacgt gaggtccgtg aggacagaac    60
agcaaaaaga aaaataaaaa    80

<210> SEQ ID NO 87
<211> LENGTH: 80
<212> TYPE: DNA
<213> ORGANISM: Artificial sequence
<220> FEATURE:
<223> OTHER INFORMATION: Synthetic nucleic acid

<400> SEQUENCE: 87
aaacaaacaa agctgtcacc ggatgtgctt tccggtctga tgagtccgtg aggacgaaac    60
agcaaaaaga aaaataaaaa    80

<210> SEQ ID NO 88
<211> LENGTH: 90
<212> TYPE: RNA
<213> ORGANISM: Artificial Sequence
<220> FEATURE:
<223> OTHER INFORMATION: Synthetic sequence

<400> SEQUENCE: 88

```
gcugucaccg gaugugcuuu ccggucugau gaguccguug gucguugcgu gguacguuau    60
auuccgggcc gaacgggagg acgaaacagc                                    90

<210> SEQ ID NO 89
<211> LENGTH: 89
<212> TYPE: RNA
<213> ORGANISM: Artificial Sequence
<220> FEATURE:
<223> OTHER INFORMATION: Synthetic sequence

<400> SEQUENCE: 89
gcugucaccg gaugugcuuu ccggucugau gaguccguug cucguugcgu gguacguuau    60
auuccggggc gaacggagga cgaaacagc                                     89

<210> SEQ ID NO 90
<211> LENGTH: 70
<212> TYPE: RNA
<213> ORGANISM: Artificial Sequence
<220> FEATURE:
<223> OTHER INFORMATION: Synthetic sequence

<400> SEQUENCE: 90
ugcucguguc aaaaugaaug gcgcucggcg uugcguggua cguuauauuc cggccaagca    60
gccauucaug                                                          70

<210> SEQ ID NO 91
<211> LENGTH: 29
<212> TYPE: RNA
<213> ORGANISM: Artificial Sequence
<220> FEATURE:
<223> OTHER INFORMATION: Synthetic sequence

<400> SEQUENCE: 91
ggugaccugg acguuauuuc cggccgaag                                     29

<210> SEQ ID NO 92
<211> LENGTH: 70
<212> TYPE: RNA
<213> ORGANISM: Artificial Sequence
<220> FEATURE:
<223> OTHER INFORMATION: Synthetic sequence

<400> SEQUENCE: 92
gcuuaccgga cgccuuaagg caucagcaug cagugcuugg uacguuauau ucagcugcaa    60
cucgggaugc                                                          70

<210> SEQ ID NO 93
<211> LENGTH: 69
<212> TYPE: RNA
<213> ORGANISM: Artificial Sequence
<220> FEATURE:
<223> OTHER INFORMATION: Synthetic sequence

<400> SEQUENCE: 93
gcuauaaguc ggacuucccg ucagguacgu uauauucggg ggaguacggu uaaagcagau    60
uuguugaau                                                           69

<210> SEQ ID NO 94
<211> LENGTH: 69
<212> TYPE: RNA
<213> ORGANISM: Artificial Sequence
<220> FEATURE:
```

<223> OTHER INFORMATION: Synthetic sequence

<400> SEQUENCE: 94
uacucccgac ucgucaaugc auauguaacg uuaacggcgc uaccuguaca augcacguuc    60
cgagcgccc                                                           69

<210> SEQ ID NO 95
<211> LENGTH: 70
<212> TYPE: RNA
<213> ORGANISM: Artificial Sequence
<220> FEATURE:
<223> OTHER INFORMATION: Synthetic sequence

<400> SEQUENCE: 95
ccgacacggc gaagagucaa agcaucccu gcauggagcc aacaagcccu gccuccacgc     60
agggcccgug                                                          70

<210> SEQ ID NO 96
<211> LENGTH: 71
<212> TYPE: RNA
<213> ORGANISM: Artificial Sequence
<220> FEATURE:
<223> OTHER INFORMATION: Synthetic sequence

<400> SEQUENCE: 96
gcugaggacu cggcaccgaa uuugccaacg ucggucacg accguaguac acuaccccuc    60
gaaaucacga g                                                       71

<210> SEQ ID NO 97
<211> LENGTH: 70
<212> TYPE: RNA
<213> ORGANISM: Artificial Sequence
<220> FEATURE:
<223> OTHER INFORMATION: Synthetic sequence

<400> SEQUENCE: 97
gcgcaagugc auuaacggug acaccgaaag cuggaaagcc ugacaucgaa cgcaaaaggc    60
ugcguggcau                                                          70

<210> SEQ ID NO 98
<211> LENGTH: 37
<212> TYPE: RNA
<213> ORGANISM: Artificial Sequence
<220> FEATURE:
<223> OTHER INFORMATION: Synthetic sequence

<400> SEQUENCE: 98
uagguucguu gcgugguacg uuauauuccg gaaccua                            37

<210> SEQ ID NO 99
<211> LENGTH: 37
<212> TYPE: RNA
<213> ORGANISM: Artificial Sequence
<220> FEATURE:
<223> OTHER INFORMATION: Synthetic sequence

<400> SEQUENCE: 99
uagguuaguu gcgugguacg uuauauuccg uaaccua                            37

<210> SEQ ID NO 100
<211> LENGTH: 47
<212> TYPE: RNA
<213> ORGANISM: Artificial Sequence
<220> FEATURE:
<223> OTHER INFORMATION: Synthetic sequence

<400> SEQUENCE: 100
uuggcguugc gugcagugag ccuacuggua cguuauauuc cggccaa        47

<210> SEQ ID NO 101
<211> LENGTH: 51
<212> TYPE: RNA
<213> ORGANISM: Artificial Sequence
<220> FEATURE:
<223> OTHER INFORMATION: Synthetic sequence

<400> SEQUENCE: 101
gcuuggcguu gcguggcagu gagccuacug uacguuauau uccggccaag c        51

<210> SEQ ID NO 102
<211> LENGTH: 22
<212> TYPE: RNA
<213> ORGANISM: Artificial Sequence
<220> FEATURE:
<223> OTHER INFORMATION: Synthetic sequence

<400> SEQUENCE: 102
gugcguggua cguuauauuc cg        22

<210> SEQ ID NO 103
<211> LENGTH: 20
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (19)..(19)
<223> OTHER INFORMATION: N is A or G

<400> SEQUENCE: 103
ugcugguacg uuauauucng        20

<210> SEQ ID NO 104
<211> LENGTH: 42
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (34)..(34)
<223> OTHER INFORMATION: N is A or G
<220> FEATURE:
<221> NAME/KEY: Misc_feature
<222> LOCATION: (38)..(38)
<223> OTHER INFORMATION: N is G or A
<220> FEATURE:
<221> NAME/KEY: Misc_feature
<222> LOCATION: (42)..(42)
<223> OTHER INFORMATION: N is U or C

<400> SEQUENCE: 104
cgucugguca cgaccccuc gaaaucacga gggngacnag an        42

<210> SEQ ID NO 105
<211> LENGTH: 28
<212> TYPE: RNA
<213> ORGANISM: Artificial Sequence
<220> FEATURE:
<223> OTHER INFORMATION: Synthetic sequence

<400> SEQUENCE: 105
ggcgaagagu caaagcaucc ccgggccc                                28

<210> SEQ ID NO 106
<211> LENGTH: 114
<212> TYPE: RNA
<213> ORGANISM: Artificial Sequence
<220> FEATURE:
<223> OTHER INFORMATION: Synthetic sequence

<400> SEQUENCE: 106
uuugccaacg ucggucacg accgcuguca ccggaugugc uuccggucu gaugagccg    60 ugaggacgaa acagcacagc cccucgaaau cacgagggag acgagauagg cgga      114

<210> SEQ ID NO 107
<211> LENGTH: 94
<212> TYPE: RNA
<213> ORGANISM: Artificial Sequence
<220> FEATURE:
<223> OTHER INFORMATION: Synthetic sequence

<400> SEQUENCE: 107
gcugucaccg gaugugcuuu ccggucugau gaguccguug cuggcguugc gugguacguu  60
auauuccggc caguucagcg gaggacgaaa cagc                              94

<210> SEQ ID NO 108
<211> LENGTH: 52
<212> TYPE: RNA
<213> ORGANISM: Artificial Sequence
<220> FEATURE:
<223> OTHER INFORMATION: Synthetic sequence

<400> SEQUENCE: 108
gcugucaccg gaugugcuuu ccggucugau gaguccguga ggacgaaaca gc          52

<210> SEQ ID NO 109
<211> LENGTH: 19
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(13)
<223> OTHER INFORMATION: n is a, c, g, or u

<400> SEQUENCE: 109
accggannnn nnnuccggu                                                19

<210> SEQ ID NO 110
<211> LENGTH: 18
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(12)
<223> OTHER INFORMATION: n is a, c, g, or u

<400> SEQUENCE: 110
accggannnn nnuccggu                                                 18

<210> SEQ ID NO 111
<211> LENGTH: 35

```
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(8)
<223> OTHER INFORMATION: n is a, c, g, or u

<400> SEQUENCE: 111
accggagnug cgugguacgu uauauuccgu ccggu                     35

<210> SEQ ID NO 112
<211> LENGTH: 31
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (25)..(25)
<223> OTHER INFORMATION: n is a, c, g, or u

<400> SEQUENCE: 112
accggugcnu gguacguuau auucngccgg u                         31

<210> SEQ ID NO 113
<211> LENGTH: 13
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(10)
<223> OTHER INFORMATION: n is a, c, g, or u

<400> SEQUENCE: 113
accnnnnnnn ggu                                             13

<210> SEQ ID NO 114
<211> LENGTH: 33
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: n is a, c, g, or u

<400> SEQUENCE: 114
accgggnugc gugguacguu auauuccgcc ggu                       33

<210> SEQ ID NO 115
<211> LENGTH: 31
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: n is a, c, g, or u

<400> SEQUENCE: 115
```

```
guccgnugcg ugguacguua uauuccggga c                                         31

<210> SEQ ID NO 116
<211> LENGTH: 27
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u

<400> SEQUENCE: 116
gucugcnugg uacguuauau ucnggac                                              27

<210> SEQ ID NO 117
<211> LENGTH: 14
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(10)
<223> OTHER INFORMATION: n is a, c, g, or u

<400> SEQUENCE: 117
guccnnnnnn ggac                                                            14

<210> SEQ ID NO 118
<211> LENGTH: 13
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(10)
<223> OTHER INFORMATION: n is a, c, g, or u

<400> SEQUENCE: 118
gucnnnnnnn gac                                                             13

<210> SEQ ID NO 119
<211> LENGTH: 12
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(9)
<223> OTHER INFORMATION: n is a, c, g, or u

<400> SEQUENCE: 119
gucnnnnnng ac                                                              12

<210> SEQ ID NO 120
<211> LENGTH: 33
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
```

```
<222> LOCATION: (7)..(7)
<223> OTHER INFORMATION: n is a, c, g, or u

<400> SEQUENCE: 120
gucccgnugc gugguacguu auauuccggg gac                              33

<210> SEQ ID NO 121
<211> LENGTH: 29
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (24)..(24)
<223> OTHER INFORMATION: n is a, c, g, or u

<400> SEQUENCE: 121
guccugcnug guacguuaua uucngggac                                   29

<210> SEQ ID NO 122
<211> LENGTH: 13
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(10)
<223> OTHER INFORMATION: n is a, c, g, or u

<400> SEQUENCE: 122
gucnnnnnnn gac                                                    13

<210> SEQ ID NO 123
<211> LENGTH: 29
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (22)..(22)
<223> OTHER INFORMATION: n is a, c, g, or u

<400> SEQUENCE: 123
uggcgncuua uauugcaugg uncgugcca                                   29

<210> SEQ ID NO 124
<211> LENGTH: 64
<212> TYPE: RNA
<213> ORGANISM: Artificial Sequence
<220> FEATURE:
<223> OTHER INFORMATION: Synthetic sequence

<400> SEQUENCE: 124
gcugucaccg gugcuuggua cguuauauuc agccggucug augaguccaa ggggacgaaa 60
cagc                                                              64

<210> SEQ ID NO 125
```

```
<211> LENGTH: 60
<212> TYPE: RNA
<213> ORGANISM: Artificial Sequence
<220> FEATURE:
<223> OTHER INFORMATION: Synthetic sequence

<400> SEQUENCE: 125
gcugucaccg gugcuuggua cguuauauuc agccggucug augagucugg acgaaacagc    60

<210> SEQ ID NO 126
<211> LENGTH: 62
<212> TYPE: RNA
<213> ORGANISM: Artificial Sequence
<220> FEATURE:
<223> OTHER INFORMATION: Synthetic sequence

<400> SEQUENCE: 126
gcugucaccg gaguugcgug guacguuaua uuccguccgg ucugaugagu cgacgaaaca    60
gc                                                                  62

<210> SEQ ID NO 127
<211> LENGTH: 71
<212> TYPE: RNA
<213> ORGANISM: Artificial Sequence
<220> FEATURE:
<223> OTHER INFORMATION: Synthetic sequence

<400> SEQUENCE: 127
gcugucaccg gagguguagu ccggucugau gaguccguug cguggacgu uauauuccgg     60 gacgaaacag c                                                        71

<210> SEQ ID NO 128
<211> LENGTH: 173
<212> TYPE: RNA
<213> ORGANISM: Artificial Sequence
<220> FEATURE:
<223> OTHER INFORMATION: Synthetic sequence

<400> SEQUENCE: 128
gaacgggucc ucacuacccc ucgaaaucac gagggagacc agauaagagc gacggcggag    60
cgagcacaag cuggaguaca acuauaguga agccacagau guauaguugu acuccagcuu   120
gugcccgccu ugccaaccau aacucugcuc acgaccguag uaagggcccg uuu          173

<210> SEQ ID NO 129
<211> LENGTH: 27
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: N is any complementary pair of nucleotide
<220> FEATURE:
<221> NAME/KEY: Misc_feature
<222> LOCATION: (2)..(2)
<223> OTHER INFORMATION: N is any complementary pair of nucleotide
<220> FEATURE:
<221> NAME/KEY: Misc_feature
<222> LOCATION: (4)..(4)
<223> OTHER INFORMATION: N is any nucleotide
<220> FEATURE:
<221> NAME/KEY: Misc_feature
<222> LOCATION: (26)..(26)
<223> OTHER INFORMATION: N is any complementary pair of nucleotides
<220> FEATURE:
<221> NAME/KEY: Misc_feature
```

```
<222> LOCATION: (27)..(27)
<223> OTHER INFORMATION: N is any complementary pair of nucleotide
<220> FEATURE:
<221> NAME/KEY: Misc_feature
<222> LOCATION: (27)..(27)
<223> OTHER INFORMATION: N is any complementary pair of nucleotides

<400> SEQUENCE: 129
nngnugcgug guacguuaua uuccgnn                                            27

<210> SEQ ID NO 130
<211> LENGTH: 25
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: N is any complementary pair of nucleotides
<220> FEATURE:
<221> NAME/KEY: Misc_feature
<222> LOCATION: (2)..(2)
<223> OTHER INFORMATION: N2 is a complementary pair of nucleotides
<220> FEATURE:
<221> NAME/KEY: Misc_feature
<222> LOCATION: (6)..(6)
<223> OTHER INFORMATION: N3 is any nucleotide
<220> FEATURE:
<221> NAME/KEY: Misc_feature
<222> LOCATION: (22)..(22)
<223> OTHER INFORMATION: N is an A or G nucleotide
<220> FEATURE:
<221> NAME/KEY: Misc_feature
<222> LOCATION: (24)..(24)
<223> OTHER INFORMATION: N is any complementary pair of nucleotides
<220> FEATURE:
<221> NAME/KEY: Misc_feature
<222> LOCATION: (25)..(25)
<223> OTHER INFORMATION: N is any complementary pair of nucleotides

<400> SEQUENCE: 130
nnugcnuggu acguuauauu cngnn                                              25

<210> SEQ ID NO 131
<211> LENGTH: 46
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (16)..(16)
<223> OTHER INFORMATION: N is any complementary pair of nucleotides
<220> FEATURE:
<221> NAME/KEY: Misc_feature
<222> LOCATION: (17)..(17)
<223> OTHER INFORMATION: N is any complementary pair of nucleotides
<220> FEATURE:
<221> NAME/KEY: Misc_feature
<222> LOCATION: (18)..(18)
<223> OTHER INFORMATION: N is any complementary pair of nucleotides
<220> FEATURE:
<221> NAME/KEY: Misc_feature
<222> LOCATION: (19)..(19)
<223> OTHER INFORMATION: N is any complementary pair of nucleotides
<220> FEATURE:
<221> NAME/KEY: Misc_feature
<222> LOCATION: (38)..(38)
<223> OTHER INFORMATION: N is an A or G nucleotide;
<220> FEATURE:
<221> NAME/KEY: Misc_feature
<222> LOCATION: (42)..(42)
<223> OTHER INFORMATION: N is an A or G nucleotide
<220> FEATURE:
```

<221> NAME/KEY: Misc_feature
<222> LOCATION: (46)..(46)
<223> OTHER INFORMATION: N is a C or U nucleotide

<400> SEQUENCE: 131
cgucugguca cgaccnnnnc ccucgaaauc acgagggnga cnagan                  46

<210> SEQ ID NO 132
<211> LENGTH: 34
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: N is any complementary pair of nucleotides
<220> FEATURE:
<221> NAME/KEY: Misc_feature
<222> LOCATION: (2)..(2)
<223> OTHER INFORMATION: N is any complementary pair of nucleotides
<220> FEATURE:
<221> NAME/KEY: Misc_feature
<222> LOCATION: (25)..(25)
<223> OTHER INFORMATION: N is any complementary pair of nucleotides
<220> FEATURE:
<221> NAME/KEY: Misc_feature
<222> LOCATION: (26)..(26)
<223> OTHER INFORMATION: N is any complementary pair of nucleotides
<220> FEATURE:
<221> NAME/KEY: Misc_feature
<222> LOCATION: (33)..(33)
<223> OTHER INFORMATION: N is any complementary pair of nucleotides
<220> FEATURE:
<221> NAME/KEY: Misc_feature
<222> LOCATION: (34)..(34)
<223> OTHER INFORMATION: N1 is any complementary pair of nucleotides

<400> SEQUENCE: 132
nnggcgaaga gucaaagcau ccccnngggc ccnn                               34

<210> SEQ ID NO 133
<211> LENGTH: 24
<212> TYPE: DNA
<213> ORGANISM: Artificial Sequence
<220> FEATURE:
<223> OTHER INFORMATION: Synthetic sequence

<400> SEQUENCE: 133
tttttttttt tttttttttt tttt                                         24

<210> SEQ ID NO 134
<211> LENGTH: 16
<212> TYPE: RNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (15)..(15)
<223> OTHER INFORMATION: N is any nucleotide
<220> FEATURE:
<221> NAME/KEY: misc_feature
<222> LOCATION: (15)..(15)
<223> OTHER INFORMATION: n is a, c, g, or u

<400> SEQUENCE: 134
gguacguuau auucng                                                  16

COMPOSITIONS AND METHODS FOR REGULATION OF GENE EXPRESSION WITH, AND DETECTION OF, FOLINIC ACID AND FOLATES

CROSS-REFERENCE

This application is a 371 application and claims the benefit of PCT Application No. PCT/US2015/045120, filed Aug. 13, 2015, which claims the benefit of U.S. Provisional Application No. 62/037,015, filed Aug. 13, 2014, which applications are incorporated herein by reference in their entirety.

GOVERNMENT SUPPORT

This invention was made with Government support under contract HR0011-11-2-0002 awarded by the Defense Advanced Research Projects Agency and under contract GM091298 awarded by the National Institutes of Health. The Government has certain rights in the invention.

BACKGROUND OF THE INVENTION

Chemical induction of gene expression is a regulatory tool in nature and in biotechnology for constructing, studying, and engineering biological systems. Inducible promoters and riboswitches found in nature dynamically control metabolism and cellular communication in response to intracellular and environmental signals. Many of these natural systems have been repurposed in biotechnology. However, these systems are restricted to a limited set of existing and well-characterized biological sensing capabilities; are often constrained for use in particular organisms; and may be challenging to functionally decouple from native cellular regulation. Efforts to expand this natural chemical diversity have included significant advances in the engineering of synthetic riboswitches, which can incorporate novel RNA sensors, or aptamers, generated de novo through in vitro selection and operate through varied RNA regulatory mechanisms. See for example, Chang et al. (2012) Current Opinion in Biotechnology 23(5):679-688.

There is a need, therefore, to develop aptamers for gene regulatory systems that can control the expression of specific target genes in vivo in response to effector molecules.

SUMMARY OF THE INVENTION

Compositions and methods are provided that relate to aptamers that specifically bind to ligands of folinic acid, a folate, and derivatives thereof (which may be referred to herein as ligands). The aptamers and switches of the invention provide biological sensing capability for detecting the ligands, and are effective in sensing in vitro and in vivo. The aptamers can be coupled to a suitable actuator, e.g. a priming sequence domain, ribozyme, etc. for regulation of gene expression in response to the ligand. By specific sensing of the ligand, the aptamers of the invention provide a means of engineering an inducible gene regulatory system that enables dose-dependent control over gene expression in response to the ligand, in vivo and in vitro. This technology provides a means for controlling RNA-based, viral, or cellular therapeutics using an externally administered ligand. It also enables diagnostic detection and measurement of the ligand, i.e. folinic acid, folate derivatives, etc. The aptamers also find use as a general inducible gene expression system for a variety of biotechnology applications.

RNA aptamer sensors that bind with high specificity and affinity to folinic acid were generated de novo through in vitro selection. Exemplary sequences are provided herein for high affinity and highly selective sensors. The invention also provides the sequences for functional microRNA-based switches useful in mammalian cells. The sensing and regulatory capabilities are applicable for use in any organism, including bacteria, fungi, plants, mammalian cells, and viruses. The aptamer sensors can be used independently as an in vitro diagnostic tool for folinic acid or other folate derivatives. In addition, the ligand can be modified to alter or remove certain functional groups or to covalently attach other molecules, nucleic acids, proteins, nanoparticles, or drugs of interest, as shown, for example in Table 6.

A benefit of the aptamers of the invention may be the detection of ligands suitable for clinical use. Folinic acid is FDA-approved and clinically used. The folinic acid (6R)-diastereomer is not naturally present in cells, is not biologically active and exhibits high stability and low toxicity, making it highly suitable for gene regulation. These ligand properties enable the developed sensors and gene-regulatory devices of the invention to be widely used in clinically applicable systems.

Compositions of the invention include isolated RNA aptamers and DNA sequences encoding such aptamers; and vectors and cells comprising such RNA and DNA compositions. The RNA aptamers or DNA encoding such aptamers may be operably joined in an aptamer-regulated device, (also referred to as a gene regulatory system), to an actuator, generally a polynucleotide-based actuator, e.g. including without limitation riboswitches, ribozymes, microRNAs, antisense RNAs, RNAi, CRISPR, splicing, small RNAs, ribosome binding sites, internal ribosome entry sites, etc. Compositions of the invention also include isolated RNA devices and DNA sequences encoding such devices; and vectors and cells comprising such devices and encoding sequences.

In addition to a nucleic acid, which is itself functional as an aptamer-regulated device for responding to changes in ligand concentration, (for example a device comprising an aptamer of the invention and an actuator), the invention also provides expression constructs that include a "coding sequence" which, when transcribed to RNA, produces the aptamer-regulated device. The expression construct may include one or more transcriptional regulatory sequences that regulate transcription of that sequence in a cell containing the expression construct. The expression construct can be designed to include one or more actuators in an RNA transcript, such as in the 3' untranslated region (3'-UTR), so as to regulate transcription, stability and/or translation of that RNA transcript in a manner dependent on the ligand. For example, the expression construct can include a coding sequence for a polypeptide such that the mRNA transcript includes both the polypeptide coding sequence as well as one or more of the regulated actuators. In this way, expression of the polypeptide can be rendered dependent on the ligand to which the aptamer binds. The present invention also provides cells that have been engineered to include such expression constructs. Still another aspect of the invention relates to methods for regulating expression of a recombinant gene. Those methods include providing such a cell, and contacting the cell with the ligand in an amount that alters the activity of the actuator, and therefore, the expression of the recombinant gene. In all such embodiments, included those listed below, the folinic acid, a folate, and derivatives thereof can be administered by any convenient means, e.g.

oral, parenteral, in culture medium or growth medium, etc. to regulate expression through the aptamer-regulated device.

Another aspect of the invention provides a cell having a metabolic pathway of one or more reactions, and in which one or more of aptamer-regulated devices act as control elements on the metabolic pathway by regulating expression of one or more target genes. In such embodiments, ligand binding to the aptamer causes a change in the actuator between two conformational states, in one of which the actuator inhibits expression of a target gene and in the other of which the actuator does not inhibit expression of the target gene. In this embodiment, the metabolic pathway is regulated at least in part by the activity level of the actuator, and therefore, the level of ligand that is present. Such embodiments may be used to regulate a metabolic pathway that includes at least one reaction mediated by an enzyme, such as where the actuator regulates expression of the enzyme.

Another aspect of the invention provides a cell having a metabolic pathway of one or more reactions, and in which one or more of the subject aptamer-regulated devices act as control elements on the metabolic pathway by inhibiting expression of one or more target genes into which the device has been engineered so as to be part of the mRNA transcript of the gene, preferably as part of the 3'-UTR. In such embodiments, the ligand binding to the aptamer causes a change in the actuator between two conformational states, in one of which the actuator inhibits expression of the target gene. In this embodiment, the metabolic pathway is regulated at least in part by the activity level of the actuator, and therefore, the level of ligand present. Such embodiments may be used to regulate a metabolic pathway that includes at least one reaction mediated by an enzyme, such as where the actuator regulates expression of the enzyme.

Another aspect of the invention provides a method for rendering expression of a target gene in a cell dependent on the presence or absence of a ligand, by utilizing a version of the subject aptamer-regulated device that, in its active form, cleaves a transcript produced by transcription of the target gene, and thereby inhibits expression of the target gene in a manner dependent on the presence or absence of the ligand.

Likewise, the aptamer-regulated device of the invention can be used to render expression of a target gene in a cell dependent on the presence or absence of a ligand. In these embodiments, the cell is engineered with an expression construct that includes a coding sequence for the target gene, which when transcribed to an mRNA transcript, also includes one or more aptamer-regulated devices in the mRNA. Ligand binding to the aptamer causes a change in the device between two conformational states, in one of which the actuator inhibits expression of the target gene present with the actuator in the same transcript. In this way, the aptamer-regulated device present in the transcript can regulate transcription, stability and/or translation of the mRNA in a manner dependent on the ligand.

In still another embodiment, the present invention provides a method for determining the amount of a ligand of the invention in a cell which expresses a reporter gene by way of the cell also containing an aptamer-regulated device that changes the reporter gene in a manner dependent on the level of the ligand of the invention. The method can include measuring the amount of expression of the reporter gene, and correlating the amount of expression of the reporter gene with the amount of ligand, thereby determining the amount of the ligand in the cell. Exemplary reporter molecules include, without limitation, fluorescent or luminescent reporter proteins such as fluorescent proteins (e.g., green fluorescent protein (GFP), mCherry), luciferase, or aptamers (e.g., Spinach, Spinach2, Broccoli) that specifically bind fluorescent molecules (e.g., 3,5-difluoro-4-hydroxybenzylidene imidazolinone); enzymatic reporters such as alkaline phosphatase; or colorimetric reporters such as lacZ.

In some specific embodiments, an aptamer of the invention is used to regulate a ribozyme. Various ribozymes find use, including without limitation a cis-acting hammerhead ribozyme. In general a regulated ribozyme includes a ribozyme with at least one aptamer of the invention directly coupled to a ribozyme. Suitable switches are provided herein, for example in Table 5 and Table 7. In certain embodiments the aptamer may bind folinic acid, a folate, or derivatives thereof in a manner that alters the base-pairing with a transmitter component that is carried over as a structural change in the ribozyme. In certain embodiments, the aptamer is integrated such that binding of the ligand to the aptamer causes a change with one or more of the loop, the stem or the catalytic core of the ribozyme, such that the ribozyme undergoes self-cleavage of a backbone phosphodiester bond at a rate dependent upon the presence or absence of the ligand. In certain embodiments, the presence of ligand will increase the rate of self-cleavage relative to the absence of ligand, while in other embodiments the rate of self-cleavage is greater in the absence of ligand relative to the presence of ligand. In certain preferred embodiments, the difference in the rate of cleavage is at least 100 fold, and even more preferably 1000 or 10,000 fold.

Another aspect of the invention provides pharmaceutical preparations and compositions comprising an aptamer of the present invention, an aptamer-regulated device, an expression construct which, when transcribed, produces an RNA including the aptamer or aptamer-regulated device, and a pharmaceutically acceptable carrier suitable for administration use to a human or non-human patient. Optionally, the pharmaceutically acceptable carrier is selected from pharmaceutically acceptable salts, ester, and salts of such esters. In certain preferred embodiments, the present invention provides a pharmaceutical package or kit comprising the pharmaceutical preparation which includes at least one aptamer-regulated device and a pharmaceutically acceptable carrier, in association with instructions (written and/or pictorial) for administering the preparation to a human patient.

In one aspect, the disclosure provides an aptamer that specifically binds to a ligand of folinic acid, a folate, or a derivative thereof. In some embodiments, the aptamer is RNA. In some embodiments, the aptamer is up to 50, 55, 60, 65, 70, 75, 80, 85, 90, 95, or 100 nucleotides in length. In some embodiments, the aptamer is an RNA of up to 80 nucleotides in length. In some embodiments, the aptamer is an RNA of from 15 to 80 nucleotides in length. In some embodiments, the ligand is selected from (6S)-folinic acid; (6R)-folinic acid; a diastereomeric mixture of (6R)- and (6S)-folinic acid; tetrahydrofolic acid; (6R)-tetrahydrobiopterin; folic acid; dihydrofolic acid; 5-formiminotetrahydrofolate; 10-formyltetrahydrofolate; 5,10-methenyltetrahydrofolate; 5,10-methylenetetrahydrofolate; levomefolic acid; technetium (99mTc) etarfolatide; tetrahydrofolic acid; vintafolide; methotrexate; pemetrexed; tetrahydrofolic acid; (6R)-tetrahydrobiopterin; (6R,S)-5-methyl-5,6,7,8-tetrahydrofolic acid; (6R)-5-methyl-5,6,7,8-tetrahydrofolic acid; (6S)-5-methyl-5,6,7,8-tetrahydrofolic acid; (6R,S)-5-formyl-5,6,7,8-tetrahydropteroic acid; (6R)-5-formyl-5,6,7,8-tetrahydropteroic acid; (6S)-5-formyl-5,6,7,8-tetrahydropteroic acid; a tagged derivative thereof; and any combination thereof. In some embodiments, the ligand is selected from (6S)-folinic acid; (6R)-folinic acid; a diastereomeric mixture of (6R)- and (6S)-folinic acid; and a tagged derivative thereof. In some embodiments, the aptamer comprises a nucleotide sequence set forth in any one of FIG. 4, FIG. 13, FIG. 14, or FIG. 18; or a variant thereof. In some embodiments, the aptamer comprises a truncated sequence of a nucleotide sequence set forth in any one of FIG. 4, FIG. 13, FIG. 14, or FIG. 18; or a variant thereof. In some embodiments, the aptamer comprises a sequence having at least 50%, 55%, 60%, 65%, 70%, 75%, 80%, 85%, 90%, 95%, 99%, or 100% identity to a truncated sequence. In some embodiments, the aptamer specifically binds (6R)-folinic acid. In some embodiments, the aptamer comprises a sequence having at least 70% identity sequence to FAt8-4, FAt8-11, FAt8-3, FAt6-8, or FAt8-16. In some embodiments, the aptamer specifically binds (6S)-folinic acid. In some embodiments, the aptamer comprises a sequence having at least 70% identity sequence to FAt8-18, FAt10-7, or FAt8-14. In some embodiments, the aptamer comprises a sequence or a sequence having at least 50%, 55%, 60%, 65%, 70%, 75%, 80%, 85%, 90%, 95%, 99%, or 100% identity to a sequence selected from: (i) $N_1$ $N_2$ G $N_3$ U G C G U G G U A C C U U A U A U U C C G $N_4$ $N_5$ (SEQ ID NO:129), where $N_1$ and $N_5$ are any complementary pair of nucleotides; $N_2$ and $N_4$ are any complementary pair of nucleotides; and $N_3$ is any nucleotide; (ii) $N_1$ $N_2$ U G C $N_3$ U G G U A C G U U A U A U U C R G $N_4$ $N_5$ (SEQ ID NO:130), where $N_1$ and $N_5$ are any complementary pair of nucleotides; $N_2$ and $N_4$ are any complementary pair of nucleotides; $N_3$ is any nucleotide; and R is an A or G nucleotide; (iii) C G U C U G G U C A C G A C C $N_1$ $N_2$-$N_3$ $N_4$ C C C U C G A A A U C A C G A G G G R G A C R A G A Y (SEQ ID NO:131), where $N_1$ and $N_4$ are any complementary pair of nucleotides; $N_2$ and $N_3$ are any complementary pair of nucleotides; R is an A or G nucleotide; Y is a C or U nucleotide; and the dash indicates any intervening sequence of nucleotides or two separate nucleotide strands; and (iv) $N_1$ $N_2$ G G C G A A G A G U C A A A G C A U C C C C $N_3$-$N_4$ G G G C C C $N_5$ $N_6$ (SEQ ID NO:132), where $N_1$ and $N_6$ are any complementary pair of nucleotides; $N_2$ and $N_5$ are any complementary pair of nucleotides; $N_3$ and $N_4$ are any complementary pair of nucleotides; and the dash indicates any intervening sequence of nucleotides or two separate nucleotide strands. In some embodiments, the aptamer specifically binds to a ligand with a $K_D$ of up to 100 nM, 200 nM, 300 nM, 400 nM, 500 nM, 600 nM, 700 nM, 800 nM, 900 nM, 1 µM, 2 µM, 3 µM, 4 µM, 5 µM. In some embodiments, the aptamer specifically binds to a ligand with a $K_D$ within the range from 100 µM to 1 µM.

In some embodiments, the aptamer is operably linked to an actuator to generate an aptamer-regulated device. In some embodiments, the actuator is a ribozyme, such as a hammerhead ribozyme. In some embodiments, the aptamer-regulated device comprises a sequence set forth in Table 5. In some embodiments, the actuator is selected from microRNAs, antisense RNAs, RNAi, CRISPR, splicing, small RNAs, ribosome binding sites, internal ribosome entry sites, aptamers, and any combination thereof.

In one aspect, the disclosure provides an aptamer-regulated device, the device comprising an aptamer operably linked to an actuator, wherein the actuator is a hammerhead ribozyme and the aptamer and stem III of the hammerhead ribozyme comprise one or more shared base pairs. In some embodiments, the one or more shared base pairs comprise 2, 3, 4, 5, or more than 5 shared base pairs. In some embodiments, the aptamer-regulated device comprises a hammerhead ribozyme intervening sequence of nucleotides within the aptamer sequence. In some embodiments, the aptamer-regulated device comprises an aptamer or aptamer-regulated device disclosed herein. In some embodiments, the aptamer-regulated device comprises an aptamer that specifically binds to a ligand selected from theophylline, xanthine, 3-methylxanthine, tetracycline, neomycin, hypoxanthine, tetramethylrosamine, p-aminophenylalanine, biotin, 2,4-dinitrotoluene, hoechst 33342, tryptophan, thiamine pyrophosphate, guanine, adenine, 2-aminopurine, azacytosine, ammeline, PPAO, PPDA, purine, and any combination thereof.

In one aspect, the disclosure provides a polynucleotide encoding any aptamer or aptamer-regulated device described herein. In some embodiments, the polynucleotide is a DNA sequence. In one aspect, the disclosure provides a vector comprising any polynucleotide or DNA sequence described herein. In some embodiments, the DNA sequence is operably linked to a promoter for expression in a cell of interest. In one aspect, the disclosure provides a cell comprising any vector described herein.

In one aspect, the disclosure provides a method of regulating gene expression in a cell, the method comprising introducing into the cell any aptamer, DNA sequence, aptamer-regulated device, or vector described herein, under conditions where an actuator acts on a genetic sequence of interest expressed by the cell; and providing the cell with a ligand of the aptamer to regulate gene expression. In some embodiments, the cell is in vivo. In some embodiments, the cell is in vitro. In some embodiments, the genetic sequence of interest encodes a reporter protein. In some embodiments, the genetic sequence of interest encodes a therapeutic protein. In some embodiments, the genetic sequence of interest is an RNA-based therapeutic. In some embodiments, the cell is a mammalian cell, bacterial cell, fungal cell, algal cell, or plant cell.

In one aspect, the disclosure provides a method of modulating RNA expression, the method comprising providing an RNA or a DNA sequence encoding the RNA with a ligand of an aptamer under conditions where an actuator acts on the RNA or the DNA sequence encoding the RNA to modulate RNA expression, wherein the RNA or the DNA sequence encoding the RNA comprises any aptamer, DNA sequence, or aptamer-regulated device described herein. In some embodiments, the providing an RNA or a DNA sequence encoding the RNA with a ligand of an aptamer results in an increase in RNA expression. In some embodiments, the providing an RNA or a DNA sequence encoding the RNA with a ligand of an aptamer results in a decrease in RNA expression.

In one aspect, the disclosure provides a method of modulating protein expression, the method comprising providing an RNA or a DNA sequence encoding a protein with a ligand of an aptamer under conditions where an actuator acts on the RNA or the DNA sequence encoding the protein to modulate protein expression, wherein the RNA or the DNA sequence encoding the protein comprises any aptamer, DNA sequence, or aptamer-regulated device described herein. In some embodiments, the providing an RNA or a DNA sequence encoding a protein with a ligand of an aptamer results in an increase in protein expression. In some embodiments, the providing an RNA or a DNA sequence encoding a protein with a ligand of an aptamer results in a decrease in protein expression.

In one aspect, the disclosure provides a method of determining ligand concentration, the method comprising providing any aptamer, DNA sequence, aptamer-regulated device, vector, or cell described herein with a ligand of the aptamer to determine ligand concentration.

In one aspect, the disclosure provides a method of regulating gene expression, the method comprising providing a ligand of an aptamer to any aptamer, DNA sequence, aptamer-regulated device, vector, or cell described herein, under conditions where an actuator acts on a genetic sequence of interest to regulate gene expression. In some embodiments, the genetic sequence of interest encodes a reporter protein. In some embodiments, the genetic sequence of interest encodes a therapeutic protein. In some embodiments, the genetic sequence of interest is an RNA-based therapeutic. In some embodiments, the cell is a mammalian cell, bacterial cell, fungal cell, algal cell, or plant cell.

In one aspect, the disclosure provides a ligand of folinic acid, a folate, or a derivative thereof for use in regulating gene expression. In one aspect, the disclosure provides a ligand of folinic acid, a folate, or a derivative thereof for use in modulating RNA expression. In one aspect, the disclosure provides a ligand of folinic acid, a folate, or a derivative thereof for use in modulating protein expression. In one aspect, the disclosure provides an aptamer, DNA sequence, aptamer-regulated device, vector, or cell for use in regulating gene expression. In one aspect, the disclosure provides an aptamer, DNA sequence, aptamer-regulated device, vector, or cell for use in modulating RNA expression. In one aspect, the disclosure provides an aptamer, DNA sequence, aptamer-regulated device, vector, or cell for use in modulating protein expression.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

(FIG. 4A-4E) (6R)-folinic acid-specific aptamers FA8-4 (SEQ ID NO:18), FA8-11 (SEQ ID NO:20), FA8-3 (SEQ ID NO:19), FA6-8 (SEQ ID NO:21), and FA8-16 (SEQ ID NO:22), respectively. (FIG. 4F-4H) (6S)-folinic acid-specific aptamers FA8-18 (SEQ ID NO:23), FA10-7 (SEQ ID NO:24), and FA8-14 (SEQ ID NO:7), respectively.

FIG. 5A-5C. Screening of a transmitter library isolates switches that regulate gene expression in response to folinic acid.

(FIG. 6A, 6B) Strand displacement mechanism for (6R)-FA-switch1 (SEQ ID NO:88) and (6R)-FA-switch2 (SEQ ID NO:89), respectively. Active ribozyme conformation with unbound folinic acid aptamer is shown on left, and inactive ribozyme conformation with bound folinic acid aptamer is shown on right. Nucleotides that comprise the sensor, actuator, and transmitter components are colored blue, black, and orange, respectively. Folinic acid is represented by red polygon. Shaded positions within transmitter component are randomized to generate device libraries. (FIG. 6C) Gene regulatory activity in *S. cerevisiae*. Switches maintain aptamer-conferred specificity for (6R)-folinic acid over (6S)-folinic acid in vivo.

FIG. 8A-8C. Validation of small molecule amine coupling to folinic acid. Folinic acid was covalently coupled to n-butylamine in the presence of EDC, NHS, and MES buffer. (FIG. 8A) In the absence of the coupling agent EDC, LC-MS analysis detected only unreacted folinic acid. (FIG. 8B) In the presence of EDC, LC-MS analysis detected both single and double addition product formation and complete conversion of folinic acid substrate into amine-coupled products. (FIG. 8C) Integrated peak values for chromatograms shown in panels (FIG. 8A) and (FIG. 8B). n.d.=not detected.

FIG. 10A-10C. Quantifying ligand concentration on solid support beads after coupling reaction. (FIG. 10A) Representative folinic acid standard curve measured at 274 nm. (FIG. 10B) LC chromatogram for conjugation quantification. ~95% conjugation efficiency seen for coupling 1M folinic acid and 0.1M folinic acid. (FIG. 10C) Integrated peak values for chromatograms shown in panel (FIG. 10B). Concentration of folinic acid remaining in reaction solution is calculated using linear regression fit line of standard curve prepared and run along with reaction samples. Percentage of folinic acid reacted is calculated by subtracting concentration remaining after 2 hrs from initial concentration added. Concentration of folinic acid conjugated onto solid support beads is calculated as twice the difference between the initial concentration added and concentration remaining in reaction solution after 2 hrs, as volume of beads is one-half total reaction volume.

(FIG. 13A-13E) (6R)-folinic acid-specific aptamers FA8-4 (SEQ ID NO:2), FA8-11 (SEQ ID NO:4), FA8-3 (SEQ ID NO:3), FA6-8 (SEQ ID NO:5), and FA8-16 (SEQ ID NO:6), respectively. (FIG. 13F-13H) (6S)-folinic acid-specific aptamers FA8-18 (SEQ ID NO:7), FA10-7 (SEQ ID No:8), and FA8-14 (SEQ ID NO:9), respectively. Circled nucleotide in FA8-4 in panel (FIG. 13A) was changed to a U to facilitate base pairing in characterized truncated sequences without affecting binding affinity.

FIG. 25A: SEQ ID NO:124; FIG. 25B: SEQ ID NO:125; FIG. 25E: SEQ ID NO:126; and FIG. 25F: SEQ ID NO:127.

(FIG. 26A) Predicted secondary structure of folinic acid-responsive miRNA switch. Aptamer nucleotides are highlighted in red. Blue arrows indicate sites of Drosha enzymatic cleavage. SEQ ID NO:128. (FIG. 26B) Dose-dependent silencing activity of a single copy of the miRNA switch. (FIG. 26C) Silencing activity of two copies of the miRNA switch.

DETAILED DESCRIPTION OF THE INVENTION

Figure 1:
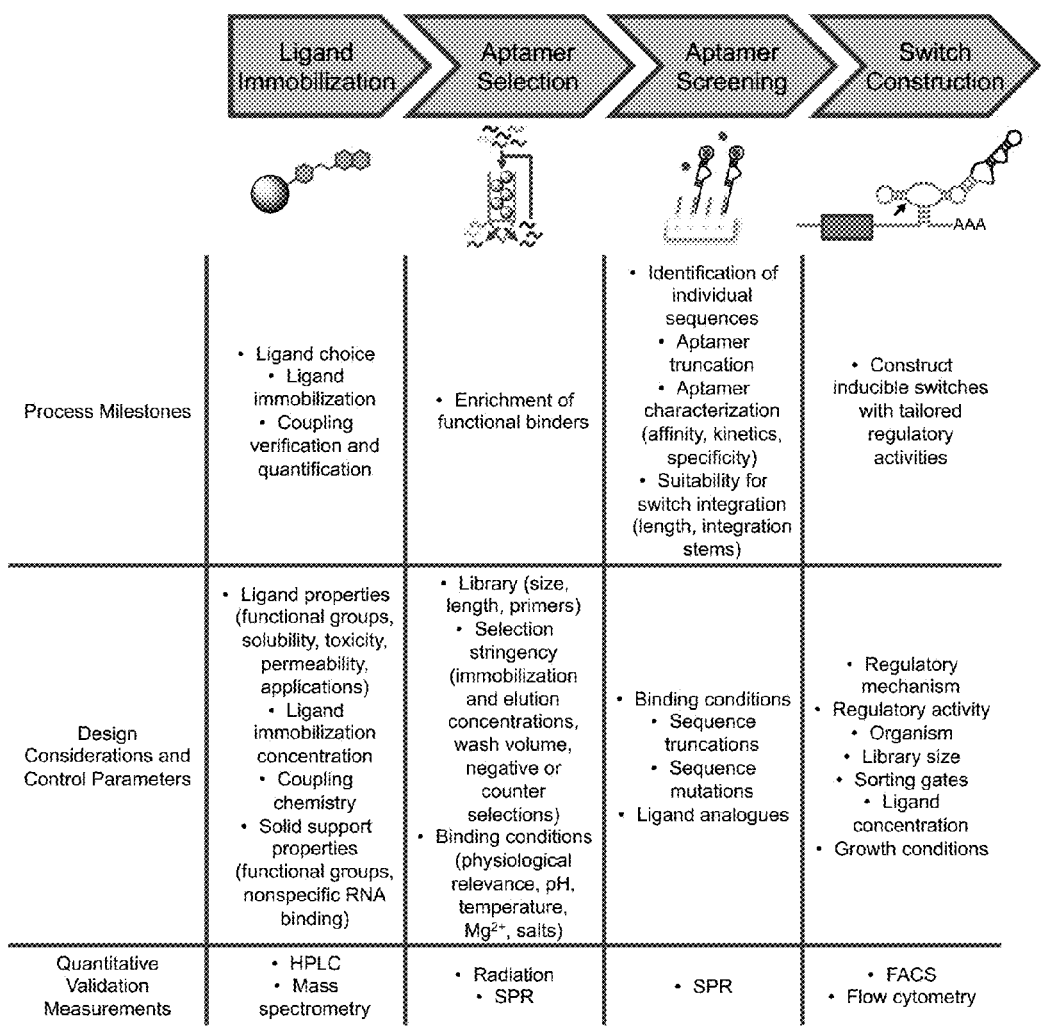
FIG. 1. Workflow diagram for de novo, in vitro selection of RNA aptamer sensors and their integration into synthetic RNA regulatory switches. Design considerations, control parameters, and validation measurements assist in achieving process milestones and increase the likelihood for successful aptamer and switch function, particularly in intracellular environments.

Engineered biological systems hold promise in addressing pressing human needs in chemical processing, energy production, materials construction, and maintenance and enhancement of human health and the environment. However, significant advancements in the ability to engineer biological systems have been limited by the foundational tools available for reporting on, responding to, and controlling intracellular components in living systems. In particular, sensors that respond to clinically useful ligands in vivo are needed.

The present invention provides an aptamer-regulated framework for engineering ligand-controlled gene-regulatory systems. An aptamer of the invention is provided as a stand-alone entity, in a device coupled to an actuator, or in a device coupled to a transmitter component and an actuator, which actuator includes without limitation ribozymes, miRNA, etc. A variety of modes of standardized information transmission between the ligand, aptamer and actuator can be employed. For example, these switch platforms may be applied to the construction of transgenic regulatory control systems that are responsive to folinic acid, a folate, or derivatives thereof. In regulating sets of functional proteins, these switches can act to rewire information flow through cellular networks and reprogram cellular behavior in response to changes in the ligand concentration. In regulating reporter proteins, the aptamer-regulated devices can serve as synthetic cellular sensors to monitor temporal and spatial fluctuations in ligand levels. Due to their general applicability, these platforms offer broad utility for applications in synthetic biology, biotechnology, and health and medicine.

The limited set of available aptamers with validated function in vivo is dominated by only a few ligands and is an acute bottleneck in preventing the wider application of RNA-based control devices. In contrast are numerous approaches for constructing synthetic regulatory switches from existing aptamers, including rational design, in vitro selection, genetic screens and selections, fluorescence-activated cell sorting (FACS), cell motility, and in silico computational approaches, and the diversity of regulatory mechanisms available such as transcription, splicing, RNA stability, RNA interference, translation, and post-translational activity.

De novo generation of RNA aptamer sensors through in vitro selection processes is a particularly powerful approach for constructing novel inducible gene expression systems but has remained a considerable challenge. Likely reasons so few in vitro selected aptamers have validated function in regulatory switches in vivo are that in vitro selected components often exhibit reduced activity when transferred to an intracellular environment and that aptamers must be amenable to physical integration into a regulatory platform, without compromising their binding activity. In vivo usage presents additional challenges as it requires high aptamer affinity and specificity, low ligand toxicity, sufficient ligand solubility and membrane permeability for exogenously supplied ligands, minimal ligand metabolism or degradation, lack of interference from intracellular molecules and RNAs, and functional aptamer binding at physiological conditions (e.g., temperature, pH, and salt concentrations, particularly $Mg^{2+}$ levels). These difficulties have resulted in only a handful of in vitro selected aptamers being consistently used and successfully incorporated into cellular gene-regulatory devices, even with the abundance of regulatory switch platforms developed.

Riboswitches and devices are described in, for example, U.S. Pat. Nos. 8,603,996; 8,604,176; and 8,772,464, each herein specifically incorporated by reference.

Definitions

Folinic acid, folates, and derivatives thereof. The aptamers of the present invention are responsive to folinic acid and related compounds as ligands. Shown in FIG. 2, folinic acid is chemically synthesized as a mixture of two diastereomeric isomers, (6S)- and (6R)-folinic acid and is approved for clinical use either as the diastereomeric mixture leuocovorin or as the single (6S) diastereomer levoleucovorin. The (6R)-folinic acid is heterologous and not biologically active, it is metabolized slower, extending its plasma half-life and concentration up to 15-fold and 18-fold, respectively, compared to the (6S) diastereomer. The low toxicity and biological stability of (6R)-folinic acid make it a particularly suitable ligand for RNA-based gene regulation.

Figure 19:
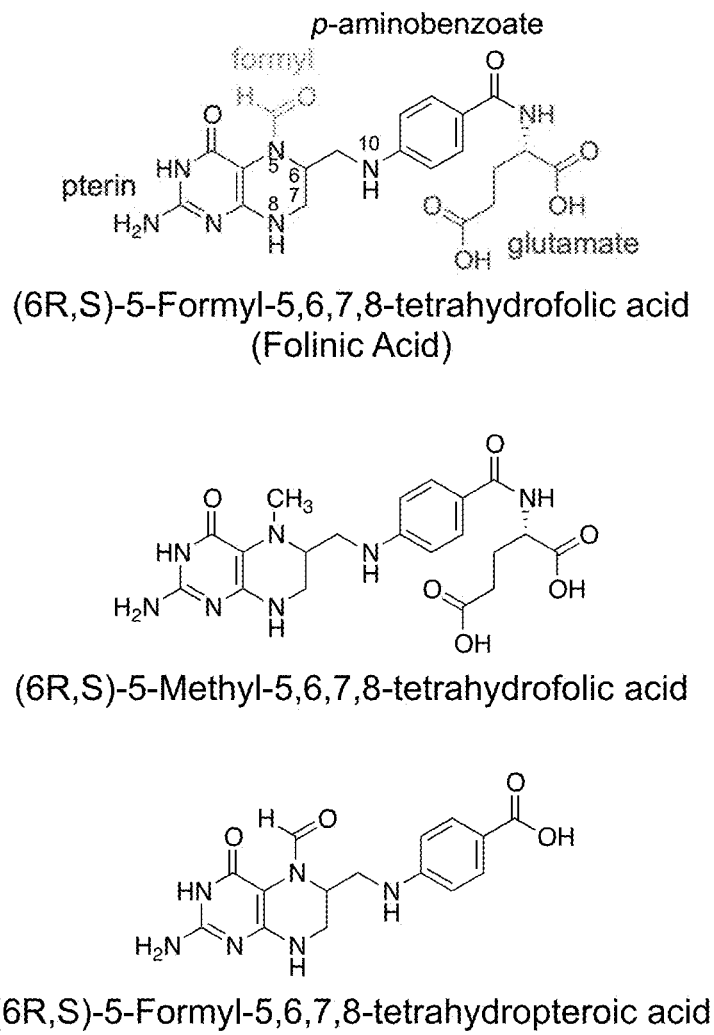
FIG. 19. Structure-activity relationship studies of folinic acid ligand binding. Binding contributions of the formyl and glutamate moieties of folinic acid were studied using folate derivatives. Replacement of the formyl functional group with a methyl group resulting in decreased aptamer affinity, suggesting that the formyl oxygen is involved in hydrogen bonding contacts with one or more nucleotides of the aptamer. Elimination of the glutamate moiety of folinic acid did not impair binding, providing support that the glutamate residue does not significantly participate in binding interactions.

Folates include, without limitation, derivatives with altered specific functionalities of folinic acid, which is composed of pterin, para-aminobenzoate, glutamate, and formyl moieties (FIG. 19). For example, (6R,S)-5-methyl-5,6,7,8-tetrahydrofolic acid replaces the 5-formyl group with a 5-methyl group, testing the role of the formyl oxygen on binding. (6R,S)-5-formyl-5,6,7,8-tetrahydropteroic acid removes the glutamate group through hydrolysis of the amide bond. The glutamate group can be altered or removed without a loss of affinity to the aptamer, thus in some embodiments of the invention (6R,S)-5-formyl-5,6,7,8-tetrahydropteroic acid is useful as a ligand. Folates also include changes in oxidation states, for example folic acid, dihydrofolic acid. The aptamers of the invention also find use in indirect screening for antifolate drugs, e.g., methotrexate, pemetrexed, etc. Folates include, but are not limited to, folic acid, dihydrofolic acid, 5-formiminotetrahydrofolate, 10-formyltetrahydrofolate, 5,10-methenyltetrahydrofolate, 5,10-methylenetetrahydrofolate, levomefolic acid, technetium (99mTc) etarfolatide, tetrahydrofolic acid, antifolates, vintafolide, methotrexate, pemetrexed, tetrahydrofolic acid, (6R)-tetrahydrobiopterin, (6R,S)-5-methyl-5,6,7,8-tetrahydrofolic acid, (6R)-5-methyl-5,6,7,8-tetrahydrofolic acid, (6S)-5-methyl-5,6,7,8-tetrahydrofolic acid, (6R,S)-5-formyl-5,6,7,8-tetrahydropteroic acid, (6R)-5-formyl-5,6,7,8-tetrahydropteroic acid, and (6S)-5-formyl-5,6,7,8-tetrahydropteroic acid.

For screening and monitoring purposes, the chemical functional groups present within folinic acid are amenable for covalent coupling, e.g. to columns, reporter molecules, radioactive labels, and the like. Since the glutamate moiety of folinic acid is not necessary for ligand binding, tagged derivatives of folinic acid can be synthesized, using the glutamate residue of folinic acid or the benzoic acid of 5-formyl-5,6,7,8-tetrahydropteoric acid as a chemical handle to couple a cargo such as a fluorophore tag. The availability of diverse folate analogues can also be mined to test the effect of different oxidation states of the carbon atoms in the 5, 6, 7, or 8 positions or ligand conformation through derivatives that bridge the 5' and 10' nitrogens.

Ligand: "Ligand" or "analyte" or grammatical equivalents herein is meant to refer to any folinic acid, folate, or derivative thereof, including tagged derivatives, to be detected and that can interact with an aptamer of the invention.

The terms "nucleic acid molecule" and "polynucleotide" refer to deoxyribonucleotides or ribonucleotides and polymers thereof in either single- or double-stranded form. The term "RNA" (such as the RNA comprising one or more aptamers) refers to ribonucleic acid, preferably in single-stranded form. Unless specifically limited, the terms encompass nucleic acids/RNAs containing known analogues of natural nucleotides which have similar binding properties as the reference nucleic acid and are metabolized in a manner similar to naturally occurring nucleotides. The terms may also encompass nucleic acids/RNAs containing chemical modifications, such as modifications at the base moiety, sugar moiety, and/or phosphate backbone, that tend to increase stability or half-life of the molecules in vivo. For example, these molecules may have naturally occurring phosphodiester linkages, as well as those having non-naturally occurring linkages, e.g., for stabilization purposes, or for enhancing hydrophobic interaction with protein ligands. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, expression vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a detectable label.

Aptamer. As used herein, the terms "aptamer(s)" or "aptamer sequence(s)" are meant to refer to single stranded nucleic acids (RNA or DNA) whose distinct nucleotide sequence determines the folding of the molecule into a unique three dimensional structure, allowing it to bind to a ligand of the invention at a high affinity. Aptamers comprising 15 to 120 nucleotides can be selected from a pool of oligonucleotides. It will be understood by one of skill in the art that an aptamer sequence can be encoded and expressed from an expression construct, using vectors and promoters known in the art.

Aptamers have specific binding regions which are capable of binding the ligand in an environment wherein other substances in the same environment are not bound to the nucleic acid. The specificity of the binding is defined in terms of the comparative dissociation constants ($K_d$) of the aptamer for its ligand as compared to the dissociation constant of the aptamer for other materials in the environment or unrelated molecules in general. A ligand is one which binds to the aptamer with greater affinity than to unrelated material. Typically, the $K_d$ for the aptamer with respect to its ligand will be at least about 10-fold less than the $K_d$ for the aptamer with unrelated material or accompanying material in the environment. Even more preferably, the $K_d$ will be at least about 50-fold less, more preferably at least about 100-fold less, and most preferably at least about 200-fold less. An aptamer will typically be between about 10 and about 100 nucleotides in length. More commonly, an aptamer will be between about 15 and about 50 nucleotides in length, and truncated aptamer binding moieties disclosed herein are typically from about 15-75 nucleotides in length, and may be about 15, 20, 25, 30, 35, 40, 45, 50, 55, 60, 65, 70, 75, 80, or 85 nt. in length.

Although not necessary, an aptamer may include at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine. Exemplary modified sugar moiety may be selected from the group including but not limited to arabinose, 2-fluoroarabinose, xylulose, and hexose. Exemplary modified ribose sugar moiety may be selected from the group including but not limited to 2'-fluoro, 2'-O-methyl, and 2'-O-alkyl. Exemplary neutral peptide-like backbone modification include: peptide nucleic acid (PNA) (see, e.g., in Perry-O'Keefe et al. (1996) Proc. Natl. Acad. Sci. USA 93:14670 and in Eglom et al. (1993) Nature 365:566), locked nucleic acid (LNA), bridged nucleic acid (BNA), or modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The aptamer of the invention can be comprised entirely of RNA. In other embodiments of the invention, however, the aptamer can instead be comprised entirely of DNA, or partially of DNA, or partially of other nucleotide analogs. Such aptamer RNAs may be introduced into a cell as a DNA that encodes the aptamer such that transcription results in the aptamer-regulated RNA. Alternatively, an aptamer-regulated RNA itself can be introduced into a cell.

High affinity aptamers useful in the invention include those set forth in FIG. 13 as full-length or, preferably, truncated version. Predicted secondary structures of full-length sequences are shown in FIG. 13, with nucleotides in characterized truncated sequences shown in blue. (6R)-folinic acid-specific aptamers are shown as FA8-4, FA8-11, FA8-3, FA6-8, and FA8-16 (FIGS. 13a, b, c, d, e). (6S)-folinic acid-specific aptamers are shown as FA8-18, FA10-7, and FA8-14 (FIGS. 13f, g, h). The full length sequences obtained from the in vitro selection process are shown in Table 4, and in FIG. 15 (which figure does not show primer binding regions in the sequences).

Figure 17A:
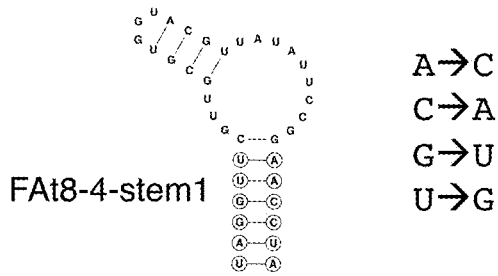
FIG. 17A-17H. Sequence-activity relationship study of folinic acid aptamer FAt8-4. Stem sequence constraints and variable positions were studied to identify minimal binding sequences and aid facile integration of aptamers into regulatory switch platforms. Single-stranded, unlabeled circles represent variable nucleotide positions. Base-paired, unlabeled circles represent nucleotide positions that were variable from parent aptamer based on nucleotide substitutions mentioned in materials and methods section and are possibly either variable as long as base pairing is maintained or are optional base pairs. FAt8-4-stem1: SEQ ID NO:98; Fat8-4-stem2: SEQ ID NO:99; FAt8-4-stem3: SEQ ID NO:100; and FAt8-4stem4: SEQ ID NO:101.
Figure 17B:
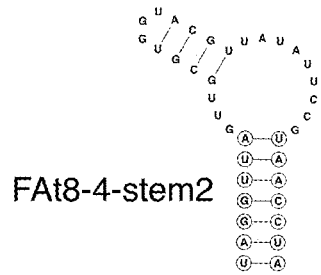
Figure 17C:
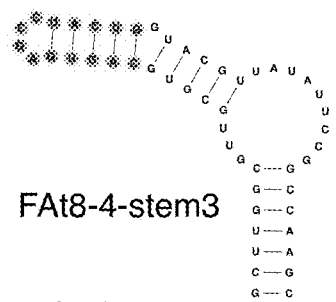
Figure 17D:
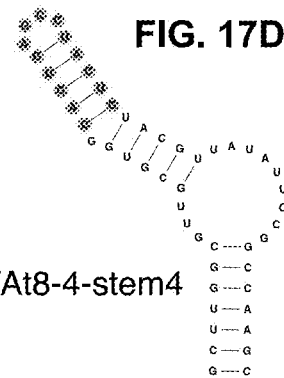
Figure 17E:
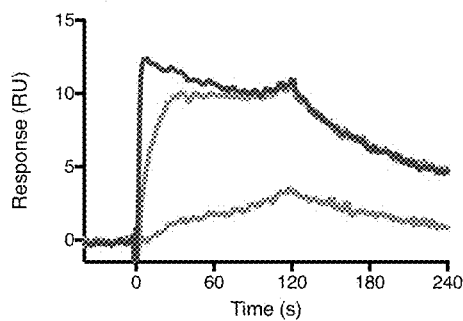
Figure 17F:
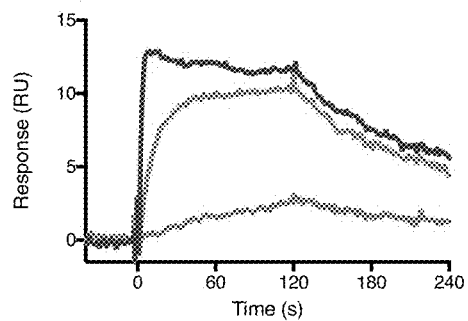
Figure 17G:
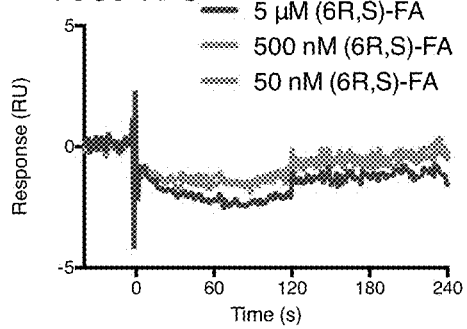
Figure 17H:
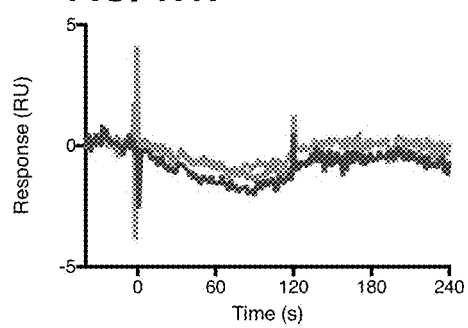
Figure 18:
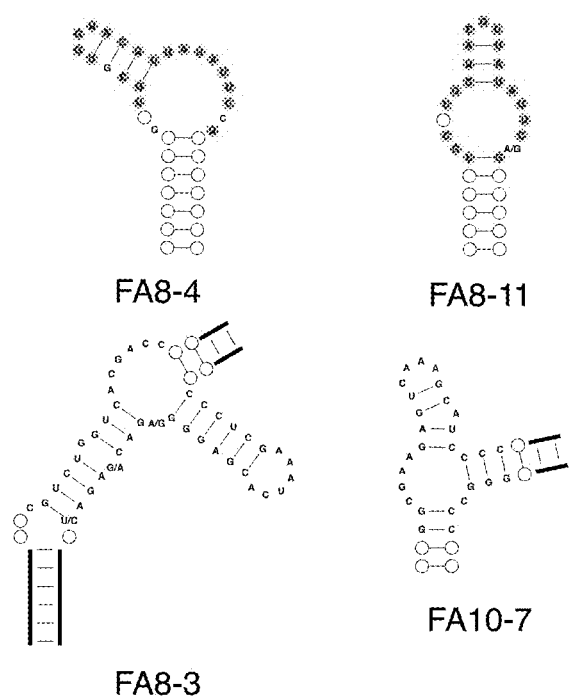
FIG. 18. Sequence-activity relationship studies of folinic acid aptamers. Stem sequence constraints and variable positions were studied to identify minimal binding sequences and aid facile integration of aptamers into regulatory switch platforms. Single-stranded, unlabeled circles represent variable nucleotide positions. Base-paired, unlabeled circles represent nucleotide positions that were variable from parent aptamer based on nucleotide substitutions mentioned in materials and methods section and are possibly either variable as long as base pairing is maintained or are optional base pairs. Nucleotides conserved between aptamers FA8-4 and FA8-11 are indicated in orange. Black lines indicate optional base pairs. FA8-4: SEQ ID NO:102; FA8-11: SEQ ID NO:103; FA8-3: SEQ ID NO:104; and FA10-7: SEQ ID NO:105

Aptamers of the invention can comprise a degenerate sequence, and can further comprise fixed sequences flanking the degenerate sequence. Within the truncated sequence, certain residues are required for binding, while others can be mutated, as shown in FIG. 18. For example, the circled nucleotides in the stem of FAt8-4-stem2 in FIG. 17b were mutated from the original FAt8-4 sequence, demonstrating that the entire base stem can be mutated and still maintain binding activity. The base stem is still required to base pair, but the length of the stem (number of base pairs) can be shortened as long as it still forms. In the sequences provided below, a dash intends that the intervening sequence can be any sequence, or that a functional aptamer is formed by having two separate strands hybridize together.

Exemplary is the truncated form of FA8-4, where the truncated form can be designated FAt8-4. The original FA8-4 sequence is (shown in FIG. 13a):

(SEQ ID NO: 2)
GGGACUUCUGCCCGCCUCCUUCCUGCUCGUGUCAAAAUGAAUGGC<u>GCUC</u>
<u>GGCGUUGCGUGGUACGUUAUAUUCCGGCCAAGC</u>AGCCAUUCAUGGGAGA
CGAGAUAGGCGGACAC

From this initial sequence, the truncated form FAt8-4 is obtained (shown underlined). The C shown in bold was also mutated to a U in FAt8-4, to give the truncated sequence: GCUUGGCGUUGCGUGGUACGUUAUAUUCCGGC-CAAGC (SEQ ID NO:18) Through stem mutations, it is shown that the nucleotides that provide binding activity are: GUUGCGUGGUACGUUAUAUUCCG. The minimally required sequence for binding is:

(SEQ ID NO: 129)
$N_1N_2GN_3UCCGUGGUACGUUAUAUUCCGN_4N_5$, where $N_1$ and $N_5$ are any complementary pair of nucleotides; $N_2$ and $N_4$ are any complementary pair of nucleotides; and $N_3$ is any nucleotide.

For FAt8-11, the minimal required sequence is:

(SEQ ID NO: 130)
$N_1N_2UGCN_3UGGUACGUUAUAUUCRGN_4N_5$, where $N_1$ and $N_5$ are any complementary pair of nucleotides; $N_2$ and $N_4$ are any complementary pair of nucleotides; $N_3$ is any nucleotide; and R is an A or G nucleotide.

For FAt8-3, the minimal required sequence is:

(SEQ ID NO: 131)
$CGUCGGUCACGACCN_1N_2-N_3N_4CCCUCGAAAUCACGAGGGRG$
ACRAGAY, where $N_1$ and $N_4$ are any complementary pair of nucleotides; $N_2$ and $N_3$ are any complementary pair of nucleotides; R is an A or G nucleotide; Y is a C or U nucleotide; and the dash indicates any intervening sequence of nucleotides or two separate nucleotide strands.

For FAt10-7, the minimal required sequence is:

(SEQ ID NO: 132)
$N_1N_2GGCGAAGAGUCAAAGCAUCCCCN_3-N_4GGGCCCN_5N_6$, where $N_1$ and $N_6$ are any complementary pair of nucleotides; $N_2$ and $N_5$ are any complementary pair of nucleotides; $N_3$ and $N_4$ are any complementary pair of nucleotides; and the dash indicates any intervening sequence of nucleotides or two separate nucleotide strands.

Figure 14A:
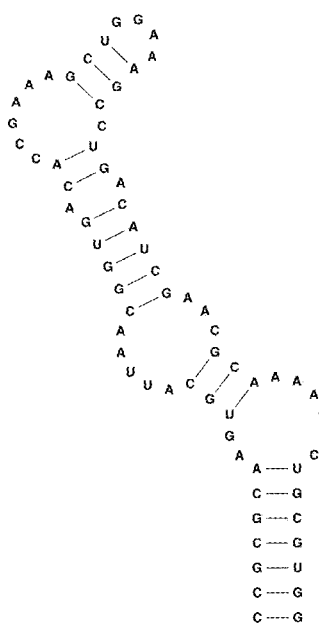
FIG. 14A-14B. Truncation of aptamer FA8-14 (SEQ ID NO:25). Trucated aptamer FAt8-14 retains ability to bind folinic acid but its irregular sensorgram curvature, seen in its trends of not reaching a steady equilibrium plateau and exhibiting negative response values during dissociation phase, preclude proper fitting to a 1:1 binding model and determination of kinetic and equilibrium binding properties.
Figure 14B:
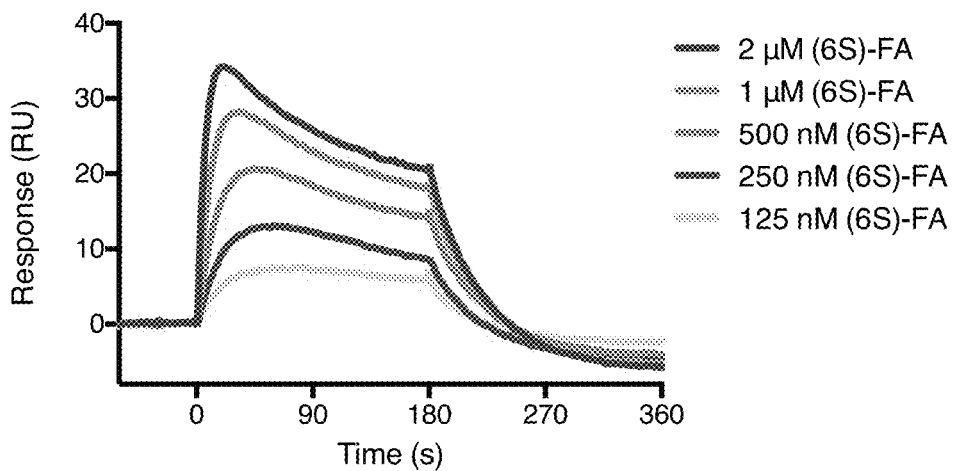

Aptamers of the invention may be "substantially homologous" (or "substantially similar") to the provided sequences, particularly with respect to the truncated sequences provided in FIG. 13 and FIG. 14, and the required residues shown in FIG. 18. Substantially similar variants may vary by a nucleotide substitution or deletion from a provided sequence by 1, 2, 3, 4, 5, 6, 7, 8, 9, 10, 11, 12, 13, 14, 15, 16, 17, 18, 19, 20 nucleotides. Such variants can have at least about 75% sequence similarity, at least about 80% sequence similarity, at least about 85% sequence similarity, at least about 90% sequence similarity, at least about 95% sequence similarity, at least about 99% sequence similarity, or more.

Aptamer sequences can be provided as an isolated nucleic acid, e.g. as a single stranded RNA; can be provided as the encoding DNA sequence, which may be single stranded or double stranded; or may be operably joined to one or both of an actuator component and a transmitter component.

Actuator. An actuator is a component of aptamer-regulated devices of the invention that provides for an activity, e.g. splicing activity; ribozyme activity; transcription; RNA stability; RNA interference; translation; post-translational activity; transcription termination; RNA polymerase recruitment; splice site accessibility; position-dependent splicing; branch point sequence accessibility; ribozyme self-cleavage; Rnt1p enzymatic processing; Drosha pri-miRNA processing; ribozyme-mediated pri-miRNA folding; Dicer shRNA processing; ribosomal binding site (RBS) accessibility; 16S ribosomal RNA; RBS accessibility; ribozyme-mediated RBS accessibility; ribozyme-mediated tRNA; tRNA; mRNA; ribosome binding, scanning, or assembly; antisense RNA binding to start codon; TetR activity; promoter activity; terminator activity; riboswitches; ribozymes; microRNAs; siRNAs; antisense RNAs; RNAi; clustered regularly interspaced short palindromic repeats (CRISPR); CRISPR-Cas9; CRISPR targeting RNA (crRNA); trans-activating crRNA (tracrRNA); guide RNA (gRNA); splicing; small RNAs; ribosome binding sites; internal ribosome entry sites; aptamer; etc. In some specific embodiments the actuator is a ribozyme, including without limitation a hammerhead ribozyme. In some embodiments, the actuator is an aptamer. In other embodiments the actuator is an ampliswitch, as defined in U.S. Pat. No. 8,772,464, herein specifically incorporated by reference. Other actuators of interest include ligand-responsive, microRNA (miRNA) switches that modulate Drosha processing. These switches integrate an aptamer into the basal segments of a miRNA. Internal loop size contained within the basal segments affects Drosha processing and therefore the levels of miRNA-mediated gene silencing. By integrating an aptamer within the basal segments, unbound aptamer can remain relatively unstructured, while ligand binding can sequester nucleotides involved in binding and inhibit Drosha processing. Aptamer-regulated devices include, but are not limited to, RNA switches, ribozyme switches, microRNA switches, an aptamer operably joined or linked to another aptamer, an aptamer operably joined or linked to an actuator, and any combination thereof.

Ribozyme: Ribozymes are RNA molecules with a catalytic activity. Frequently, although not necessarily, the activity is cleavage of a nucleic acid. Other ribozymes may catalyze other chemical reactions and have their catalytic activity controlled using a similar type of switch.

Ribozyme types include, without limitation, hairpin ribozymes, hepatitis delta virus and hepatitis delta virus-like ribozymes, CPEB3 ribozymes, Varkud satellite ribozymes, twister ribozymes, group I and group II introns, and hammerhead ribozymes. Ribozymes have been targeted to a wide variety of substrates and tested in biological systems to achieve the inhibition of cellular gene expression or viral replication. Target specificity may be achieved, for example, by flanking a ribozyme motif with antisense sequences, complementary to the target RNA.

A hammerhead ribozyme contains a core, three stems that extend from the core, referred to herein as stem I, stem II, and stem III, and at least one loop, which is located on the opposite end of a stem from the core. Hammerhead ribozymes can be type I, type II, or type III depending on which stem the ribozyme is integrated through into the transcript As used herein, a "cis-cleaving hammerhead ribozyme" is a hammerhead ribozyme that, prior to cleavage, is comprised of a single polynucleotide. A cis-cleaving hammerhead ribozyme is capable of cleaving itself.

As used herein, a "trans-cleaving hammerhead ribozyme" is a hammerhead ribozyme that, prior to cleavage, is comprised of at least two polynucleotides. One of the polynucleotides is the target sequence that is cleaved.

Ribozyme switches. A molecule that can adopt at least two different conformational states, where each state is associated with a different activity of the molecule. Often a ligand can bind to one or more conformations of the switch, such that the presence of the ligand shifts the equilibrium distribution across the adoptable conformations and therefore regulates the activity of the switch molecule. As used here, switch generally refers to an RNA molecule that can adopt different structures that correspond to different gene-regulatory activities. An RNA switch is then a ligand-controlled gene-regulatory system.

Switching Strand: The nucleic acid sequence within a strand displacement domain that is bound to the general transmission region of the switch when the sensor domain is in the disrupted conformation (i.e., in the absence of ligand). The switching strand is displaced by the competing strand in the presence of ligand.

Figure 20:
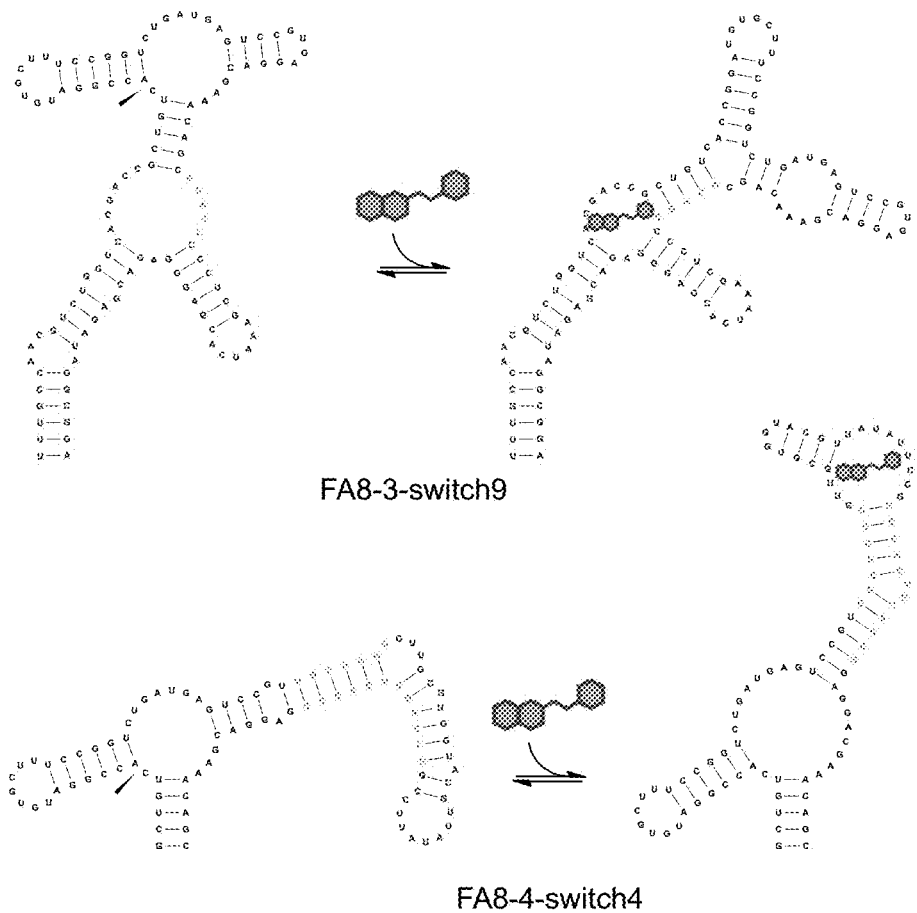
FIG. 20. Strand displacement mechanism for rationally designed folinic acid-responsive switches. FA8-3-switch9: SEQ ID NO:106; and FA8-4-switch4:SEQ ID NO:107.

Strand displacement mechanism is demonstrated herein for architectures with aptamer integration off of the hammerhead loop II, and integration into the transcript through hammerhead helix III (FIG. 20). These switches demonstrate that selected folinic acid aptamers function intracellularly and can be coupled to ribozymes to confer folinic acid-responsive gene regulation. For loop II integration, transmitter sequences from previously characterized switches can be used as a starting point to join folinic acid aptamers to the hammerhead ribozyme, and modified as necessary to achieve proper folding of the ribozyme and aptamer domains. Exemplary switches are provided in Table 5.

Aptamer integration through helix III requires two integration stems on the aptamer:
one for ribozyme helix III integration and another for transcript integration. In this architecture, the ribozyme sequence does not need to be altered, and therefore the native tertiary loop-loop interactions are maintained, with the goal of achieving lower basal activity and eliminating the need to rescue impaired tertiary interactions.

Figure 22:
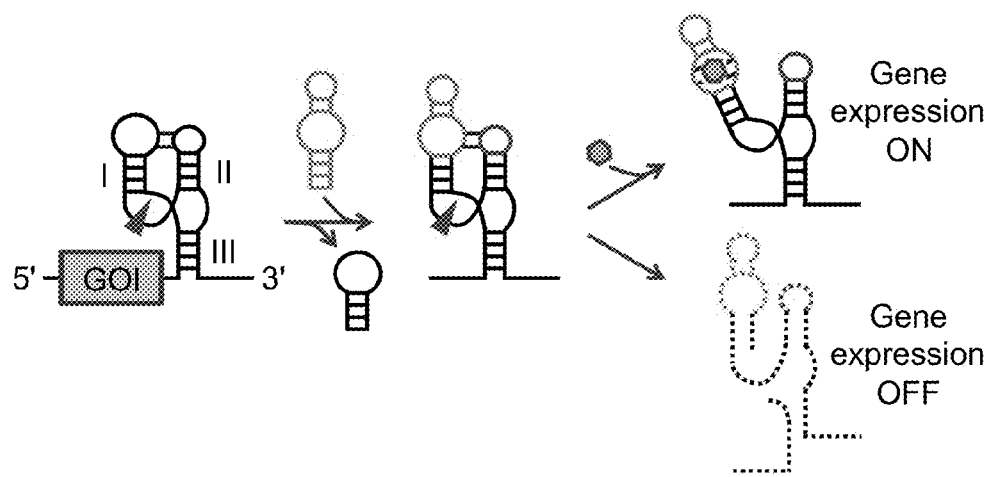
FIG. 22. Strategy for generating ribozyme-based switches through replacement of ribozyme loop with aptamer. Ribozyme is integrated through helix III into 3' UTR of regulated transcript of gene of interest (GOI) (shown in gray). Device library is generated by replacing either loop I or loop II with an aptamer (shown in orange) and randomizing nucleotides of other loop (shown in green). Functional switches are isolated that reconstitute the tertiary ribozyme loop-loop interaction as a tertiary aptamer-loop interaction (shown in blue), enabling ribozyme cleavage in the absence of aptamer ligand. In the presence of ligand, aptamer-ligand binding competitively sequesters nucleotides involved in aptamer-loop interaction, disrupting tertiary interaction, preventing ribozyme cleavage, and allowing translation and expression of gene.

An alternative switch architecture based on ribozyme loop replacement relies on the observation that natural hammerhead ribozymes possess many sequence solutions for maintaining tertiary loop-loop interactions that are crucial for stringent regulatory silencing (FIG. 22). This integration strategy replaces one of the two interacting hammerhead loops with an aptamer, placing an internal or terminal loop of an aptamer approximately in the same position as the replaced ribozyme loop. To rescue the loop-loop interaction, the second loop is completely randomized and the device library is screened for functional switches. In the absence of ligand, nucleotides of the two loops are predicted to interact through tertiary interactions. However, in the presence of ligand, ligand binding to the aptamer sequesters aptamer nucleotides involved in the loop-loop interaction, precluding proper tertiary contact formation and disrupting ribozyme cleavage.

The highest performing switches demonstrated up to 25.2-fold activation ratios (ratio of GFP expression in the presence of ligand to expression in the absence of ligand) in the presence of 3 mM (6R)-folinic acid and dynamic ranges of up to 43.6% (difference between GFP expression in the presence and absence of ligand).

Stem: A stem is a nucleic acid motif that extends from the ribozyme core, at least a portion of which is double-stranded. In certain embodiments, there is a loop at the opposite end of the stem from the ribozyme core, and this loop connects the two strands of the double-stranded stem. In certain embodiments, a stem comprises 2 to 20 complementary base pairs. In certain embodiments, a stem comprises 3, 4, 5, 6, 7, 8, or 9 complementary base pairs. Stems are numbered according to where they extend from the core sequence. In certain embodiments, a hammerhead ribozyme contains three stems, which are referred to as stem I stem II, and stem III.

In certain embodiments, at least 30% of the nucleotides in a stem are part of a complementary base pair. The remaining base pairs may be mismatched, non-complementary base pairs, or may be part of a bulge. In certain embodiments, at least 40% of the nucleotides in a stem are part of a complementary base pair. In certain embodiments, at least 50% of the nucleotides in a stem are part of a complementary base pair. In certain embodiments, at least 60% of the nucleotides in a stem are part of a complementary base pair. In certain embodiments, at least 70% of the nucleotides in a stem are part of a complementary base pair. In certain embodiments, at least 80% of the nucleotides in a stem are part of a complementary base pair. In certain embodiments, at least 90% of the nucleotides in a stem are part of a complementary base pair. In certain embodiments, at least 95% of the nucleotides in a stem are part of a complementary base pair. In certain embodiments, at least 99% of the nucleotides in a stem are part of a complementary base pair. In certain embodiments, 100% of the nucleotides in a stem are part of a complementary base pair.

Loop: A loop is a sequence of nucleotides that is not paired with another strand and is located at the distal end of a stem that is opposite the core. In certain embodiments, a loop is between 1 to 20 nucleotides long. In certain embodiments, a loop is between 2 and 10 nucleotides long. In certain embodiments, a loop is between 3 and 8 nucleotides long. The loop is numbered according to the stem to which it is attached. Therefore, loop I is located at the end of stem I opposite the core, loop II is located at the end of stem II opposite the core, and loop III is located at the end of stem III opposite the core.

As used herein, a "stem/loop" refers to the entire stem, along with any bulges within that stem, and the loop at the end of the stem. For example, stem/loop I includes stem I, including any bulges within stem I, and loop I. If a stem lacks a loop, then stem/loop refers to the stem, along with any bulges within that stem.

Bulge: As used herein, a "bulge" is a sequence of nucleotides that is not paired with another strand and is flanked on both sides by double-stranded nucleic acid sequences. In certain embodiments, a bulge is located within a stem. When a bulge is located within a stem, the nucleotides of the bulge are considered to be part of the stem. In certain embodiments, a hammerhead ribozyme comprises more than one bulge. In certain embodiments, a bulge within a stem is located two base pairs from the core. In certain embodiments, one or both strands of the stem contain a bulge.

Directly Coupled: As used herein, an aptamer is directly coupled to an actuator, e.g., a loop of a ribozyme where the loop, relative to active ribozyme structure in the absence of the aptamer, is interrupted at only one backbone phosphodiester bond between two residues of the loop, the backbone phosphodiester bond being replaced with phosphodiester bonds to the 5' and 3' ends of the aptamer. In the active form of the aptamer-regulated ribozyme, the 5' and 3' residues of the information transmission domain are based paired to one another to form a duplex region in order to preserve the structure of the otherwise interrupted loop.

Information Transmission Domain: A switch domain that encodes the function of transmitting information between the sensor domain and the actuator domain.

Information Transmission Mechanism: A general mechanism for transmitting information between the sensor domain and the actuator domain of a switch. As used here, this mechanism regulates the activity of the actuator domain in response to the binding state of the sensor domain.

Strand Displacement Mechanism: An information transmission mechanism that is based on the rational design of an information transmission domain that functions through a strand displacement event. Such a strand displacement event utilizes competitive binding of two nucleic acid sequences (the competing strand and the switching strand) to a general transmission region of the switch (the base stem of the aptamer) to result in disruption or restoration of the actuator domain in response to restoration of the sensor domain.

For convenient detection, aptamers, aptamer-regulated devices, polynucleotides, or compounds disclosed herein can be conjugated to a detectable label. Suitable detectable labels can include any composition detectable by photochemical, biochemical, spectroscopic, immunochemical, electrical, optical, or chemical means. A wide variety of appropriate detectable labels are known in the art, which include fluorescent labels, chemiluminescent labels, radioactive isotope labels, enzymatic labels, and ligands. The detection methods used to detect or quantify the label will typically depend upon the label selected. For example, radiolabels (e.g., radioactive isotope labels) may be detected using Positron Emission Topography (PET), photographic film, or a phosphoimager. Fluorescent labels (e.g., fluorescent dyes, fluorescent proteins) may be detected and quantified using a photodetector to detect emitted light. In some embodiments, each of a plurality of aptamers, aptamer-regulated devices, polynucleotides, or compounds is conjugated to a different detectable label (e.g., fluorescent dyes with different emission spectra), such that the signal corresponding to different targets can be differentiated. Enzymatic labels are typically detected by providing the enzyme with a substrate and measuring the reaction product produced by the action of the enzyme on the substrate. Colorimetric labels are typically detected by visualizing the colored label or are quantified using a spectrophotometer.

In certain embodiments, the aptamers, aptamer-regulated devices, polynucleotides, or compounds disclosed herein are isotopically labeled. Isotopically-labeled aptamers, polynucleotides, or compounds (e.g., an isotopologue) may have one or more atoms replaced by an atom having a different atomic mass or mass number. Non-limiting examples of isotopes that can be incorporated into the disclosed compounds include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled aptamers, polynucleotides, or compounds, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. These radiolabeled compounds could be useful to help determine or measure the effectiveness of the compounds, by characterizing, for example, the site or mode of action, or binding affinity to a pharmacologically important site of action. Substitution with heavier isotopes such as deuterium ($^{2}H$) may afford certain therapeutic advantages resulting from greater metabolic stability, for example, increased in vivo half-life or reduced dosage requirements, and hence are preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described herein using an appropriate isotopically-labeled reagent in place of the non-labeled reagent.

In some embodiments, an aptamer, aptamer-regulated device, or polynucleotide binds to a ligand with a $K_d$ of about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, 500 µM, or more than 500 µM. In some embodiments, an aptamer, aptamer-regulated device, or polynucleotide binds to a ligand with a $K_d$ of up to about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, or 500 µM. In some embodiments, an aptamer, aptamer-regulated device, or polynucleotide binds to a ligand with a $K_d$ of at least about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, or 500 µM. In some embodiments, an aptamer, aptamer-regulated device, or polynucleotide binds to a ligand with a $K_d$ within the range from 100 pM-100 µM, from 100 pM-10 µM, from 100 pM-1 µM, from 100 pM-900 nM, from 100 pM-800 nM, from 100 pM-700 nM, from 100 pM-600 nM, from 100 pM-500 nM, from 100 pM-400 nM, from 100 pM-300 nM, from 100 pM-200 nM, from 100 pM-100 nM, or from 100 pM-50 nM. In some embodiments, an aptamer, aptamer-regulated device, or polynucleotide binds to a ligand with a $K_d$ of up to about 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, or 1 µM.

In some embodiments, an aptamer-regulated device achieves a half-maximal regulatory response at a concentration of a ligand of about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, 500 µM, or more than 500 µM. In some embodiments, an aptamer-regulated device achieves a half-maximal regulatory response at a concentration of a ligand of up to about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, or 500 µM. In some embodiments, an aptamer-regulated device achieves a half-maximal regulatory response at a concentration of a ligand of at least about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, or 500 µM. In some cases, a regulatory response may include, but is not limited to, RNA expression, protein expression, gene expression, fluorescence, binding, cell viability, cell proliferation, cell motility, and any combination thereof.

In some embodiments, the ratio of a regulatory response in the presence of a ligand to the regulatory response in the absence of the ligand of an aptamer-regulated device is about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some embodiments, the ratio of a regulatory response in the presence of a ligand to the regulatory response in the absence of the ligand of an aptamer-regulated device is at least about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some embodiments, the ratio of a regulatory response in the presence of a ligand to the regulatory response in the absence of the ligand of an aptamer-regulated device is up to about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some cases, a regulatory response is an activation ratio. In some cases, the aptamer-regulated device is modulating RNA expression, protein expression, gene expression, or any combination thereof.

In some embodiments, the ratio of a regulatory response in the absence of a ligand to the regulatory response in the presence of the ligand of an aptamer-regulated device is about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some embodiments, the ratio of a regulatory response in the absence of a ligand to the regulatory response in the presence of the ligand of an aptamer-regulated device is at least about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some embodiments, the ratio of a regulatory response in the absence of a ligand to the regulatory response in the presence of the ligand of an aptamer-regulated device is up to about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some cases, a regulatory response is an activation ratio. In some cases, the aptamer-regulated device is modulating RNA expression, protein expression, gene expression, or any combination thereof.

In some embodiments, an aptamer, aptamer-regulated device, or polynucleotide binds to a ligand with a specificity of about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000;

6,000; 7,000; 8,000; 9,000; 10,000; or more than 10,000. In some embodiments, an aptamer, aptamer-regulated device, or polynucleotide binds to a ligand with a specificity of at least about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some embodiments, an aptamer, aptamer-regulated device, or polynucleotide binds to a ligand with a specificity of up to about 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000. In some cases, specificity is calculated as ($K_d$ of the aptamer to the ligand)/($K_d$ of the aptamer to a reference compound). In some cases, the reference compound is a compound that is not the ligand and is selected from (6S)-folinic acid; (6R)-folinic acid; a diastereomeric mixture of (6R)- and (6S)-folinic acid; tetrahydrofolic acid; (6R)-tetrahydrobiopterin; folic acid; dihydrofolic acid; 5-formiminotetrahydrofolate; 10-formyltetrahydrofolate; 5,10-methenyltetrahydrofolate; 5,10-methylenetetrahydrofolate; levomefolic acid; technetium (99mTc) etarfolatide; tetrahydrofolic acid; vintafolide; methotrexate; pemetrexed; tetrahydrofolic acid; (6R)-tetrahydrobiopterin; (6R,S)-5-methyl-5,6,7,8-tetrahydrofolic acid; (6R)-5-methyl-5,6,7,8-tetrahydrofolic acid; (6S)-5-methyl-5,6,7,8-tetrahydrofolic acid; (6R,S)-5-formyl-5,6,7,8-tetrahydropteroic acid; (6R)-5-formyl-5,6,7,8-tetrahydropteroic acid; (6S)-5-formyl-5,6,7,8-tetrahydropteroic acid; and any combination thereof. In some cases, specificity is calculated as ($K_d$ of the aptamer to (6R)-folinic acid)/($K_d$ of the aptamer to (6S)-folinic acid) or ($K_d$ of the aptamer to (6S)-folinic acid)/($K_d$ of the aptamer to (6R)-folinic acid). In some cases, specificity is calculated as ($K_d$ of the aptamer to (6R)-folinic acid)/($K_d$ of the aptamer to (6R,S)-5-methyl-5,6,7,8-tetrahydrofolic acid) or ($K_d$ of the aptamer to (6S)-folinic acid)/($K_d$ of the aptamer to (6R,S)-5-methyl-5,6,7,8-tetrahydrofolic acid). In some cases, specificity is calculated as ($K_d$ of the aptamer to (6R)-folinic acid)/($K_d$ of the aptamer to (6R,S)-5-formyl-5,6,7,8-tetrahydropteroic acid) or ($K_d$ of the aptamer to (6S)-folinic acid)/($K_d$ of the aptamer to (6R,S)-5-formyl-5,6,7,8-tetrahydropteroic acid).

In some embodiments, an aptamer, aptamer-regulated device, or polynucleotide has a length of about 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; or more than 10,000 nucleotides. In some embodiments, an aptamer, aptamer-regulated device, or polynucleotide has a length of up to 50; 55; 60; 65; 70; 75; 80; 85; 90; 95; 100; 200; 300; 400; 500; 1,000; or 2,000 nucleotides. In some embodiments, an aptamer has a length of up to 50; 55; 60; 65; 70; 75; 80; 85; 90; 95; or 100 nucleotides.

In some embodiments, an aptamer, aptamer-regulated device, or polynucleotide comprises a sequence selected from FAt8-4, FAt8-11, FAt8-3, FAt6-8, FAt8-16, FAt8-18, FAt10-7, and FAt8-14. In some cases, an aptamer, aptamer-regulated device, or polynucleotide comprises a sequence having about 40%, 45%, 50%, 55%, 60%, 65%, 70%, 75%, 80%, 85%, 90%, 95%, 96%, 97%, 98%, 99%, or 100% identity to a sequence selected from FAt8-4, FAt8-11, FAt8-3, FAt6-8, FAt8-16, FAt8-18, FAt10-7, and FAt8-14. In some cases, an aptamer, aptamer-regulated device, or polynucleotide comprises a sequence having at least about 40%, 45%, 50%, 55%, 60%, 65%, 70%, 75%, 80%, 85%, 90%, 95%, 96%, 97%, 98%, 99%, or 100% identity to a sequence selected from FAt8-4, FAt8-11, FAt8-3, FAt6-8, FAt8-16, FAt8-18, FAt10-7, and FAt8-14. In some cases, an aptamer, aptamer-regulated device, or polynucleotide comprises a sequence having up to about 40%, 45%, 50%, 55%, 60%, 65%, 70%, 75%, 80%, 85%, 90%, 95%, 96%, 97%, 98%, 99%, or 100% identity to a sequence selected from FAt8-4, FAt8-11, FAt8-3, FAt6-8, FAt8-16, FAt8-18, FAt10-7, and FAt8-14.

In some cases, an aptamer, aptamer-regulated device, or polynucleotide comprises a sequence having about 40%, 45%, 50%, 55%, 60%, 65%, 70%, 75%, 80%, 85%, 90%, 95%, 96%, 97%, 98%, 99%, or 100% identity to single-stranded regions of a sequence selected from FAt8-4, FAt8-11, FAt8-3, FAt6-8, FAt8-16, FAt8-18, FAt10-7, and FAt8-14 as determined by the secondary structure (e.g., as shown in FIG. 4, 13, 14, 17, or 18).

Delivery

RNA or nucleic acid molecules of the invention can be delivered to target cells in vivo, through any convenient mechanism, including without limitation transfection, infection, electroporation, etc. Target cells may include plant cells, animal cells, prokaryotes, fungi, etc. Target cells may include bacteria, fungi, plant protoplasts and chloroplasts, and mammalian cell lines. Cells may include, but are not limited, to *S. cerevisiae*, HeLa, CTLL-2, primary human $T_{CM}$, HEK293, U2OS, SK-MEL-28, A549, Colo 829, NCH89, Vero, SK-MEL-28, Capan-1, A549, CHO, HepG2, *X laevis, A. baumannii, A. baylyi, A. tumefaciens, B. subtilis, E. coli, M. magneticum, M. smegmatis, S. pyogenes*, Cucumber protoplast, *M. tuberculosis, M. smegmatis, S. coelicolor, S. elongatus, N. tabacum* chloroplasts, *Francisella*. Vectors of interest include, without limitation, viral vectors, mini-circle vectors, plasmids and include episomal vectors that replicate autonomously, as well as vectors that are integrated into a chromosome of the cell. The initial introduction of the nucleic acid can be performed in vitro, in vivo, or ex vivo, as required for the specific use.

Vectors can be plasmid, viral, or others known in the art, used for replication and expression in cells, e.g. mammalian cells, plant cells, etc. A promoter may be operably linked to the sequence encoding the subject RNA. Expression of the subject encoded sequences can be by any promoter known in the art to act in mammalian, preferably human cells. Such promoters can be inducible or constitutive. Such promoters include but are not limited to: the SV40 early promoter region (Bernoist and Chambon, Nature 290:304-310 (1981)), the promoter contained in the 3' long terminal repeat of Rous sarcoma virus (Yamamoto et al., Cell 22:787-797 (1980)), the herpes thymidine kinase promoter (Wagner et al., Proc. Natl. Acad. Sci. USA 78:1441-1445 (1981)), the regulatory sequences of the metallothionine gene (Brinster et al, Nature 296:3942 (1982)), etc. Any type of plasmid, cosmid, YAC, mini-circle or viral vector can be used to prepare the recombinant DNA construct that can be introduced directly into the tissue site. Alternatively, viral vectors can be used which selectively infect the desired tissue, in which case administration may be accomplished by another route (e.g., systematically).

Another approach utilizes a recombinant DNA construct in which the RNA or other aptamer-containing nucleic acid is placed under the control of a strong pol III or pol II promoter. The use of such a construct to transfect target cells in the patient will result in the transcription of sufficient amounts of the subject RNA. For example, a vector or expression construct can be introduced in vivo such that it is taken up by a target cell and directs the transcription of a subject RNA. Such a vector or expression construct can remain episomal or become chromosomally integrated, as long as it can be transcribed to produce the desired product. Such vectors can be constructed by recombinant DNA technology methods standard in the art.

Thus the invention also provides an expression vector or construct having a coding sequence that is transcribed to produce one or more transcriptional products that produce a subject RNA in the treated cells. Expression vectors appropriate for producing an aptamer-regulated nucleic acid are well-known in the art. For example, the expression vector is selected from an episomal expression vector, an integrative expression vector, and a viral expression vector.

In certain embodiments, the expression vector can be designed to include one or more subject RNA an RNA transcript, such as in the 3' untranslated region (3'-UTR), so as to regulate transcription, stability and/or translation of that RNA transcript in a manner dependent on the ligand. To further illustrate, the expression construct can include a coding sequence for a polypeptide such that the mRNA transcript includes both the polypeptide coding sequence as well as one or more of the RNA of the invention. In this way, expression of the polypeptide can be rendered dependent on the ligand(s) to which the aptamer(s) bind.

An aptamer, aptamer-regulated device, or polynucleotide described herein can be obtained using chemical synthesis, molecular cloning or recombinant methods, DNA or gene assembly methods, artificial gene synthesis, PCR, or any combination thereof. Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide comprising a desired sequence can be inserted into a suitable cloning or expression vector, and the cloning or expression vector in turn can be introduced into a suitable target cell for replication and amplification, as further discussed herein. Polynucleotides may be inserted into target cells by any means known in the art. Cells may be transformed by introducing an exogenous polynucleotide, for example, by direct uptake, endocytosis, transfection, F-mating, chemical transformation, or electroporation. Once introduced, the exogenous polynucleotide can be maintained within the cell as a non-integrated expression vector (such as a plasmid) or integrated into the target cell genome. The polynucleotide so amplified can be isolated from the target cell by methods well known within the art. Alternatively, PCR allows reproduction of DNA sequences.

RNA can be obtained by using the isolated DNA in an appropriate expression vector and inserting it into a suitable target cell. When the cell replicates and the DNA is transcribed into RNA, the RNA can then be isolated using methods well known to those of skill in the art. Alternatively, RNA can be obtained by transcribing the isolated DNA, for example, by an in vitro transcription reaction using an RNA polymerase. Alternatively, RNA can be obtained using chemical synthesis.

Suitable cloning vectors may be constructed according to standard techniques, or may be selected from a large number of cloning vectors available in the art. While the cloning vector selected may vary according to the target cell intended to be used, useful cloning vectors will generally have the ability to self-replicate, may possess a single target for a particular restriction endonuclease, and/or may carry genes for a marker that can be used in selecting clones containing the expression vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

In one aspect, the disclosure provides an expression vector comprising any of the aptamers, aptamer-regulated devices, or polynucleotides disclosed herein described herein. An aptamer, aptamer-regulated device, or polynucleotide disclosed herein may be located in an expression vector. An expression vector may be a construct, which is capable of delivering, and preferably expressing, one or more gene(s) or sequence(s) of interest in a target cell. Examples of expression vectors include, but are not limited to, viral vectors (e.g., adenoviruses, adeno-associated viruses, and retroviruses), naked DNA or RNA expression vectors, plasmids, cosmids, phage vectors, DNA or RNA expression vectors associated with cationic condensing agents, DNA or RNA expression vectors encapsulated in liposomes, and certain eukaryotic cells, such as producer cells. An expression vector may allow easy and efficient replication, cloning, and/or selection. Accordingly, an expression vector may additionally include nucleic acid sequences that permit it to replicate in the target cell, such as an origin of replication, one or more therapeutic genes and/or selectable marker genes and other genetic elements known in the art such as regulatory elements directing transcription, translation and/or secretion of the encoded protein. Expression vector components may generally include, but are not limited to, one or more of the following: a signal sequence; an origin of replication; one or more marker genes; and suitable transcriptional controlling elements (such as promoters, enhancers and terminator). For expression (e.g., translation), one or more translational controlling elements are also usually required, such as ribosome binding sites, translation initiation sites, internal ribosome entry site, and stop codons. The expression vector may be used to transduce, transform or infect a cell, thereby causing the cell to express nucleic acids and/or proteins other than those native to the cell. The expression vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such expression vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining cloning and expression vectors are well-known (see, e.g. Green and Sambrook, Molecular Cloning: A Laboratory Manual, 4th edition, Cold Spring Harbor Laboratory Press, New York (2012)).

In one aspect, the disclosure provides a target cell comprising any of the aptamers, aptamer-regulated devices, or polynucleotides described herein. In one aspect, the disclosure provides a target cell comprising any of the expression vectors described herein. Any target cell capable of overexpressing heterologous DNA can be used. Suitable target cells include, but are not limited to, mammalian (e.g., human such as HEK, HEK293, HEK293T, HeLa, U2OS, SK-MEL-28, A549, Colo 829, NCH89, Hep G2, Capan-1, T cell, B cell, or primary human $T_{CM}$; mouse such as a 3T3, CTLL-2, or cells derived from Swiss, BALB/c or NIH mice; hamster such as CHO; monkey such as COS or Vero), bacterial (e.g., *Escherichia coli, Bacillus subtilis, Pseudomonas, Streptomyces, A. baumannii, A. baylyi, A. tumefaciens, M. magneticum, M. smegmatis, S. pyogenes, M. tuberculosis, M. smegmatis, S. coelicolor, Francisella*), algae, cyanobacteria (e.g., *S. elongatus*), fungal (e.g., *Saccharomyces cerevisiae, Schizosaccharomyces pombe, Kluyveromyces lactis*), amphibian (e.g., *Xenopus laevis*), plant (e.g., *Arabidopsis*, Cucumber protoplast, *N. tabacum* chloroplasts), or insect (e.g., *Drosophila melanogaster*, High Five, *Spodoptera frugipedera* Sf9) target cells. A target cell may include, but is not limited to, a cell from a mammal, human, non-human mammal, domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof. In some cases, a target cell is from a human.

The target cells can be transfected, e.g. by conventional means such as electroporation with at least one expression vector of the disclosure. The expression vectors containing the polynucleotides of interest can be introduced into a target cell by any of a number of appropriate means, including electroporation, chemical transformation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the target cell. The transfected or transformed target cell may then be cultured under conditions that allow expression of the polynucleotide.

Formulations

The subject RNA or nucleic acids may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject RNA or nucleic acids can be provided in formulations also including penetration enhancers, carrier compounds and/or transfection agents.

Representative United States patents that teach the preparation of such uptake, distribution and/or absorption assisting formulations which can be adapted for delivery of the subject RNA or nucleic acid molecules include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The subject RNA or nucleic acids may also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to RNAs or nucleic acids and pharmaceutically acceptable salts, and other bioequivalents.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Preferred examples of pharmaceutically acceptable salts include but are not limited to (a) salts formed with cations such as sodium, potassium, lithium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Uses

The subject RNA or nucleic acids can further be used to engineer novel regulatory pathways and control loops for applications in metabolic engineering and synthetic circuit design by enabling a cell to sense and respond to folinic acid levels. Because the activity of the subject RNA or nucleic acids may be tunable over a range of ligand concentrations, the system can be designed to inhibit or activate genes only when certain triggering ligands have exceeded or gone below certain threshold concentrations. Balancing heterologous gene expression in biosynthetic pathways to maximize product yield can be achieved with the subject RNA or nucleic acids that regulate expression of any gene of interest in response to any pre-determined pathway intermediates, including any disease markers. Synthetic gene circuits have recently been used to understand and model cellular networks and to achieve cellular control as a step towards "programmable" cell behavior. Gene circuits can be built using combinations of the subject RNA or nucleic acids as regulators for precise control schemes. The subject RNA or nucleic acids are useful in building and characterizing circuits.

Finally, aptamer-regulated nucleic acids present tools for cellular imaging (by, for example, using a fluorescent reporter gene as the gene of interest), measuring, and detection strategies enabling programmable concentration-specific detection of ligands. The subject RNA or nucleic acids offer a unique platform to generate tailor-made cellular sensors and "smart" regulators that can target any gene in response to the ligand, creating new avenues for cellular control and engineering.

EXPERIMENTAL

Example 1

Programmable and Conditional Gene Control by a Clinical Drug

Natural biological systems rely on the ability to sense and respond to molecular and environmental stimuli through dynamic regulation of gene expression. Engineering synthetic biological systems similarly requires comparable sensing and control capabilities, particularly for effector ligands orthogonal to those found in nature or suitable for specialized applications such as clinical therapeutics. The construction of synthetic RNA regulatory switches responsive to the clinical drug folinic acid (leucovorin) is described herein. RNA aptamer sensors that bind with high specificity and affinity to either the (6R)- or (6S)-diastereomers of folinic acid were generated de novo through in vitro selection. Selection design principles were applied to favor discovery of high affinity aptamers that function under intracellular conditions, requiring as few as 21 nucleotides and with dissociation constants as low as 19.2 nM and ligand specificities up to 70,000-fold over structurally similar molecules. To engineer synthetic RNA switches that induce gene expression in vivo, a library of hammerhead ribozyme-based switches based on a transmitter strand displacement mechanism was designed and screened for functional gene regulatory activity in yeast. The successful construction of folinic acid-responsive switches demonstrates the in vivo application of these aptamers, which increases the number of orthogonal input signals available for inducible gene expression and provides a much needed clinically relevant ligand for advancing cellular and RNA-based therapeutics. This system combines design considerations, control parameters, and validation measurements to demonstrate a streamlined process for constructing RNA switches to desired molecular targets that can extend their use in varied synthetic biology applications.

A general and integrated process for generating inducible, RNA-based gene expression systems is described herein. A series of design principles, control parameters, and validation measurements were developed for the de novo, in vitro selection of RNA aptamer sensors that increase the likelihood of enriching and isolating binding sequences that function in vivo (FIG. 1). This system was applied to address a specific deficiency in available effector ligands, the lack of clinically relevant inducers, by selecting a set of aptamers that bind the clinical drug folinic acid. A recently reported surface plasmon resonance platform was used to validate and characterize aptamer binding and to rapidly prototype aptamer integration sites (Chang et al. (2014) Analytical Chemistry 86(7):3273-3278). Using a FACS-based screening method, a high affinity folinic acid aptamer was integrated into a hammerhead ribozyme through a randomized transmitter sequence and isolate functional switches that activate gene expression upon ligand induction (Liang et al. (2012) Nucleic Acids Research 40(20):e154). This work systematizes overall design principles for generating new biological sensing capabilities that function in vivo and provides an integrated process for generating and incorporating these sensing functions into genetically encoded, ligand-responsive, and gene-regulatory elements. These improvements in selection design and switch integration provide a more robust strategy for generating genetic switches to desired chemical targets for customizable inducible gene expression.

Materials and Methods

Figure 9:
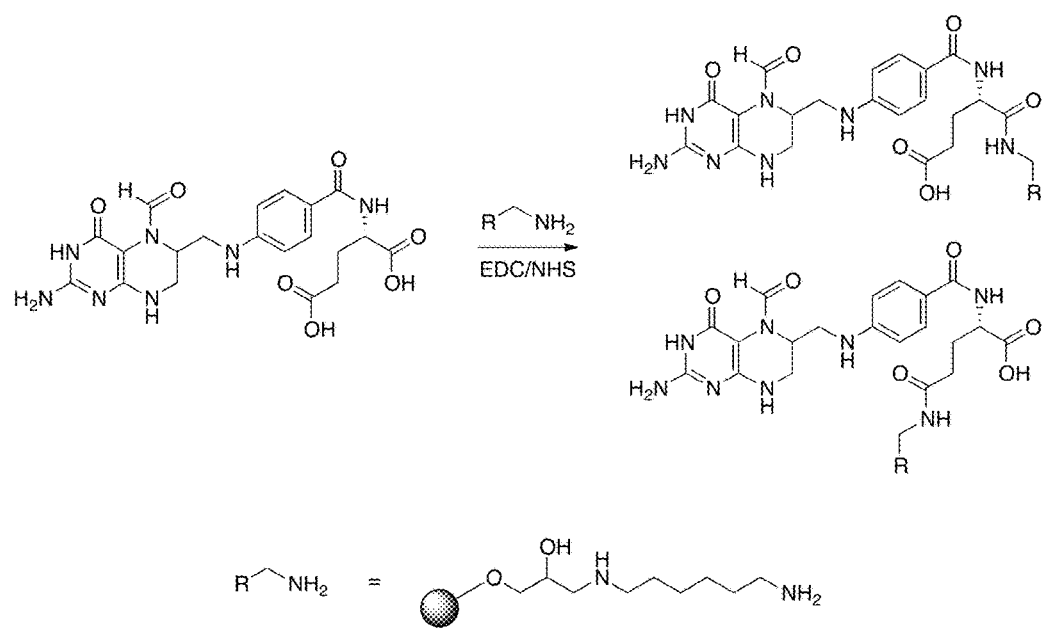
FIG. 9. Synthesis for coupling folinic acid to amino-modified solid support beads.

Selection column preparation. Positive selection columns functionalized with folinic acid and negative selection columns without folinic acid were prepared using EAH Sepharose 4B beads (GE Healthcare, Uppsala, Sweden). 0.5 mL beads per selection column were rinsed sequentially with water (pH 4.5) and 500 mM NaCl. For conjugation reaction, (6R,S)-Folinic acid (Sigma-Aldrich, St. Louis, Mo.) was coupled through its carboxylate groups to amino-functionalized beads using an amide bond-forming carbodiimide coupling reaction (FIG. 9). Rinsed beads were washed with conjugation buffer (0.1M MES, pH 6.0). N-hydroxysuccinimide (NHS, Thermo Scientific) and N-(3-dimethylaminopropyl)-N'-ethylcarbodiimide hydrochloride (EDC, Sigma-Aldrich) were dissolved in 0.5 mL conjugation buffer to final concentrations of 0.06 M and 0.1 M, respectively, supplemented with appropriate folinic acid concentration between 1 µM and 1 mM depending on selection round (FIG. 2), and added to rinsed beads for a total reaction volume of 1 mL per selection column. Reaction was mixed thoroughly and incubated at room temperature for 2 hours with rotation. Remaining amine functional groups on beads were subsequently reacted with acetate to block nonspecific electrostatic interactions between positively charged amine groups and negatively charged RNA backbone. Likewise, negative selection beads without folinic acid conjugated were also blocked with acetate for negative selections. For blocking reaction, folinic acid-conjugated beads or rinsed beads for positive and negative selection columns, respectively, were washed with blocking buffer (1 M acetate, pH 6.0) and reacted with NHS and EDC as described above but in the absence of folinic acid and with the replacement of conjugation buffer with blocking buffer. All aqueous solutions were prepared using water treated with 0.1% (v/v) diethyl pyrocarbonate (Sigma-Aldrich) to inactivate RNases. 0.5 mL of positive or negative selection beads were packed into 2 mL disposable polystyrene columns (Thermo Scientific) according to manufacturer's instructions, equilibrated with selection buffer (10 mM HEPES, 150 mM NaCl, pH 7.4, GE Healthcare, supplemented with 5 mM $MgCl_2$, Life Technologies, Carlsbad, Calif.), and stored at 4° C. until used.

Figure 7:
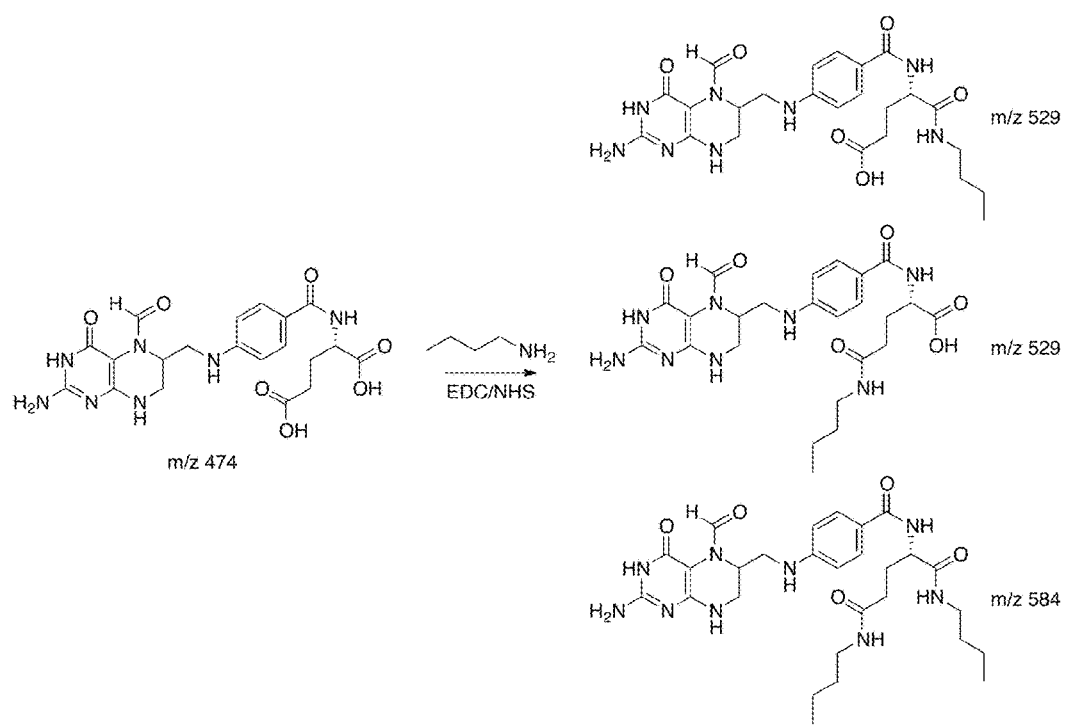
FIG. 7. Synthesis for coupling small molecule amines to folinic acid.

Validation and quantification of coupling reaction. Folinic acid conjugation was validated and quantified by liquid chromatography mass spectrometry (LC-MS). For conjugation validation, 5 mM folinic acid was coupled to 5 mM n-butylamine (Sigma-Aldrich) in conjugation buffer with 0.02 M NHS and 0.1 M EDC for 2 hours at room temperature, and 5 µL of the reaction mixture (diluted 50-fold) was separated on a Zorbax SB-Aq column (3.0×50 mm, 1.8 µM particle size) (Agilent Technologies). For conjugation quantification, beads from conjugation reactions were pelleted by centrifugation, and 5 µL of the reaction supernatant (diluted 10-fold for 1 mM folinic acid reactions) was separated on the Zorbax column. The column was equilibrated with water, 0.1% acetic acid, and 0.1% methanol (Solvent A), and samples were eluted with a mobile phase of methanol and 0.1% acetic acid (Solvent B) in the following sequence: 0-1 min. at 100% A, 1-4 min. 0-25% B, 4-7 min. at 25% B, followed by steps to clean the column with 100% B and re-equilibrate in A. The flow rate was held constant at 0.6 mL/min. Eluted reaction products were identified by UV absorbance at 274 nm or on an Agilent 6320 Ion Trap mass spectrometer. For validation, extracted ion chromatograms of major reaction products were consistent with masses of expected coupling products (FIG. 7, FIG. 8). For quantification, peak area of the UV or extracted ion chromatograms was integrated and compared to standard curve of folinic acid.

De novo, in vitro aptamer selection. Selection library N70 antisense template DNA oligonucleotide 5'-GTGTCCGC-CTATCTCGTCTC-CNNNNNNNNNNNNNNNNNNNNNNNNNNNNNNNN NNNNNN NNNNNNNNNNNNNNNNNNNNNNNNNNNNNNNN NNGGAAGGAGGCGGGCAGAAGTCCCT ATAGT-GAGTCGTATTAGAA (SEQ ID NO:1) was synthesized by Integrated DNA Technologies. Initial RNA library for first selection round covered ~1.2*$10^{15}$ unique sequences and was transcribed by annealing 2 µmol DNA template with 2.5 µmol primer N70-T7-fwd (5'-TTCTAATACGACTCAC-TATAGGGACTTCTGCCCGCCTCCTTCC) (SEQ ID NO:30) to form a partially double stranded template for run-off transcription using a MEGAshortscript T7 transcription kit (Life Technologies), supplemented with 0.5 µCi α-$^{32}$P-GTP (MP Biomedicals, Solon, Ohio), according to manufacturer's instructions. RNA libraries for subsequent selection rounds used double stranded DNA template generated from PCR amplification. Unincorporated nucleotides were removed using NucAway Spin Columns (Life Technologies), according to manufacturer's instructions. Purified RNA was resuspended in selection buffer, denatured at 65° C. for 5 min, and cooled to room temperature directly before use.

Figure 2:
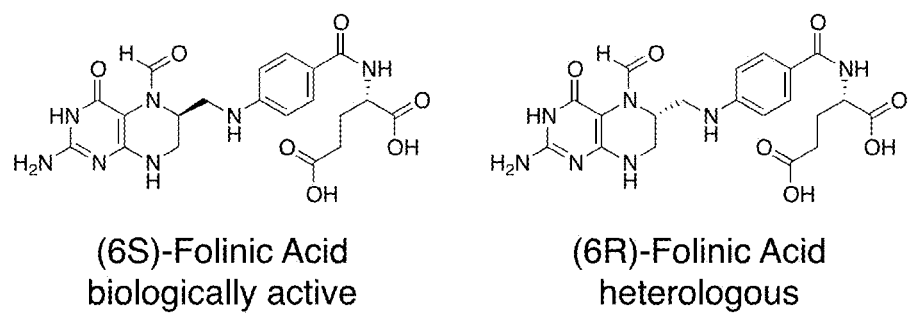
FIG. 2. Folinic acid as a clinical drug. Chemical structures of (6S)-Folinic Acid and (6R)-Folinic Acid.

Selection columns were equilibrated at room temperature with 5 mL selection buffer, supplemented with 10 pg/mL yeast tRNA (Ambion) to saturate nonspecific RNA binding sites. For selection rounds 1 and 2, RNA library was added to the positive selection column, which was then washed with appropriate volume of selection buffer supplemented with 10 pg/mL yeast tRNA (FIG. 2). For selection rounds 3-10, a negative selection column was inserted directly above the positive selection column to remove RNA sequences that bound to the beads. RNA library was added to the negative selection column, and the negative selection column was washed with 4 column volumes of selection buffer supplemented with 10 pg/mL yeast tRNA before being removed and remaining buffer washes (FIG. 2) applied to positive selection column.

Positive selection column was washed with 6 column volumes of selection buffer supplemented with appropriate folinic acid concentration (FIG. 2) to competitively elute bound RNAs off of column. Each wash and elution volume was collected separately, and the radiation intensity for each collected volume and selection column was measured using a ratemeter (Ludlum Measurements, Sweetwater, Tex.).

Elution volumes were pooled together, and RNA was concentrated using Amicon Ultra-0.5 Centrifugal Filter Units with Ultracel-10 membranes (EMD Millipore, Billerica, Mass.). Concentrated RNA was reverse transcribed using Superscript III Reverse Transcriptase (Life Technologies) with primer N70-rev according to manufacturer's instructions, and cDNA product was PCR amplified using primers N70-fwd-short and N70-rev. Unincorporated nucleotides were removed using NucAway Spin Columns. Purified PCR product was used as template for RNA transcription reaction for next selection round.

Individual sequences from selection rounds 6, 8, and 10 were isolated by PCR amplifying selection round libraries with primers GAP-N70-AvrII-fwd-short and GAP-N70-XhoI-rev and cloning into plasmid pCS1748 (1) via homologous recombination gap-repair transformation into yeast using standard lithium acetate heat shock to generate single colonies. Individual yeast colonies were incubated at 99° C. for 10 min in 20 mM NaOH to lyse cells, and 5 µL of mixture were used at template in PCR with primers CS653 and CS654. PCR product was purified using EconoSpin columns (Epoch) and sequenced using primer CS653 (Elim).

Full length sequences were amplified off of sequencing PCR products using primers N70-fwd-short and Biacore-N70-rev to append a poly(A) tail. Truncated or mutated sequences were synthesized by Integrated DNA Technologies or the Protein and Nucleic Acid facility (Stanford, Calif.).

Surface plasmon resonance characterization of aptamer binding properties. Nucleic acid aptamer preparation. RNA aptamers were prepared by PCR amplification of DNA template sequences (Table 4, Integrated DNA Technologies, Coralville, Iowa) using forward and reverse primers Biacore-fwd and Biacore-rev, respectively, followed by transcription of the PCR product using the MEGAshortscript T7 transcription kit (Life Technologies) and purification of the transcription product using the RNA Clean & Concentrator kit (Zymo Research, Irvine, Calif.), according to the manufacturers' instructions. Aptamers were resuspended in selection buffer, denatured at 65° C. for 5 min, and cooled to room temperature directly before use.

Sensor chip surface generation. Experiments were performed on a Biacore X100 instrument (GE Healthcare) at 25° C. A CM5 sensor chip (GE Healthcare) was equilibrated with HBS-N buffer. The DNA linker strand (5'-AmMC6-TTTTTTTTTTTTTTTTTTTTTTTT) (Integrated DNA Technologies) (SEQ ID NO:133), with an amino modified 6-carbon linker on the 5' end, was immobilized to the chip surface. The carboxymethylated dextran surface of the CM5 chip was activated for 7 min at a flow rate of 10 µL/min using a 1:1 volume ratio of 0.4 M 1-ethyl-3-(3-dimethylaminopropyl) carbodiimide (GE Healthcare) and 0.1 M N-hydroxysuccinimide (GE Healthcare). A molar ratio of 1:30 of DNA strand to hexadecyltrimethylammonium bromide (Sigma-Aldrich, St. Louis, Mo.) was diluted in 10 mM HEPES buffer (Sigma-Aldrich) to a final concentration of 20 µM and 0.6 mM, respectively, and injected over the activated surface for 10 min at a flow rate of 5 µL/min. Excess activated groups were blocked by an injection of 1 M ethanolamine (GE Healthcare), pH 8.5, for 7 min at a flow rate of 10 µL/min. The immobilization reaction was performed sequentially on both flow cells (FC1, FC2) and yielded approximately 4,000 RU of the DNA strand.

Aptamer binding assay. The Biacore X100 instrument was primed three times with running buffer prior to all binding assays. For each assay, three startup cycles were performed to stabilize the sensorgram baseline. For each startup cycle, the aptamer (~40-70 ng/µL, ~3 µM) was captured onto the sample flow cell (FC2) for 40 s at a flow rate of 5 µL/min. 25 mM NaOH (GE Healthcare) was injected for 30 s at a flow rate of 30 µL/min over both flow cells to regenerate the sensor surface. A dilution series of (6R)- or (6S)-folinic acid (Schircks Laboratories, Jona, Switzerland) was prepared in selection buffer and filtered through a 0.2 µm membrane (Pall Corporation, Port Washington, N.Y.). For each concentration sample, the aptamer was captured onto the sample flow cell (FC2) for 40 s at a flow rate of 5 µL/min, the folinic acid solution was injected over both flow cells at a flow rate of 30 µL/min to monitor target association, and selection buffer was injected over both flow cells at a flow rate of 30 µL/min to monitor target dissociation. Association and dissociation phase lengths used were chosen based on time needed to reach equilibrium. Aptamer and folinic acid were removed from the sensor surface by injecting 25 mM NaOH for 30 s at a flow rate of 30 µL/min over both flow cells.

Data processing and analysis were performed using Biacore X100 Evaluation Software version 2.0 (GE Healthcare). A double-referencing method was performed to process all datasets. Data from the sample flow cell (FC2) were referenced first by subtracting data from the reference flow cell (FC1) to correct for bulk refractive index changes, nonspecific binding, injection noise, matrix effects, and baseline drift. Reference-subtracted data (FC2–FC1) were double-referenced with a blank injection of running buffer to account for any systematic drift over the course of the injection. Double-referenced data were fit to a 1:1 binding model for kinetic analysis or steady-state affinity model for thermodynamic analysis. Reported values are the mean and standard deviation of at least three independent experiments.

Plasmid and strain construction. Standard molecular biology cloning techniques were used to construct all plasmids. DNA synthesis was performed by Integrated DNA Technologies (Coralville, Iowa) or the Protein and Nucleic Acid Facility (Stanford, Calif.). All enzymes, including restriction enzymes and ligases, were obtained through New England Biolabs (Ipswich, Mass.). Ligation products were electroporated with a GenePulser XCell (Bio-Rad, Hercules, Calif.) into an *E. coli* DH10B strain (Invitrogen, Carlsbad, Calif.), where cells harboring cloned plasmids were maintained in Luria-Bertani media containing 50 µg/mL ampicillin (EMD Chemicals, Philadelphia, Pa.). All cloned constructs were sequence verified by Elim Biopharmaceuticals (Hayward, Calif.).

The two-color screening plasmid pCS1748; single-color plasmids harboring GFP (pCS1585) and mCherry (pCS1749) for use as compensation controls; and no-color plasmid pCS4, containing no fluorescence reporter gene, was used as the negative-control construct. Ribozyme-based devices and appropriate controls were inserted into the 3' untranslated region (UTR) of yEGFP3 in pCS1748 through appropriate restriction endonuclease and ligation-mediated cloning. DNA fragments encoding the ribozyme-based devices and controls were PCR amplified using forward and reverse primers L1-2-fwd and L1-2-rev, respectively, and inserted into pCS1748 via the unique restriction sites AvrII and XhoI, which are located 3 nts downstream of the yEGFP3 stop codon. Cloned plasmids were transformed into the budding yeast *Saccharomyces cerevisiae* strain W303α (MAT α his3-11, 15 trp1-1 leu2-3 ura3-1 ade2-1) through a standard lithium acetate method. All yeast strains harboring cloned plasmids were maintained on synthetic complete media with a uracil dropout solution containing 2% dextrose (SC-URA) and grown at 30° C. All plasmids constructed in this study are summarized in Table 3.

Cell sorting screen for functional ligand-responsive RNA switches. Device libraries (FIG. 17) were amplified using forward and reverse primers GAP-L1-2-fwd and GAP-L1-2-rev, respectively. The library was inserted into pCS1748 through homologous recombination-mediated gap-repair during transformation into yeast strain W303. Briefly, an 800 µL library PCR reaction was performed with 160 µmol of each primer and 16 µmol of the library template. 8 µg of the plasmid pCS1748 was digested with AvrII and XhoI. The digested vector was combined with the library PCR product, extracted with phenol chloroform, and precipitated into a dry pellet with ethanol. A Tris-DTT buffer (2.5 M DTT, 1 M Tris, pH 8.0) was added to a 50 mL yeast culture ($OD_{600}$ 1.3-1.5) and incubated at 30° C. for 10-15 min. The yeast were pelleted, washed with chilled Buffer E (10 mM Tris, pH 7.5, 2 mM $MgCl_2$, 270 mM sucrose), and resuspended in Buffer E to a final volume of 300 µL The yeast mixture was directly added to the precipitated DNA pellet and 50 µL of the mixture was transferred to a chilled 2 mm gap cuvette for electroporation (540 V, 25 µF, 1000Ω). Following transformation, the cells were resuspended in 1 mL warmed YPD media and incubated at 30° C. for 1 hr. Multiple transformations (~5) were performed to cover the desired library diversity ($\sim 10^6$-$10^7$). Transformation efficiencies were determined by plating serial dilutions of the transformants, and transformed cells were propagated in SC-URA media for FACS.

Two-color FACS-based screen. Cells harboring the RNA device libraries and control constructs were washed, resuspended in FACS buffer (1% BSA in PBS), and stained with a DAPI viability dye (Invitrogen). The cell suspension was filtered through a 40 µm cell strainer (BD Systems, San Jose, Calif.) prior to analysis on a FACSAria II cell sorter (BD Systems). GFP was excited at 488 nm and measured with a splitter of 505 nm and bandpass filter of 525/50 nm. mCherry was excited at 532 nm and measured with a splitter of 600 nm and a bandpass filter of 610/20 nm. DAPI was excited at 355 nm and measured with a bandpass filter of 450/50 nm. A scatter gate was set based on the forward and side-scatter area of cells harboring the negative-control plasmid (pCS4) to exclude debris, followed by a DAPI-(–) viability gate to exclude dead cells in the DAPI-(+) gate from the analysis. Cells harboring the single-color control plasmids (pCS1585, pCS1749) were analyzed to compensate spillover from GFP to the mCherry detector. A general sorting strategy was followed in which cells harboring devices with targeted gene-regulatory activities were analyzed to set a sorting gate on a two-dimensional scatter plot that correlates GFP and mCherry fluorescence. Cells within this gate were collected into SC-URA media and propagated to sufficient density for further screening or analysis.

Device characterization through flow cytometry analysis. Enriched device libraries from FACS were grown overnight in SC-URA liquid media and then plated onto SC-URA solid medium. Individual colonies were screened and characterized for gene-regulatory activity of the devices based on flow cytometry analysis. The GFP fluorescence was measured on a MACSQuant VYB flow cytometer (Miltenyi Biotec, Bergisch Gladbach, Germany). DAPI was excited at 405 nm and measured with a filter of 450/50 nm. GFP was excited at 488 nm and measured with a filter of 525/50 nm. mCherry was excited at 561 nm and measured with a filter of 615/20 nm. Cells harboring the mCherry-only plasmid (pCS1749) were analyzed to measure cellular autofluorescence in the GFP channel. Gene-regulatory activities were reported as relative GFP expression levels and were determined as the median of the GFP fluorescence using FlowJo (Tree Star), and normalized to the median of the GFP fluorescence of a positive control (sTRSV Contl, a noncleaving sTRSV ribozyme with a scrambled core) that is grown under identical ligand conditions, run in the same experiment, and set to 100%.

Devices that exhibited desired activities were amplified by colony PCR using forward and reverse primers CS653 (5'-GGTCACAAATTGGAATACAACTATAACTCT)(SEQ ID NO:50) and CS654 (5'-CGGAATTAACCCT-CACTAAAGGG) (SEQ ID NO:51), respectively, and sequenced. The recovered devices were resynthesized and recloned into the vector backbone to confirm the observed activity. DNA oligos were synthesized and amplified for insertion into pCS1748 using forward and reverse primers L1-2-fwd and L1-2-rev, respectively. The resynthesized devices were inserted into pCS1748 via the unique restriction sites AvrII and XhoI. The reconstructed device plasmids were transformed into the W303 yeast strain through a standard lithium acetate method. Cells harboring the selected devices and appropriate controls were prepared as described above for the sorting experiments and analyzed to characterize the gene-regulatory activity of each device. FlowJo was used to process all flow cytometry data. Gene-regulatory activities in the absence or presence of ligand were determined as the median of the GFP fluorescence based, and normalized to the median of the GFP fluorescence of a positive control (sTRSV Contl, a noncleaving sTRSV ribozyme with a scrambled core) in the absence or presence of ligand, respectively, to correct for any nonspecific effects of ligand on the measured fluorescence (FIG. 19). Reported gene-regulatory activities are the mean and standard deviation of at least three independent experiments.

Results and Discussion

De Novo, In Vitro Selection Enriches RNA Aptamer Sensors to Folinic Acid.

A distinct limitation in the implementation of synthetic RNA regulatory switches is the lack of clinically relevant small molecule ligands that are nontoxic and readily bioavailable and display favorable pharmacokinetic properties. The lack of clinically suitable effectors restricts the development of genetically controlled cellular therapeutics and limits potential animal or human studies. For instance, theophylline-responsive switches have been implemented in proof-of-concept studies for regulating T cell proliferation for adoptive transfer therapy and viral replication and infectivity for gene therapy, cancer treatment, or vaccine development. However, its toxicity and narrow therapeutic index make theophylline unsuitable for clinical use.

One promising candidate for clinical use is the folate derivative folinic acid (FIG. 2), which is used in cancer treatment in combination with the antimetabolite chemotherapy drugs methotrexate and 5-fluorouracil and is naturally occurring. While only its (6S) form is biologically active, folinic acid is chemically synthesized as a mixture of two diastereomeric isomers, (6S)- and (6R)-folinic acid, and is approved for clinical use either as the diastereomeric mixture leuocovorin or as the single (6S) diastereomer levoleucovorin. As (6R)-folinic acid is heterologous and not biologically active, it is metabolized slower, extending its plasma half-life and concentration up to 15-fold and 18-fold, respectively, compared to the (6S) diastereomer. The low toxicity and biological stability of (6R)-folinic acid make it a clinically suitable orthogonal input signal for RNA-based therapies. In addition, the chemical functional groups present within folinic acid are amenable for covalent coupling to column-based chromatographic separation methods commonly used for in vitro selection (FIG. 2).

A continuous N70 randomized region was chosen as the basis for the selection library to provide sufficient sequence diversity and length as many previously validated in vitro selected, small molecule binding aptamers range in length from ~30-60 nucleotides. Previous studies have suggested N70 as being a particularly favorable length that increases the frequency that a given motif could occur while avoiding potential inhibitory effects of excess sequence that could interfere with proper folding of a functional sequence, and more compact sequences are preferred for engineering synthetic switches. Constant regions flanking the randomized region were included as primer binding sites for RNA transcription, reverse transcription, and PCR amplification and reproduced from a previous study (29). The initial RNA library pool of $1.2 \times 10^{15}$ unique sequences was generated through run-off transcription to prevent PCR amplification bias.

With the desired goal of functioning intracellularly, selection conditions were chosen to mimic physiological environments, with pH of 7.4 and moderate divalent magnesium concentration of 5 mM that would promote RNA folding and binding. The selection buffer was limited to only four components, $Na^+$, $Mg^{2+}$, $Cl^-$, and HEPES, to minimize binding dependence on the presence of a particular buffer component and to maintain consistent selection and characterization conditions.

Figure 3:
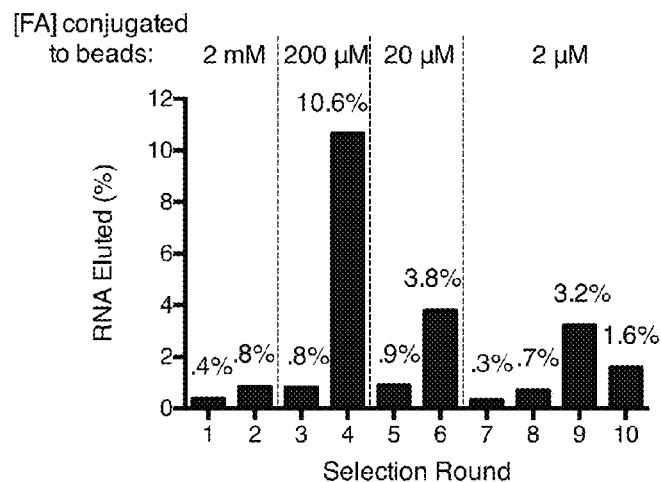
FIG. 3. Controlling selection stringency during de novo, in vitro selection of folinic acid-binding RNA aptamers. Binding enrichment of RNA library to folinic acid-derivatized column over course of selection is observed through monitoring fraction of $^{32}$P-radiolabeled RNA library that binds to column and is specifically eluted off column. Concentration of folinic acid conjugated onto column is decreased by 10-fold every other round to increase selection stringency.
Figure 4A:
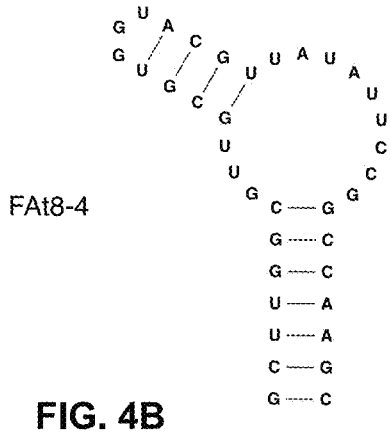
FIG. 4A-4H. Predicted secondary structures of truncated aptamer sequences characterized and corresponding surface plasmon resonance sensorgrams for (6R)-folinic acid and (6S)-folinic acid binding.
Figure 4A:
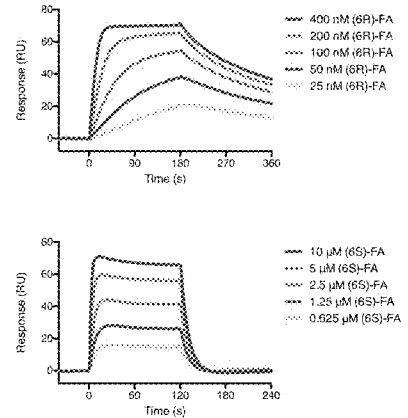
Figure 4B:
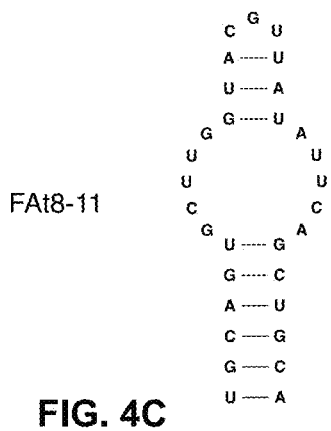
Figure 4B:
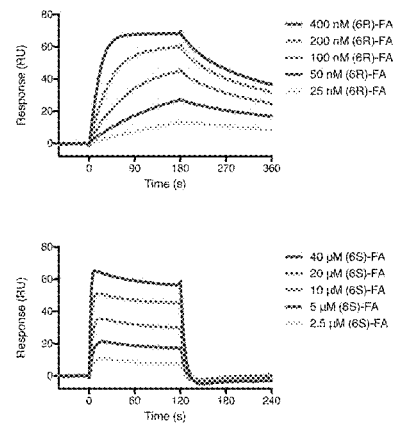
Figure 4C:
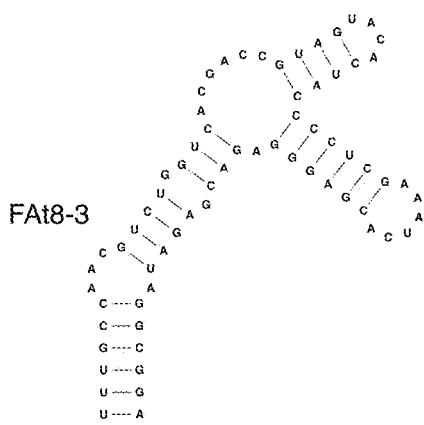
Figure 4C:
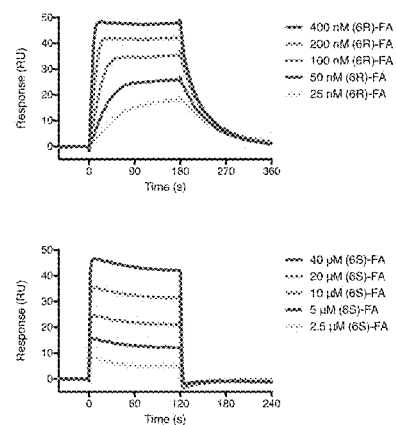
Figure 4D:
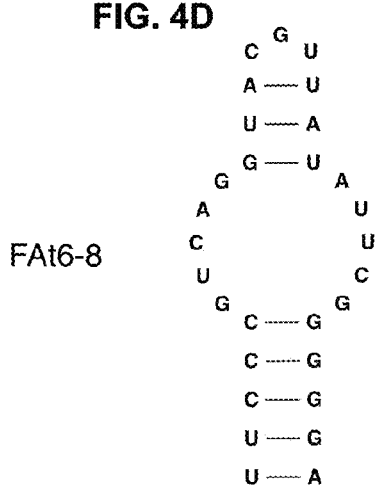
Figure 4D:
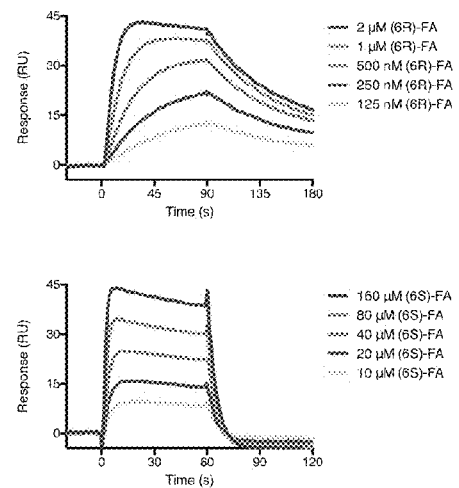
Figure 4E:
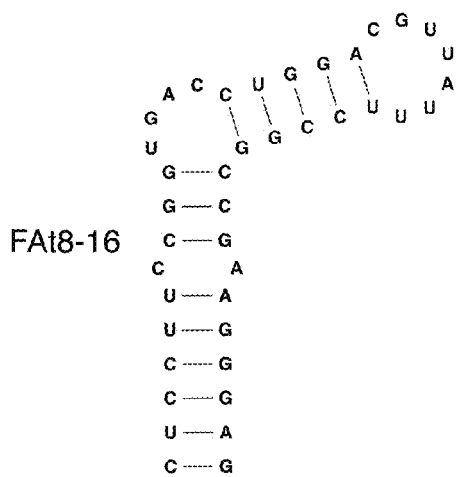
Figure 4E:
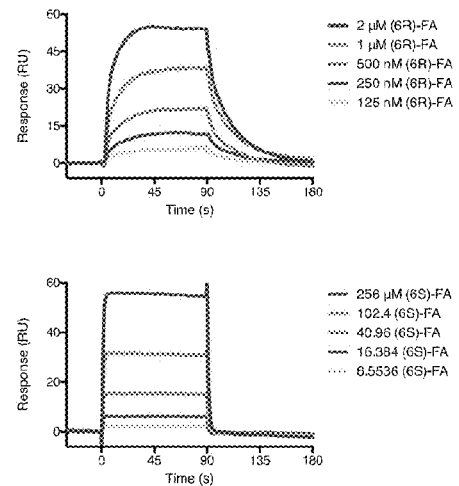
Figure 4F:
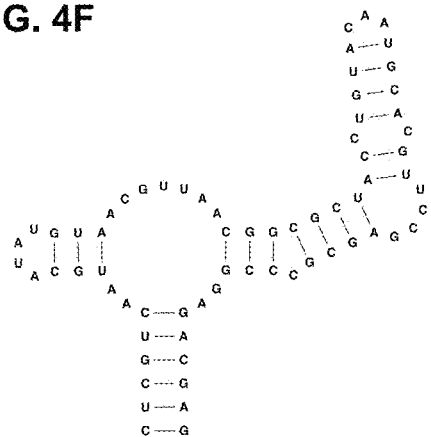
Figure 4F:
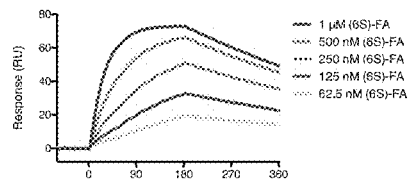
Figure 4F:
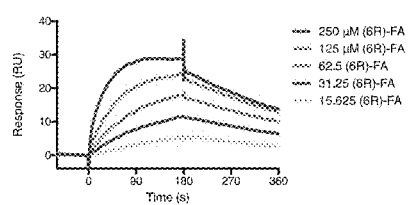
Figure 4G:
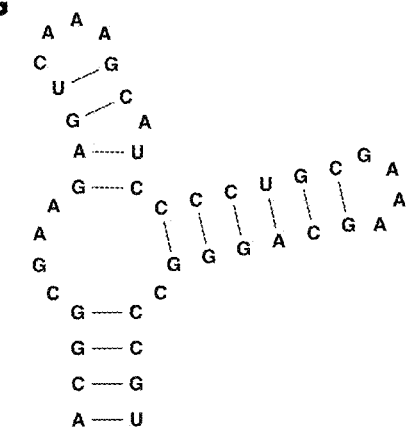
Figure 4G:
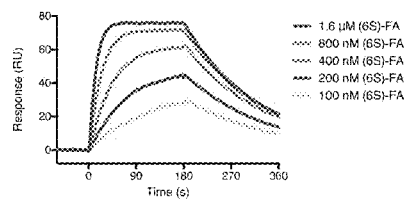
Figure 4G:
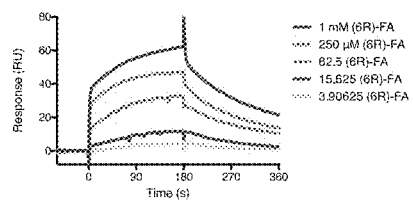
Figure 4H:
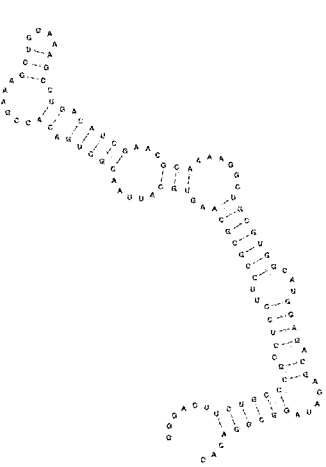
Figure 4H:
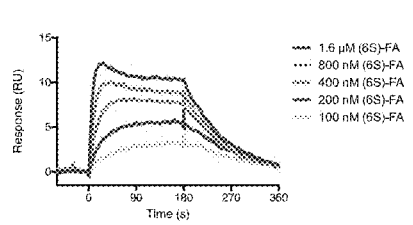
Figure 4H:
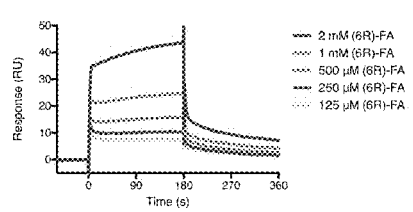
Figure 11:
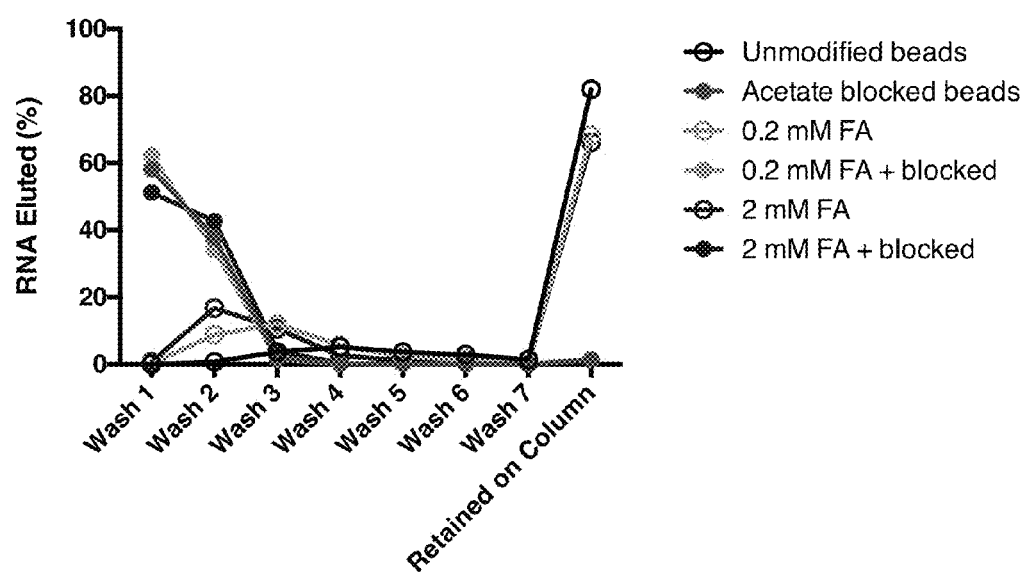
FIG. 11. Selection column RNA retention assay. RNA library was run through derivatized and non-derivatized amino-functionalized Sepharose EAH beads to determine optimal immobilization procedure to minimize nonspecific binding between RNA and beads. Unmodified beads showed high retention of RNA (~82% of input RNA) after washing with 7 column volumes of selection buffer, while blocking beads with acetate significantly reduced nonspecific binding of RNA onto column to 1.46%. Similarly, incomplete derivitization of amino groups on beads with folinic acid (either 0.2 mM FA or 2 mM FA), yielded retention of ~⅔ of input RNA onto column after washing (manufacturer states 7-12 mM amino groups on beads). However, performing an additional acetate blocking reaction directly after folinic acid immobilization reaction decreased RNA retention to 1.3-1.4%. Nonspecific binding between RNA library and beads is due to electrostatic attraction between positively charged amino group at selection buffer pH 7.4 and negatively charged phosphate nucleic acid backbone.

A recent aptamer selection meta-analysis observed correlation between selection immobilization concentration used during in vitro selection and resulting aptamer binding affinities, with aptamers with dissociation constants under 1 µM having immobilization concentrations of ~400-500 µM. A sub-micromolar binding affinity was targeted for in vivo applications, with a preferred goal of under 100 nM. Most in vitro selections use a constant immobilization concentration throughout the selection process. High concentrations of immobilized ligand decrease the chance that functional binders will be lost but generally yield lower affinity aptamers; low concentrations of immobilized ligand increase the chance that binding sequences will be lost before they can be enriched but yield higher affinity aptamers. A high concentration of immobilized ligand (2 mM) was used at the start to provide more available ligand for the initial RNA library to bind to and to prevent being too stringent initially and losing rare sequences but to steadily decrease immobilization concentration down to 2 µM to favor high affinity binders over weakly binding sequences (FIG. 3, Table 3). Chemical coupling to an amino-functionalized Sepharose bead support in immobilization reactions was validated and its yield quantified as ~95%; importantly, this yield was consistently observed regardless of ligand concentration, enabling the resulting concentration of immobilized ligand to be confidently adjusted based on reaction ligand concentration (FIG. 7, FIG. 8, FIG. 10, FIG. 9). Unreacted bead amine groups were blocked with acetate to prevent nonspecific binding of RNA to the column (FIG. 11). Elution concentrations of free ligand were also decreased throughout the course of the selection to minimize any possible effect of high concentrations of ligand counter ion ($Ca^{2+}$ for the folinic acid used) on aiding nonspecific RNA elution while remaining at least 12.5-fold higher than immobilization concentrations to out-compete off binders from column (FIG. 3, Table 3). A similar strategy could be used to decrease $Mg^{2+}$ dependence gradually throughout the selection but was not implemented in this case, as selection for high affinity has been posited to subsequently result in decreased magnesium dependence.

Selection stringency was controlled through multiple parameters and steadily increased throughout the selection rounds. 2 mM folinic acid was conjugated onto the column beads, and the concentration of immobilized ligand was decreased 10-fold every other round, reaching 2 µM folinic acid on the beads by round 7 and held constant through round 10. Wash volume was increased progressively from 6 column volumes in round 1, by an additional 3 column volumes each round (FIG. 3, Table 3). High transcription yields encouraged competition among RNA sequences for fewer binding sites.

Binding enrichment, as measured by percentage of RNA eluted, generally increased among successive rounds when ligand immobilization concentration on beads was held constant and dropped when ligand concentration decreased (FIG. 3, Table 3). Negative selections against a non-derivatized column were included starting in round 3 to prevent enrichment of RNA binding to the Sepharose bead support, which is a general problem encountered for chromatography-based affinity methods (FIG. 3). By constantly applying negative selective pressure against Sepharose binding, the percentage of RNA remaining on the negative selection column remained under 1% for the course of the selection (Table 3); in contrast, in the absence of negative selection, enrichment of RNA binders to the bead support was observed, emphasizing the importance of selecting against this alternative and undesired binding solution.

Aptamer Screening and Truncation Using Surface Plasmon Resonance Isolates Unique Functional Sequences.

Figure 12A:
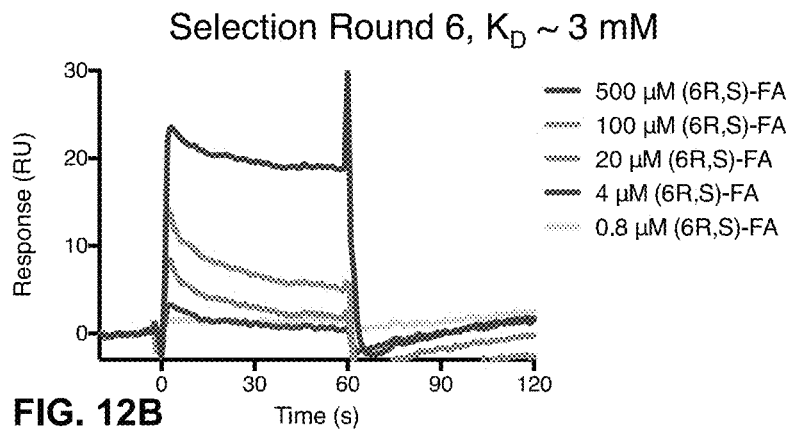
FIG. 12A-12C. In vitro selection enriches for high affinity sequences that bind folinic acid. Approximate dissociation constant ($K_D$) values are for (6R,S)-folinic acid.
Figure 12B:
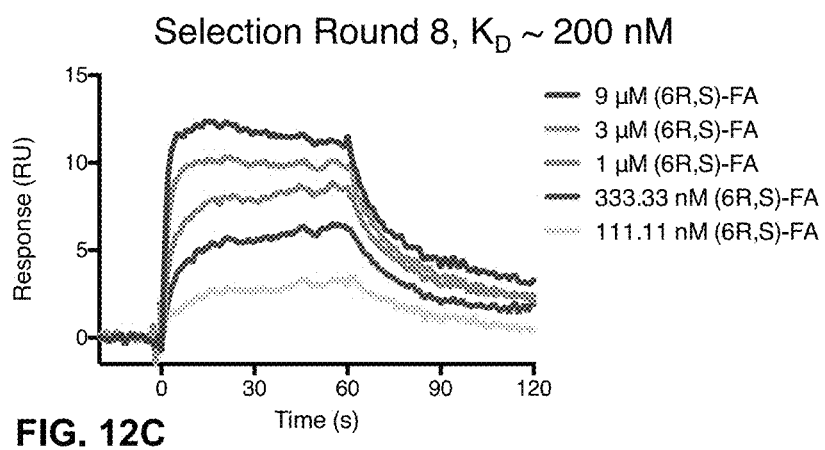
Figure 12C:
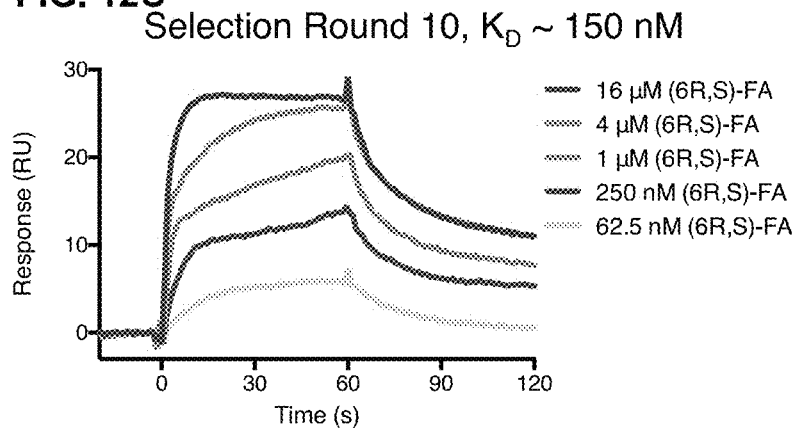
Figure 13A:
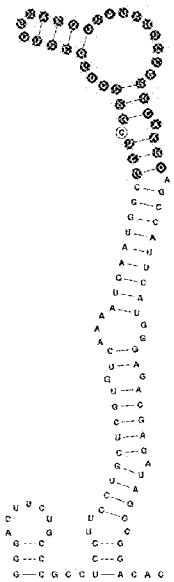
FIG. 13A-13H. Truncation of folinic acid aptamers from full-length sequences isolated from in vitro selection. Predicted secondary structures of full-length sequences are shown, with nucleotides in characterized truncated sequences shown in blue. Of particular interest are truncated sequences for aptamers FA8-18 and FA10-7, which fold into predicted secondary structures not present in lowest energy predicted secondary structure of full-length sequence.
Figure 13B:
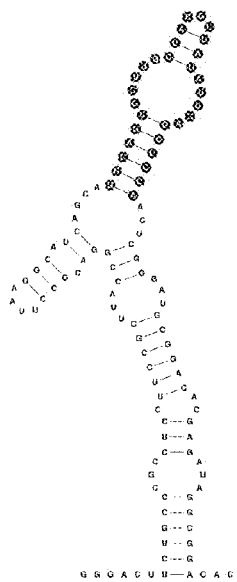
Figure 13C:
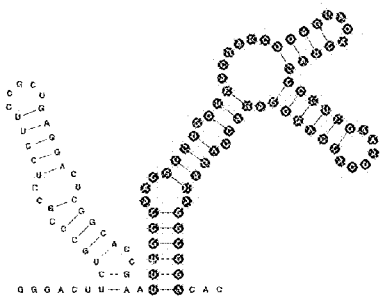
Figure 13D:
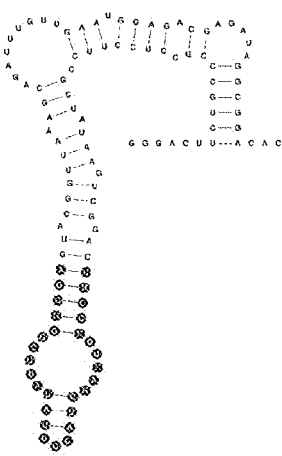
Figure 13E:
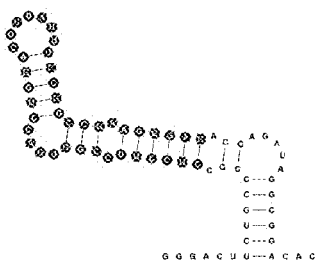
Figure 13F:
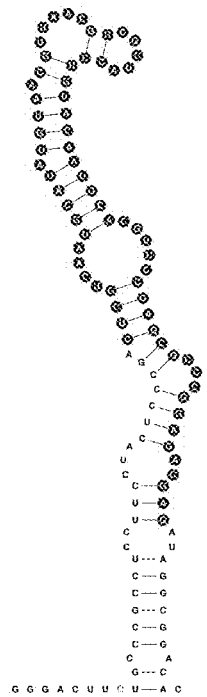
Figure 13G:
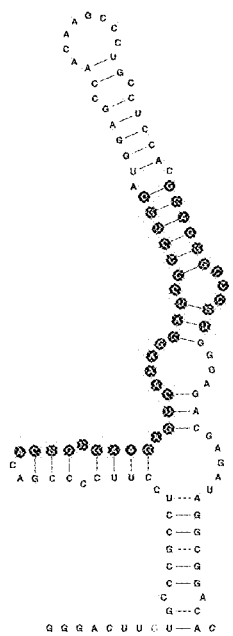
Figure 13H:
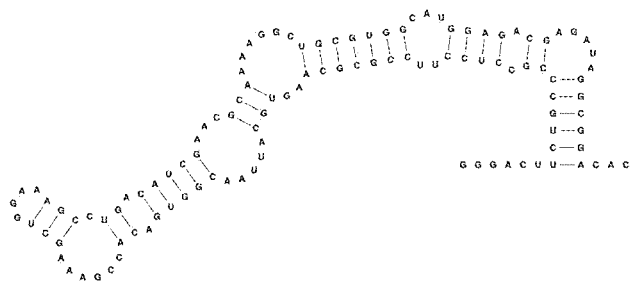
Figure 15:
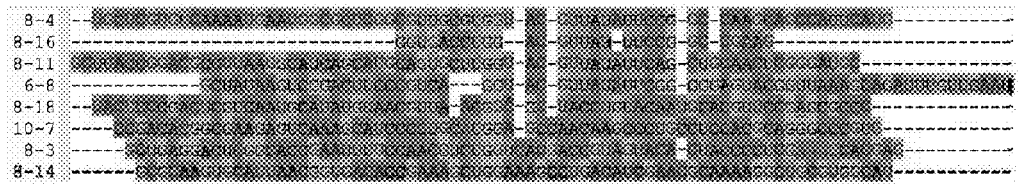
FIG. 15. Sequence alignment of folinic acid aptamers. Randomized regions of full-length sequences (omitting constant primer-binding regions) were aligned using ClustalX. Aptamers FA8-4, FA8-16, FA8-11, and FA6-8 share a consensus sequence motif, while other aptamers do not share homology with one another. Sequences from Top to Bottom: SEQ ID NOs:90-97.

After 10 rounds of in vitro selection, binding of the library pool to a column derivatized with folinic acid was observed (FIG. 3, Table 3). Bulk binding of the library pools from rounds 8, 9, and 10 was confirmed by using a label-free, surface plasmon resonance (SPR)-based aptamer characterization platform (FIG. 12). Individual library sequences were isolated and sequenced after cloning into a sequencing plasmid in a yeast host by homologous recombination. Individual sequences were then amplified from sequencing plasmids, transcribed into RNA, and screened by SPR for binding and specificity. Aptamer sequences were truncated to identify minimal sequences necessary for ligand binding and predicted, functional secondary structures (FIG. 4, FIG. 13). Rational truncations based off of predicted secondary structures were tested by truncating sequences where stable stems formed (e.g., aptamers FAt8-4, FAt8-11, and FAt8-3). Sequence alignment identified homology among aptamers FA8-4, FA8-11, FA6-8, and FA8-16 with the shared consensus motif 5'-GG(U)ACGUUAU(A)UUCNG (SEQ ID NO:134), where N is any nucleotide and nucleotides in parentheses are optional, that aided in truncating these aptamers (FIG. 15).

For aptamers where rational truncations did not produce functional binders, serial truncations were performed where 5 to 10 nucleotides were systematically removed from either the 5' or 3' ends. However, systematic truncations often produced false negatives, where sequences that contained the final truncated aptamer, and therefore would be expected to be capable of binding, displayed no binding, presumably due to improper folding. Exploring suboptimal predicted secondary structures revealed alternative folding structures that were tested to reveal functional aptamer conformations (FIG. 13). For instance, proper folding of the minimal FAt10-7 aptamer is disfavored in the full-length sequence by 2.3 kcal/mol and is the twelfth lowest energy predicted structure (−41.8 kcal/mol for the lowest energy predicted structure vs. −39.5 kcal/mol for the functional conformation). Likewise, proper folding of the minimal FAt8-18 aptamer is disfavored in the full-length sequence by 2.2 kcal/mol and is the twenty-fifth lowest energy predicted structure (−29.5 kcal/mol for the lowest energy predicted structure vs. −27.3 kcal/mol for the functional conformation). These predicted energies suggest that folinic acid binding may contribute at least 2.2 kcal/mol to stabilize these suboptimal folding conformations. Of eight aptamers characterized, only one, FA8-14, resisted truncation attempts; while a truncated sequence FAt8-14 maintains binding, it displays a unconventional binding response that cannot be fit to a 1:1 binding model (FIG. 14).

Characterization of Aptamer Kinetic and Equilibrium Binding Properties Observes High Aptamer Affinity and Specificity.

Binding properties of truncated aptamer sequences to both (6R)- and (6S)-folinic acid were characterized using a label-free, surface plasmon resonance-based method (FIG. 4, Table 1). Aptamers demonstrated high affinity and specificity, with dissociation constants ($K_D$s) as low as 19.2 nM and greater than 70,000-fold selectivity between the two folinic acid diastereomers. All aptamers displayed selectivity of at least 260-fold, and aptamers with $K_D$s below 65 nM were identified for both diastereomers. No aptamers were identified with similar affinities for both folinic acid diastereomers, likely a consequence from selective pressure for high affinity binders. Importantly, the $K_D$s exhibited are significantly below concentrations of the drug that can accumulate in human blood plasma through intravenous infusion, up to 77.6 µM for (6R)-folinic acid and 7.95 µM for (6S)-folinic acid, indicating that these aptamers should be sufficiently sensitive to operate within the human body for cellular and therapeutic applications.

Figure 16:
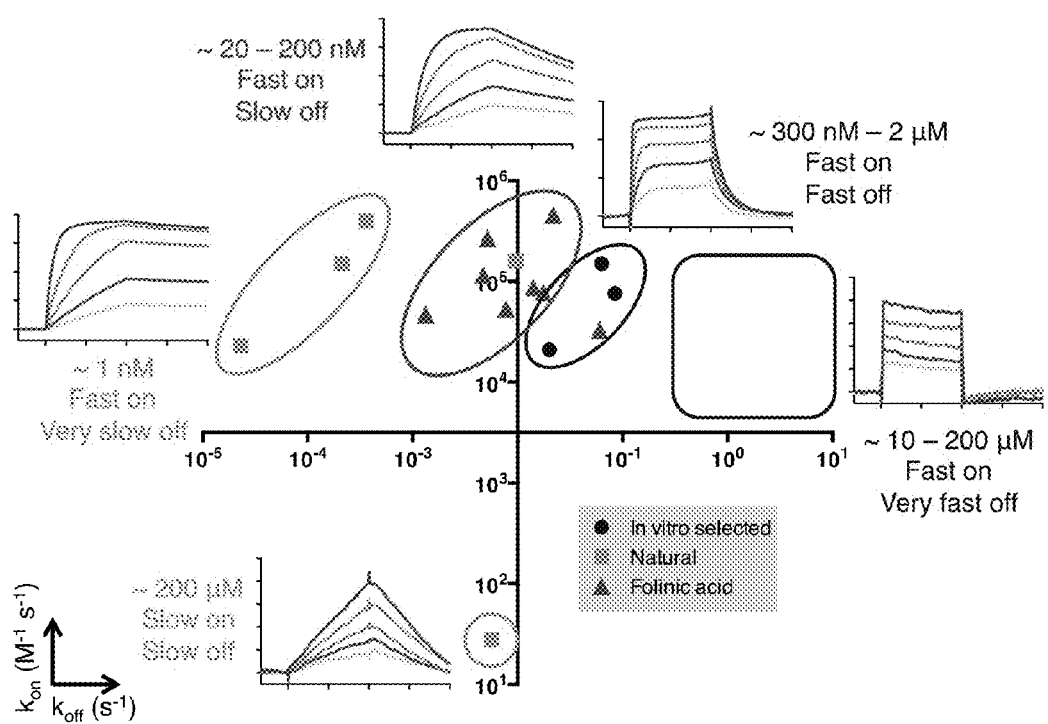
FIG. 16. Comparison of aptamer kinetic properties. In vitro selected aptamers for folinic acid exhibit $k_{on}$ rates among the fastest of characterized aptamers and $k_{off}$ rates slower than most in vitro selected aptamers characterized and within range observed for natural aptamers. In vitro selected and natural aptamer data reproduced from reference (2) and include natural aptamers for glycine, c-di-GMP class I, c-di-GMP class II, TPP Thi1, and TPP thiM and in vitro selected aptamers for theophylline, malachite green, flavin mononucleotide, arginine, citrulline, tyrosine, and ATP. Range of kinetic values for arginine, citrulline, tyrosine, and ATP aptamers are estimated based on instrument specifications and measured equilibrium dissociation constants. Representative aptamer sensorgrams shown, clockwise from bottom left: glycine, TPP Thi1, folinic acid FA8-18, theophylline, and ATP. All kinetic binding values were determined under identical conditions: 10 mM HEPES, 150 mM NaCl, 5 mM $MgCl_2$, pH 7.4, 25° C.

Folinic acid aptamers exhibit $k_{on}$ rates among the fastest of characterized natural or in vitro selected aptamers, $k_{off}$ rates slower than most in vitro selected aptamers characterized and within the range observed for natural aptamers, and $K_D$ values below most in vitro selected aptamers characterized and within the range observed for natural aptamers (FIG. 16). The slower $k_{off}$ rates exhibited by the folinic acid aptamers compared to other in vitro selected aptamers may be a consequence of the increasing selection stringency applied through extended buffer washing over the course of the selection. Through controlling selection stringency, aptamers with high affinity and specificity can be generated. Functional validation of their binding increases the confidence that these aptamers are capable of functioning in vivo.

TABLE 1

Kinetic and equilibrium binding properties of aptamers for (6R)- and (6S)-folinic acid.

| | Aptamer | (6R)-Folinic Acid | | | (6S)-Folinic Acid | | | Selectivity |
|---|---|---|---|---|---|---|---|---|
| | | $k_a$ (M$^{-1}$s$^{-1}$) | $k_d$ (s$^{-1}$) | $K_D$ (M) | $k_a$ (M$^{-1}$s$^{-1}$) | $k_d$ (s$^{-1}$) | $K_D$ (M) | |
| (6R)-FA specific | tFA8-4 | 2.69E+05 | 5.15E−03 | 1.92E−08 | 2.11E+04 | 1.05E−01 | 4.98E−06 | 260 |
| | tFA8-11 | 1.16E+05 | 4.68E−03 | 4.05E−08 | 6.56E+03 | 2.27E−01 | 3.46E−05 | 855 |
| | tFA8-3 | 4.59E+05 | 2.17E−02 | 4.73E−08 | — | — | 2.86E−05 | 606 |
| | tFA6-8 | 7.79E+04 | 1.76E−02 | 2.25E−07 | 2.33E+03 | 2.97E−01 | 1.28E−04 | 567 |
| | tFA8-16 | 3.30E+04 | 6.02E−02 | 1.82E−06 | 6.82E+02 | 8.50E−01 | 1.25E−03 | 684 |
| (6S)-FA specific | tFA8-18 | 9.40E+01 | 3.55E−03 | 3.77E−05 | 3.61E+04 | 2.27E−03 | 6.28E−08 | 600 |
| | tFA10-7 | — | — | 7.44E−05 | 5.36E+04 | 7.75E−03 | 1.44E−07 | 515 |
| | tFA8-14 | — | — | 1.02E−02 | 8.92E+04 | 1.28E−02 | 1.44E−07 | 71,100 |

TABLE 2

Equilibrium binding properties of aptamers for folate derivatives.

| Aptamer | Tetrahydrofolic acid (THF) $K_D$ (M) | (6R)-Tetrahydro-biopterin (THB) $K_D$ (M) | Dihydrofolic acid (DHF) $K_D$ (M) |
|---|---|---|---|
| tFA8-4 | (1.7-2.5)E−06 | N.D. | (2.6-6.6)E−06 |
| tFA8-11 | (1.4-3.3)E−06 | N.D. | (7.2-19.7)E−06 |
| tFA8-3 | (2.2-2.6)E−06 | 1.6E−06 | (1.1-3.5)E−06 |
| tFA8-18 | N.D. | N.D. | N.D. |

N.D. refers to non-detectable levels of binding at conditions tested.

Aptamer Sequence-Activity Relationships Identify Suitable Switch Integration Site.

Aptamer mutations were studied to assess their effect on ligand binding to better understand which nucleotides were involved in or necessary for binding and to identify sequence flexibility that could be leveraged during switch design. In particular, integration into regulatory switch platforms generally requires one or more stems through which to couple the aptamer to the actuator. Thus, identifying potential integration stems whose sequence can be modified for facile switch integration while not affecting ligand binding is a critical step in switch design. Two predicted stems in the FAt8-4 truncated aptamer, the highest affinity (6R)-specific aptamer identified, were assayed for sequence flexibility by shuffling nucleotide identify (A to C, C to A, G to U, and U to G to maintain U-G base pairing) (FIG. 17). If shuffled stem sequences retained binding ability, stems were labeled as sequence unconstrained without testing all six possible base pairs (i.e., A-U, U-A, C-G, G-C, U-G, G-U). Interestingly, one stem maintained binding even after shuffling all nucleotides, while extension of the other stem abolished binding activity. The sequence flexibility of the former stem provides a suitable integration point for incorporation into regulatory switch platforms, including translation, splicing, RNA stability, and RNA interference-based mechanisms. The sequence constraints of the latter stem suggest that either the predicted secondary structure is incorrect or that the terminal stem loop is involved in binding or folding (FIG. 17). Homology also indicates that this sequence is conserved among multiple selected aptamers, consistent with its loss of activity when modified (FIG. 15).

With the identity of at most 23 nucleotides fixed, the FAt8-4 aptamer encodes extraordinarily high ligand affinity and specificity in a short, compact sequence. A means for quantifying and comparing the binding capacities of different aptamers is calculated through their information content, defined as the amount of information (i.e., bits) necessary to specify the identity of each nucleotide position. A simple measure of information content adds two bits of information for invariant positions, one bit for two-base varying positions such as base-paired nucleotides, and zero bits for unconstrained four-base varying positions. Thus, the information content of FAt8-4 has an upper limit of approximately 60 bits (23 invariant positions and 14 base-paired positions), with fewer base pairs likely required to stabilize the stem and possibly other positions that may not be entirely invariant. Compared to other characterized aptamers, the information content necessary to encode folinic acid binding is consistent with the few other high-affinity aptamers analyzed.

Ribozyme-Based Switch Transmitter Screen in Yeast.

Synthetic ribozyme-based switches have been shown to regulate gene expression in a dose-dependent and reversible manner and exhibit a number of key properties: scalability, with their modular architecture allowing interchangeable sensor and gene choice for programmable ligand input-gene output combinations; tunability, with tunable gene-regulatory activities and directionality with switches either increasing or decreasing gene expression in the presence of input ligand; and portability, with switches demonstrated in vitro and in viral, bacterial, fungal, and mammalian systems.

Figure 6A:
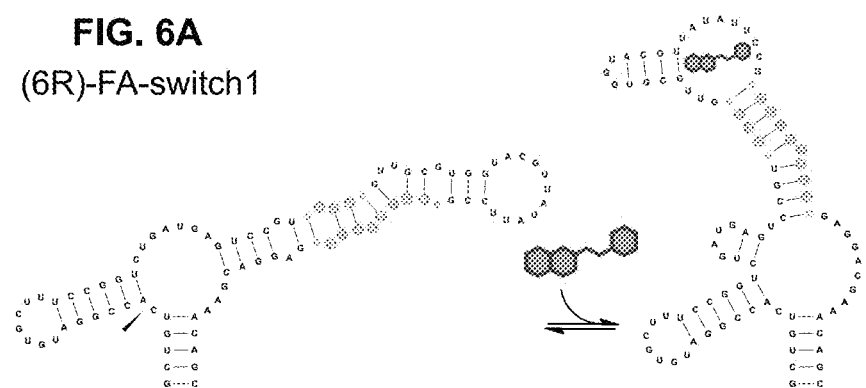
FIG. 6A-6C. Folinic acid-responsive switches isolated from transmitter screen regulate gene expression in vivo.
Figure 6B:
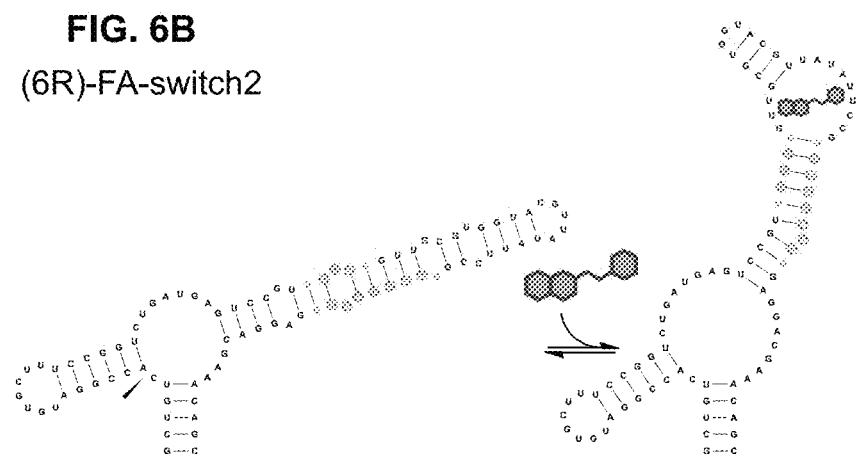
Figure 6C:
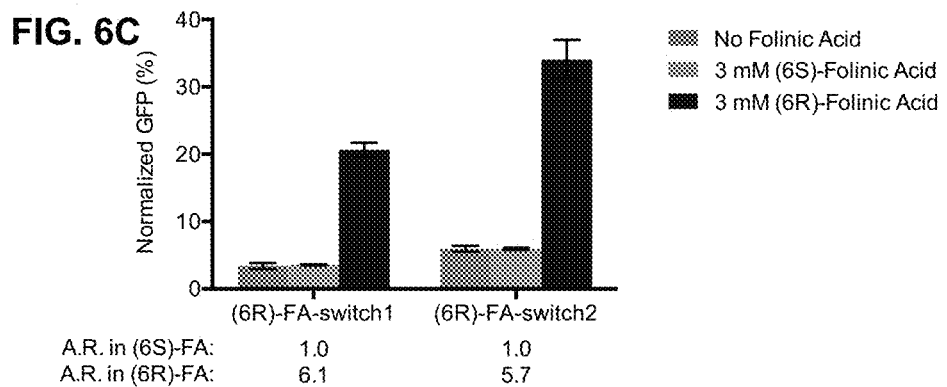

A transmitter library was screened for functional switches in Saccharomyces cerevisiae. An N11 transmitter library with 4.2 million device variants was generated by randomizing 11 out of 15 positions in a transmitter component joining the folinic acid aptamer FAt8-4 to the sTRSV hammerhead ribozyme (FIG. 5a, FIG. 6). The first base pair on either end of the transmitter was conserved from the FAt8-4 aptamer stem or from parent theophylline-responsive L2b8 switch, respectively. The FAt8-4 aptamer was chosen due to its highest affinity among selected (6R)-specific folinic acid aptamers. Five sorts were performed (FIG. 5c), alternating between the absence and presence of 10 mM (6R,S)-folinic acid and using theophylline-responsive L2b8 in the absence (~10.8% normalized GFP expression) and presence (~36.7% normalized GFP expression) of 5 mM theophylline, respectively, as the sorting collection gates (FIG. 5b).

Screening of isolated cells yielded folinic acid-responsive switches with activation ratios up to 6.1-fold in 3 mM (6R)-folinic acid (FIG. 6), demonstrating aptamer activity in vivo. These switches maintain ligand specificity for (6R)-folinic acid over (6S)-folinic acid in vivo with no induction of gene expression observed in the presence of (6S)-folinic acid. Both switches also achieve stringent regulatory silencing in the absence of ligand as low as 3.4%, indicating that they are biologically orthogonal and not sensitive to intracellular folates or other metabolites or macromolecules, in contrast to some switches that have been developed. Interestingly, (6R)-FA-switch2 includes a deletion within the transmitter component, which only includes 14 nucleotides. These switches demonstrate that selected folinic acid aptamers function intracellularly and can be coupled to ribozymes to confer folinic acid-responsive gene regulation.

Switches may upregulate or downregulate gene expression in response to ligand. Switches may be present in different genetic contexts (e.g., different promoters, regulated genes, genomic integration vs. plasmid expression).

In vitro selection methods enable de novo generation of RNA sensing capabilities, potentially allowing genetic switches to any desired molecular target. However, challenges associated with generating sensor components that are amenable to subsequent switch integration and that function in vivo have limited available sensing capabilities and possible applications. By applying selection design principles that favor the selection of aptamers that bind with high affinity and specificity under physiologically relevant conditions, a panel of RNA aptamers was generated that bind the clinical drug folinic acid with binding affinities as low as 19.2 nM and specificities over 70,000-fold against structurally similar compounds. Through library screening, folinic acid-responsive RNA switches were engineered that activate gene expression in vivo. Ribozyme-based switches have previously been demonstrated to transfer from yeast or bacterial systems to mammalian systems. In addition, the modular construction of these switches enables facile substitution of folinic acid aptamers into previously developed theophylline-responsive switches implemented in clinically relevant proof-of-concept studies regulating T cell proliferation for adoptive transfer therapy (see Chen et al. (2010) PNAS 107(19):8531-8536) and viral replication for gene therapy and vaccine development. The limited toxicity of folinic acid observed in clinical use indicates that these sensing and regulatory capabilities are broadly applicable and provide a general, nontoxic small molecule effector for controlling gene expression in bacterial, fungal, and mammalian systems and for more sensitive clinical applications. In addition to previously mentioned applications in T cell proliferation and gene therapy, additional potential clinical applications include bacterial probiotic treatments including pathogen seeking and killing, tumor invasion, and living diagnostics.

The in vitro selected folinic acid aptamers can be compared to the recently discovered natural tetrahydrofolate riboswitch. Although also able to bind folinic acid, the tetrahydrofolate riboswitch exhibits much lower affinity (~10-20 µM), low specificity between diastereomers (<1.5-fold) and against purines (with certain purines even binding more tightly than the cognate ligand), long length (~90 nt), and multiple ligand binding sites, rendering it more challenging for incorporating into a synthetic regulatory switch and unsuitable for clinical applications due to its low specificity and affinity (Ames et al. (2010) Chemistry & Biology 17(7):681-685).

Applications for these aptamers include gene regulatory devices across cell and organism types and in therapeutic applications. In vivo biosensors for folate derivatives may be constructed from (6S)-folinic acid specific aptamers and used to monitor intracellular folate metabolism, to engineer folate central metabolism of this critical cofactor, or to engineer strains to overproduce these compounds. These aptamers can be evolved to bind to other folate analogues, both natural and unnatural such as the antifolate drugs methotrexate or pemetrexed. The different pharmacokinetic properties of the two diastereomers of folinic acid enable switches with different temporal control to be designed: one with a fast-acting and short-lived pulse of gene expression and a second with a longer, sustained pulse.

Aptamers and synthetic RNA regulatory switches provide a powerful approach for generating novel biological sensing and control capabilities with which to program gene expression and cellular behavior. Coupling de novo, in vitro selection with regulatory switch construction methods holds promise for greatly expanding the ligand chemical diversity of inducible gene expression systems. Historically, not many aptamer selections have been conducted with the primary intent of in vivo function. To increase the likelihood of generating sensing capabilities that function in vivo and are readily integrated into regulatory switch platforms, a system of design, control, and validation was applied to the process of generating a novel inducible gene expression system. By rigorously controlling design parameters and quantitatively validating the processes of ligand immobilization, aptamer selection, aptamer screening, and switch construction, this system provides a strategy for identifying, prototyping, and carrying forward promising ligand, aptamer, and switch candidates and combines the strengths of in vitro and in vivo methods. This systematized process can serve as a template and model to guide the development of other RNA-based inducible gene regulatory systems and expand their possible applications in engineering increasingly sophisticated biological systems.

TABLE 3

| | Selection Round | | | | | | | | | |
|---|---|---|---|---|---|---|---|---|---|---|
| | 1 | 2 | 3 | 4 | 5 | 6 | 7 | 8 | 9 | 10 |
| [FA] on Column | 2 mM | 2 mM | 200 µM | 200 µM | 20 µM | 20 µM | 2 µM | 2 µM | 2 µM | 2 µM |
| Buffer Wash 1 | 0.01% | 0.02% | 0.00% | 0.07% | 0.06% | 0.13% | 0.02% | 0.03% | 0.06% | 0.07% |
| Buffer Wash 2 | 52.33% | 58.84% | 0.05% | 0.07% | 0.06% | 0.13% | 0.04% | 0.03% | 0.06% | 0.28% |
| Buffer Wash 3 | 42.16% | 28.25% | 28.01% | 16.16% | 17.64% | 6.34% | 24.63% | 26.25% | 16.88% | 23.38% |
| Buffer Wash 4 | 4.36% | 4.71% | 50.03% | 35.02% | 50.41% | 43.09% | 47.01% | 52.50% | 51.93% | 55.02% |
| Buffer Wash 5 | 0.44% | 1.41% | 16.51% | 13.47% | 18.90% | 22.81% | 22.39% | 12.83% | 18.18% | 11.69% |
| Buffer Wash 6 | 0.17% | 0.71% | 2.50% | 5.39% | 6.30% | 8.87% | 2.69% | 3.21% | 2.99% | 2.20% |
| Buffer Wash 7 | | 0.42% | 0.60% | 4.71% | 2.27% | 4.06% | 0.85% | 0.88% | 1.43% | 1.03% |
| Buffer Wash 8 | | 0.33% | 0.25% | 3.37% | 1.26% | 2.53% | 0.40% | 0.58% | 0.65% | 0.55% |
| Buffer Wash 9 | | 0.24% | 0.20% | 3.03% | 0.63% | 1.77% | 0.18% | 0.47% | 0.52% | 0.41% |
| Buffer Wash 10 | | | 0.15% | 2.15% | 0.38% | 1.27% | 0.13% | 0.29% | 0.45% | 0.34% |
| Buffer Wash 11 | | | | 2.02% | 0.32% | 1.27% | 0.09% | 0.23% | 0.39% | 0.34% |
| Buffer Wash 12 | | | | 1.75% | 0.19% | 0.76% | 0.07% | 0.23% | 0.32% | 0.28% |
| Buffer Wash 13 | | | | 1.48% | 0.19% | 0.63% | 0.06% | 0.18% | 0.32% | 0.28% |
| Buffer Wash 14 | | | | | | 0.51% | 0.06% | 0.16% | 0.32% | 0.21% |
| Buffer Wash 15 | | | | | | 0.51% | 0.04% | 0.15% | 0.26% | 0.21% |
| Buffer Wash 16 | | | | | | 0.51% | 0.04% | 0.15% | 0.32% | 0.21% |
| Buffer Wash 17 | | | | | | | | 0.12% | 0.26% | 0.21% |
| Buffer Wash 18 | | | | | | | | 0.12% | 0.19% | 0.21% |
| Buffer Wash 19 | | | | | | | | 0.09% | 0.19% | 0.14% |
| Buffer Wash 20 | | | | | | | | | | 0.14% |
| Buffer Wash 21 | | | | | | | | | | 0.14% |
| Buffer Wash 22 | | | | | | | | | | 0.14% |
| Sum Buffer Washes | 99.48% | 94.93% | 98.30% | 88.69% | 98.61% | 95.18% | 98.70% | 98.48% | 95.75% | 97.46% |
| [FA] in Elutions | 20 mM | 20 mM | 20 mM | 20 mM | 2 mM | 2 mM | 200 µM | 200 µM | 200 µM | 200 µM |
| FA Elution 1 | 0.12% | 0.19% | 0.15% | 1.35% | 0.19% | 0.51% | 0.04% | 0.09% | 0.23% | 0.14% |
| FA Elution 2 | 0.17% | 0.38% | 0.30% | 8.08% | 0.38% | 2.28% | 0.09% | 0.20% | 1.17% | 0.62% |
| FA Elution 3 | 0.03% | 0.14% | 0.15% | 0.81% | 0.13% | 0.51% | 0.04% | 0.09% | 0.45% | 0.21% |
| FA Elution 4 | 0.03% | 0.06% | 0.10% | 0.20% | 0.06% | 0.25% | 0.07% | 0.18% | 0.91% | 0.41% |

TABLE 3-continued

| | | | | | | | | | | |
|---|---|---|---|---|---|---|---|---|---|---|
| FA Elution 5 | 0.01% | 0.05% | 0.05% | 0.13% | 0.06% | 0.13% | 0.04% | 0.09% | 0.32% | 0.14% |
| FA Elution 6 | 0.01% | 0.02% | 0.05% | 0.07% | 0.06% | 0.13% | 0.02% | 0.06% | 0.13% | 0.07% |
| Sum FA Elutions | 0.38% | 0.84% | 0.80% | 10.64% | 0.88% | 3.80% | 0.31% | 0.70% | 3.21% | 1.58% |
| Blocked Negative Selection Column | — | — | 0.60% | 0.40% | 0.32% | 0.63% | 0.81% | 0.53% | 0.78% | 0.76% |
| FA Conjugated Column | 0.15% | 4.24% | 0.30% | 0.27% | 0.19% | 0.38% | 0.18% | 0.29% | 0.26% | 0.21% |

In vitro selection design, stringency, and progress. Steady increases in selection stringency are incorporated into selection through gradual increases in buffer wash volume, decreases in concentration of folinic acid conjugated onto solid support beads, and decreases in concentration of folinic acid in elution. Selection progress is monitored through RNA retention profile. Percentage of $^{32}$P-radiolabeled RNA in each fraction is measured using a Geiger counter. Volume of all columns, buffer washes, and elutions is 0.5 mL. Blocked negative selections columns are used in selection rounds 3 through 10. Input RNA library is added to negative selection column and flows into folinic acid conjugated selection column with addition of buffer washes, shifting RNA retention profile by one wash (i.e., peak RNA fractions are buffer washes 2 and 3 for rounds 1 and 2 but shifts to buffer washes 3 and 4 for remaining rounds since RNA must travel through an additional volume of beads in second column). Negative selection columns are removed after four buffer washes, and remaining buffer washes and elutions are added directly to selection column.

TABLE 4

Sequences of folinic acid aptamers.

| In vitro selection | Antisense DNA sequence |
|---|---|
| N70 library SEQ ID NO: 1 | 5'-GTGTCCGCCTATCTCGTCTCCNNNNNNNNNNNNNNNNNNNNNNNNNNNNNNNNNNNNNNNNNNNNNNNNNNNNNNNNNNNNNNNNNGGAAGGAGGCGGGCAGAAGTCCCTATAGTGAGTCGTATTAGAA |

| Aptamers | Full-length RNA sequence from in vitro selection |
|---|---|
| (6R)-FA specific aptamers | |
| FA8-4 SEQ ID NO: 2 | 5'-GGGACUUCUGCCCGCCUCCUUCCUGCUCGUGUCAAAAUGAAUGGCGCUCGGCGUUGCGUGGUACGUUAUAUUCCGGCCAAGCAGCCAUUCAUGGGAGACGAGAUAGGCGGACAC |
| FA8-3 SEQ ID NO: 3 | 5'-GGGACUUCUGCCCGCCUCCUUCCGCUGAGGACUCGGCACCGAAUUUGCCAACGUCUGGUCACGACCGUAGUACACUACCCCUCGAAAUCACGAGGGAGACGAGAUAGGCGGACAC |
| FA8-11 SEQ ID NO: 4 | 5'-GGGACUUCUGCCCGCCUCCUUCCGCUUACCGGACGCCUUAAGGCAUCAGCAUGCAGUGCUUGGUACGUUAUAUUCAGCUGCAACUCGGGAUGCGGAGACGAGAUAGGCGGACAC |
| FA6-8 SEQ ID NO: 5 | 5'-GGGACUUCUGCCCGCCUCCUUCCGCUAUAAGUCGGACUUCCCGUCAGGUACGUUAUAUUCGGGGAGUACGGUUAAAGCAGAUUUGUUGAAUGGAGACGAGAUAGGCGGACAC |
| FA8-16 SEQ ID NO: 6 | 5'-GGGACUUCUGCCCGCCUCCUUCCGGUGACCUGGACGUUAUUUCCGGCCGAAGGGAGACGAGAUAGGCGGACAC |
| (6S)-FA specific aptamers | |
| FA8-18 SEQ ID NO: 7 | 5'-GGGACUUCUGCCCGCCUCCUUCCUACUCCCGACUCGUCAAUGCAUAUGUAACGUUAACGGCGCUACCUGUACAAUGCACGUUCCGAGCGCCCGGAGACGAGAUAGGCGGACAC |
| FA10-7 SEQ ID NO: 8 | 5'-GGGACUUCUGCCCGCCUCCUUCCCCGACACGGCGAAGAGUCAAAGCAUCCCCUGCAUGGAGCCAACAAGCCCUGCCUCCACGCAGGGCCCGUGGGAGACGAGAUAGGCGGACAC |

TABLE 4-continued

Sequences of folinic acid aptamers.

| | |
|---|---|
| FA8-14<br>SEQ ID NO: 9 | 5'-<br>GGGACUUCUGCCCGCCUCCUUCCGCGCAAGUGCAUUAACGGUGACACCGAAAGC<br>UGGAAAGCCUGACAUCGAACGCAAAAGGCUGCGUGGCAUGGAGACGAGAUAGGC<br>GGACAC |

| Truncated<br>Aptamers | DNA sequence for SPR |
|---|---|
| (6R)-FA specific<br>aptamers | |
| FAt8-4<br>SEQ ID NO: 10 | 5'-<br>TTCTAATACGACTCACTATAGGGGCTTGGCGTTGCGTGGTACGTTATATTCCGG<br>CCAAGCCCCAAAAAAAAAAAAAAAAAAAAAAAA |
| FAt8-3<br>SEQ ID NO: 11 | 5'-<br>TTCTAATACGACTCACTATAGGGTTTGCCAACGTCTGGTCACGACCGTAGTACA<br>CTACCCCTCGAAATCACGAGGGAGACGAGATAGGCGGACCCCAAAAAAAAAAAA<br>AAAAAAAAAA |
| FAt8-11<br>SEQ ID NO: 12 | 5'-<br>TTCTAATACGACTCACTATAGGGTGCAGTGCTTGGTACGTTATATTCAGCTGCA<br>CCCCAAAAAAAAAAAAAAAAAAAAAAAA |
| FAt6-8<br>SEQ ID NO: 13 | 5'-<br>TTCTAATACGACTCACTATAGGGTTCCCGTCAGGTACGTTATATTCGGGGGACC<br>CCAAAAAAAAAAAAAAAAAAAAAAAA |
| FAt8-16<br>SEQ ID NO: 14 | 5'-<br>TTCTAATACGACTCACTATAGGGCTCCTTCCGGTGACCTGGACGTTATTTCCGG<br>CCGAAGGGAGCCCCAAAAAAAAAAAAAAAAAAAAAAAA |
| (6S)-FA specific<br>aptamers | |
| FAt8-18<br>SEQ ID NO: 15 | 5'-<br>TTCTAATACGACTCACTATAGGGCTCGTCAATGCATATGTAACGTTAACGGCGC<br>TACCTGTACAATGCACGTTCCGAGCGCCCGGAGACGAGCCCCAAAAAAAAAAAA<br>AAAAAAAAAA |
| FAt10-7<br>SEQ ID NO: 16 | 5'-<br>TTCTAATACGACTCACTATAGGGACGGCGAAGAGTCAAAGCATCCCCTGCGAAA<br>GCAGGGCCCGTCCCCAAAAAAAAAAAAAAAAAAAAAAAA |
| FAt8-14<br>SEQ ID NO: 17 | 5'-<br>TTCTAATACGACTCACTATAGGGCCGCGCAAGTGCATTAACGGTGACACCGAAA<br>GCTGGAAAGCCTGACATCGAACGCAAAAGGCTGCGTGGCCCCAAAAAAAAAAAA<br>AAAAAAAAAA |

| Truncated<br>Aptamers | RNA sequence |
|---|---|
| (6R)-FA specific<br>aptamers | |
| FAt8-4<br>SEQ ID NO: 18 | 5'-GCUUGGCGUUGCGUGGUACGUUAUAUUCCGGCCAAGC |
| FAt8-3<br>SEQ ID NO: 19 | 5'-<br>UUUGCCAACGUCUGGUCACGACCGUAGUACACUACCCCUCGAAAUCACGAGGGA<br>GACGAGAUAGGCGGA |
| FAt8-11<br>SEQ ID NO: 20 | 5'-UGCAGUGCUUGGUACGUUAUAUUCAGCUGCA |
| FAt6-8<br>SEQ ID NO: 21 | 5'-UUCCCGUCAGGUACGUUAUAUUCGGGGA |
| FAt8-16<br>SEQ ID NO: 22 | 5'-CUCCUUCCGGUGACCUGGACGUUAUUUCCGGCCGAAGGGAG |
| (6S)-FA specific<br>aptamers | |
| FAt8-18<br>SEQ ID NO: 23 | 5'-<br>CUCGUCAAUGCAUAUGUAACGUUAACGGCGCUACCUGUACAAUGCACGUUCCGA<br>GCGCCCGGAGACGAG |

TABLE 4-continued

Sequences of folinic acid aptamers.

| | |
|---|---|
| FAt10-7<br>SEQ ID NO: 24 | 5'-ACGGCGAAGAGUCAAAGCAUCCCCUGCGAAAGCAGGGCCCGU |
| FAt8-14<br>SEQ ID NO: 25 | 5'-CCGCGCAAGUGCAUUAACGGUGACACCGAAAGCUGGAAAGCCUGACAUCGAACGCAAAAGGCUGCGUGG |

| Mutated Aptamer | DNA sequence for SPR |
|---|---|
| FAt8-4-stem1<br>SEQ ID NO: 26 | 5'-TTCTAATACGACTCACTATAGGGTAGGTTCGTTGCGTGGTACGTTATATTCCGGAACCTACCCCAAAAAAAAAAAAAAAAAAAAAAAA |
| FAt8-4-stem2<br>SEQ ID NO: 27 | 5'-TTCTAATACGACTCACTATAGGGTAGGTTAGTTGCGTGGTACGTTATATTCCGTAACCTACCCCAAAAAAAAAAAAAAAAAAAAAAAA |
| FAt8-4-stem3<br>SEQ ID NO: 28 | 5'-TTCTAATACGACTCACTATAGGGGCTTGGCGTTGCGTGCAGTGAGCCTACTGGTACGTTATATTCCGGCCAAGCCCCAAAAAAAAAAAAAAAAAAAAAAAA |
| FAt8-4-stem4<br>SEQ ID NO: 29 | 5'-TTCTAATACGACTCACTATAGGGGCTTGGCGTTGCGTGGCAGTGAGCCTACTGTACGTTATATTCCGGCCAAGCCCCAAAAAAAAAAAAAAAAAAAAAAAA |

| Primers | DNA sequence |
|---|---|
| N70-fwd<br>SEQ ID NO: 30 | 5'-TTCTAATACGACTCACTATAGGGACTTCTGCCCGCCTCCTTCC |
| N70-fwd-short<br>SEQ ID NO: 31 | 5'-TTCTAATACGACTCACTATAGGGACTTCTGCCCGCCTC |
| N70-rev<br>SEQ ID NO: 32 | 5'-GTGTCCGCCTATCTCGTCTCC |
| GAP-N70-AvrII-fwd-short<br>SEQ ID NO: 33 | 5'-TCCATGGTATGGATGAATTGTACAAATAAAGCCTAGGGGGACTTCTGCCCGCCTC |
| GAP-N70-XhoI-rev<br>SEQ ID NO: 34 | 5'-AAGAAATTCGCTTATTTAGAAGTGGCGCGCCCTCTCGAGAGTGTCCGCCTATCTCGTCTCC |
| Biacore-N70-rev<br>SEQ ID NO: 35 | 5'-TTTTTTTTTTTTTTTTTTTTTTTGGGGGTGTCCGCCTATCTCGTCTCC |
| Biacore-fwd<br>SEQ ID NO: 36 | 5'-TTCTAATACGACTCACTATAGGG |
| Biacore-rev<br>SEQ ID NO: 37 | 5'-TTTTTTTTTTTTTTTTTTTTTTTGGGG |

TABLE 5

Sequences for transmitter-based device library and isolated folinic acid-responsive switches.

| RNA Switches | DNA sequence |
|---|---|
| FA8-4-sTRSV N11 transmitter library<br>SEQ ID NO: 38 | 5'-AAACAAACAAAGCTGTCACCGGATGTGCTTTCCGGTCTGATGAGTCCGTTNNNCGTTGCGTGGTACGTTATATTCCGGNNNNNNNNNGGAGGACGAAACAGCAAAAGAAAATAAAAA |
| (6R)-FA-switch1<br>SEQ ID NO: 39 | 5'-AAACAAACAAAGCTGTCACCGGATGTGCTTTCCGGTCTGATGAGTCCGTTGGTCGTTGCGTGGTACGTTATATTCCGGGCCGAACGGGAGGACGAAACAGCAAAAGAAAATAAAAA |
| (6R)-FA-switch2<br>SEQ ID NO: 40 | 5'-AAACAAACAAAGCTGTCACCGGATGTGCTTTCCGGTCTGATGAGTCCGTTGCTCGTTGCGTGGTACGTTATATTCCGGGGCGAACGGAGGACGAAACAGCAAAAGAAAATAAAA |

TABLE 5-continued

Sequences for transmitter-based device library and isolated folinic acid-responsive switches.

| RNA Switches | DNA sequence |
| --- | --- |
| sTRSV<br>SEQ ID NO: 41 | 5'-AAACAAACAAAGCTGTCACCGGATGTGCTTTCCGGTCTGATGAGTCCGTGAGGACGAAACAGCAAAAAGAAAAATAAAAA |
| sTRSV Cont1<br>SEQ ID NO: 42 | 5'-AAACAAACAAAGCTGTCACCGGATGTGCTTTCCGGTACGTGAGGTCCGTGAGGACAGAACAGCAAAAAGAAAAATAAAAA |
| L2b8<br>SEQ ID NO: 43 | 5'-AAACAAACAAAGCTGTCACCGGATGTGCTTTCCGGTCTGATGAGTCCGTTGTCCATACCAGCATCGTCTTGATGCCCTTGGCAGGGACGGGACGGAGGACGAAACAGCAAAAAGAAAAATAAAAA |

| Primers | DNA sequence |
| --- | --- |
| GAP-N70-AvrII-fwd-short<br>SEQ ID NO: 44 | 5'-TCCATGGTATGGATGAATTGTACAAATAAAGCCTAGGGGACTTCTGCCCGCCTC |
| GAP-N70-XhoI-rev<br>SEQ ID NO: 45 | 5'-AAGAAATTCGCTTATTTAGAAGTGGCGCGCCCTCTCGAGAGTGTCCGCCTATCTCGTCTCC |
| GAP-L1-2-fwd<br>SEQ ID NO: 46 | 5'-TCCATGGTATGGATGAATTGTACAAATAAAGCCTAGGAAACAAACAAAGCTGTCACC |
| GAP-L1-2-rev<br>SEQ ID NO: 47 | 5'-AAGAAATTCGCTTATTTAGAAGTGGCGCGCCCTCTCGAGTTTTTATTTTTCTTTTTGCTGTTTCG |
| L1-2-fwd<br>SEQ ID NO: 48 | 5'-GACCTAGGAAACAAACAAAGCTGTCACC |
| L1-2-rev<br>SEQ ID NO: 49 | 5'-GGCTCGAGTTTTTATTTTTCTTTTTGCTGTTTCG |
| CS653<br>SEQ ID NO: 50 | 5'-GGTCACAAATTGGAATACAACTATAACTCT |
| CS654<br>SEQ ID NO: 51 | 5'-CGGAATTAACCCTCACTAAAGGG |

| Plasmids | Plasmid Number |
| --- | --- |
| sTRSV | pCS1750 |
| sTRSV Cont1 | pCS1751 |
| GFP | pCS1585 |
| mCherry | pCS1749 |
| no color | pCS4 |
| L2b8 | pCS1753 |
| GFP-mCherry | pCS1748 |

Example 2

Aptamer mutations were studied to assess their effect on ligand binding to better understand which nucleotides were involved in or necessary for binding and to identify sequence flexibility that could be leveraged during switch design. In particular, integration into regulatory switch platforms generally requires one or more stems through which to couple the aptamer to the actuator. Thus, identifying potential integration stems whose sequence can be modified for facile integration while not affecting ligand binding is a critical step in switch design.

Aptamer stems were assayed for sequence flexibility or constraints by shuffling nucleotide identify (A to C, C to A, G to U, and U to G to maintain U-G basepairing). If shuffled stem sequences retained binding ability, stems were labeled as sequence unconstrained without testing all six possible base pairs (A-U, U-A, C-G, G-C, U-G, G-U). Terminal stem loop lengths were tested to minimize stem length, and individual point mutations were rationally picked and tested (FIG. 18). Aptamers specific for both (6R)- and (6S)-folinic acid were identified that contained two sequence unconstrained stems, thus enabling aptamer integration into regulatory platforms requiring either one (e.g., ribozyme-based)

or two (e.g., miRNA or Rnt1p-based) integration sites. Aptamers with more than one integration stem provide more design flexibility even for switch platforms only requiring one site, as aptamer orientation can be chosen.

Next, particular functional groups of folinic acid that were important for aptamer binding were tested. With many natural and unnatural folate analogues available, binding of two derivatives were characterized that altered specific functionalities of folinic acid, which is composed of pterin, para-aminobenzoate, glutamate, and formyl moieties (FIG. 19). (6R,S)-5-methyl-5,6,7,8-tetrahydrofolic acid replaces the 5-formyl group with a 5-methyl group, testing the role of the formyl oxygen on binding. (6R,S)-5-formyl-5,6,7,8-tetrahydropteroic acid removes the glutamate group through hydrolysis of the amide bond. While binding characterization indicates a significant role of the 5-formyl oxygen in binding, the glutamate residue appears to be nonessential (Table 6). Removing the glutamate residue maintains or potentially increases binding affinity, possibly due to the decrease in conformational flexibility of the ligand from the number of rotatable bonds, decreasing entropic cost of ligand binding necessary for locking molecule into a rigid binding conformation, and possibly preventing the glutamate moiety from folding into a conformation that prevents or disrupts binding with RNA. By removing the unnecessary moiety, the kinetics of binding ($k_a$) are potentially increased.

aptamers may be evolved to bind to other folate analogues, both natural and unnatural such as the antifolates methotrexate or pemetrexed.

Example 3

Rational design of ribozyme-based switches in yeast. Folinic acid-responsive switches were first rationally designed to demonstrate aptamer in vivo activity. The strand displacement mechanism previously used to rationally design theophylline- and tetracycline-responsive switches was tested on two different switch architectures: aptamer integration off of the hammerhead loop II and integration through hammerhead helix III (FIG. 20). For loop II integration, transmitter sequences from previously characterized switches were used as a starting point to join folinic acid aptamers FA8-4 and FA8-3 to the sTRSV hammerhead ribozyme, tested in silico using RNA folding programs, and modified as necessary to achieve proper folding of the ribozyme and aptamer domains.

Helix III integration represents an alternate switch architecture that has not previously been reported. Aptamer integration through helix III requires two integration stems on the aptamer: one for ribozyme helix III integration and another for transcript integration. In this architecture, the ribozyme sequence does not need to be altered, and therefore

TABLE 6

| Aptamer | (6R,S)-5-methyl-THF | | | (6R,S)-5-formyl-THPteroic Acid | | |
|---|---|---|---|---|---|---|
| | $k_a$ (M$^{-1}$s$^{-1}$) | $k_d$ (s$^{-1}$) | $K_D$ (M) | $k_a$ (M$^{-1}$s$^{-1}$) | $k_d$ (s$^{-1}$) | $K_D$ (M) |
| 8-4 | 3.35E+04 | 2.11E−01 | 6.29E−06 | 1.35E+05 | 4.94E−03 | 3.66E−08 |
| 8-11 | 1.43E+04 | 1.95E−01 | 1.36E−05 | 7.50E+05 | 5.68E−03 | 7.57E−08 |
| 8-3 | — | — | 1.58E−07 | 3.05E+05 | 2.92E−02 | 9.57E−08 |
| 8-18 | — | — | 4.47E−04 | 5.32E+04 | 6.33E−03 | 1.19E−07 |
| 10-7 | — | — | 8.18E−05 | 3.52E+04 | 6.97E−03 | 1.98E−07 |

Kinetic and equilibrium binding properties of aptamers for folinic acid derivatives. (6R,S)-5-methyl-THF and (6R,S)-5-formyl-THPteroic acid are mixtures of both (6R) and (6S) diastereomers; thus, when comparing binding to the specific folinic acid diastereomer, $k_a$ and $K_D$ values should be adjusted accordingly.

More detailed structural information on aptamer-ligand binding can be obtained through chemical probing experiments such as SHAPE, crystallography, or nuclear magnetic resonance imaging. More detailed information on the energy binding landscape could be obtained through single-molecule force and folding studies or high-throughput mutational and affinity measurements such as RNA-MITOMI. In addition, since the glutamate moiety of folinic acid is not necessary for ligand binding, tagged derivatives of folinic acid can be synthesized, using the glutamate residue of folinic acid or the benzoic acid of 5-formyl-5,6,7,8-tetrahydropteoric acid as a chemical handle to couple a cargo such as a fluorophore tag to. The availability of diverse folate analogues can also be mined to test the effect of different oxidation states of the carbon atoms in the 5, 6, 7, or 8 positions or ligand conformation through derivatives that bridge the 5' and 10' nitrogens.

Applications for these aptamers include gene-regulatory devices across cell and organism types and in therapeutic applications. In vivo biosensors for folate derivatives may be constructed from (6S)-folinic acid specific aptamers and used to monitor intracellular folate metabolism, to engineer folate central metabolism of this critical cofactor, or to engineer strains to overproduce these compounds. These the native tertiary loop-loop interactions are maintained, with the goal of achieving lower basal activity and eliminating the need to rescue impaired tertiary interactions. However, this integration method could potentially be kinetically unfavorable, as the entire ribozyme sequence is transcribed before the aptamer is, possibly reducing the time for ligand binding to prevent ribozyme cleavage. This integration design is partially inspired by reported in vitro aptameric sensors that couple two aptamer domains, in vivo miRNA and Rnt1p switch designs, and Spinach-based sensors. However, these sensors and switches operate through conformational changes upon ligand binding that stabilize connecting stems (e.g., communication modules) or sequester aptamer nucleotides from enzymatic recognition and processing, thus making the use of a transmitter junction a novel switch architecture.

Figure 21:
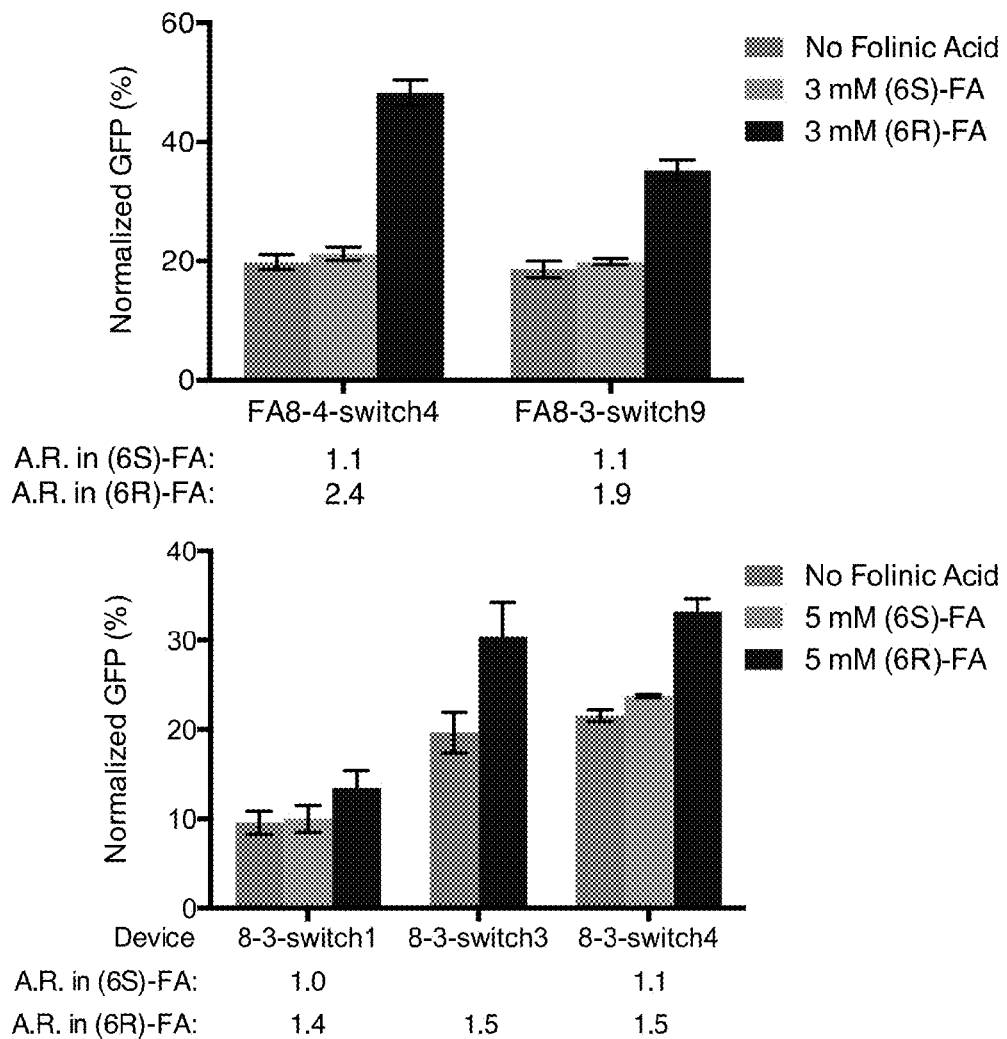
FIG. 21. Rationally designed folinic acid-responsive, ribozyme-based devices regulate gene expression in vivo in yeast.

Switches achieved activation ratios up to 2.4-fold, while retaining specificity for (6R)-folinic acid over (6S)-folinic acid (FIG. 21). These switches demonstrate that selected folinic acid aptamers function intracellularly and can be coupled to ribozymes to confer folinic acid-responsive gene regulation. Of interest to note is that ribozyme active structure for FA8-3-switch9 is the second lowest energy predicted structure, in contrast to most designed ribozyme-based switches, where it is the lowest energy structure (−44.7 kcal/mol vs. −45.6 kcal/mol for aptamer folded structure).

Example 4

Ribozyme Loop Replacement Screen in Yeast

An alternative switch architecture based on ribozyme loop replacement has recently been demonstrated to generate theophylline-responsive switches that function in vivo. This strategy relies on the observation that natural hammerhead ribozymes possess many sequence solutions for maintaining tertiary loop-loop interactions that are crucial for stringent regulatory silencing (FIG. 22). Previous work has also enabled impaired loop-loop interactions to be rescued through screening of a completely randomized ribozyme loop, resulting in lower basal activity. Combining these two observations, this integration strategy replaces one of the two interacting hammerhead loops with an aptamer, placing an internal or terminal loop of an aptamer approximately in the same position as the replaced ribozyme loop. To rescue the loop-loop interaction, the second loop is completely randomized and the device library is screened for functional switches. In the absence of ligand, nucleotides of the two loops are predicted to interact through tertiary interactions. However, in the presence of ligand, ligand binding to the aptamer sequesters aptamer nucleotides involved in the loop-loop interaction, precluding proper tertiary contact formation and disrupting ribozyme cleavage. Because refolding of the aptamer domain is unnecessary in this switch architecture, this switch design has been shown to be more sensitive than transmitter-based designs, resulting in a lower IC50 needed to activate the switch. Previously designed transmitter-based ON switches require two functional conformations: one with active ribozyme and inactive aptamer and a second with a properly folded aptamer and an improperly folded ribozyme. These two functional conformations are generally among the lowest energy predicted secondary structures, with a slightly energetically favored active ribozyme conformation and with a difference in energy small enough for ligand binding to favor the active aptamer conformation. With both the ribozyme and aptamer folded into their functional conformations, removing competing secondary structures should also lead to lower basal activities (assuming that tertiary contacts can be restored) and can avoid impairing aptamer affinities upon switch integration that have been previously observed.

Figure 23:
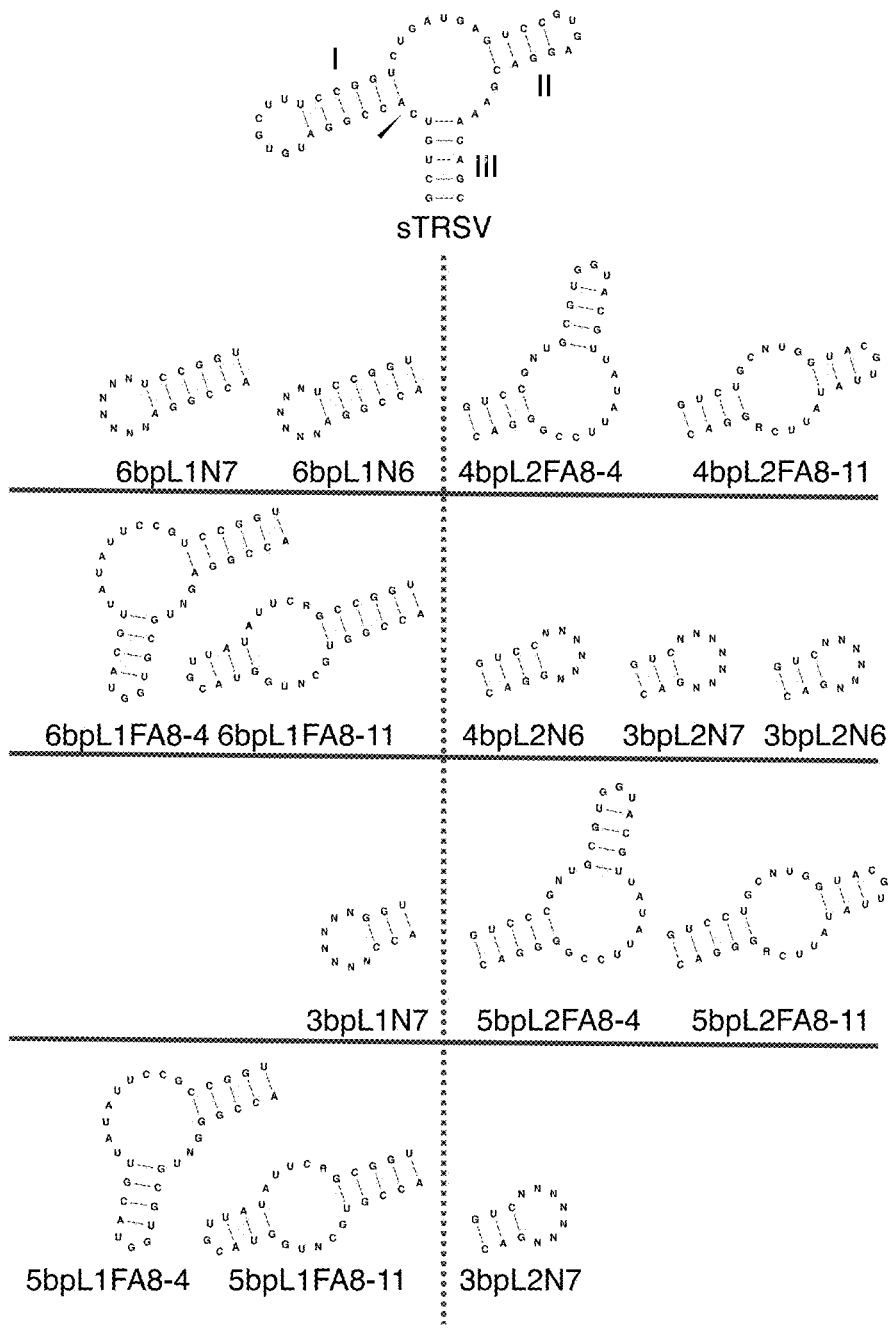
FIG. 23. Device library for folinic acid aptamer loop replacement strategy.sTRSV:SEQ ID NO:108; 6bpL1N7: SEQ ID NO:109; 6bpL1N6: SEQ ID NO:110; 6bpL1FA8-4: SEQ ID NO:111; 6bpL1FA8-11: SEQ ID NO:112; 3bpL1N7: SEQ ID NO:113; 5bpL1FA8-4: SEQ ID NO:114; 5bpL1FA8-11: SEQ ID NO:123; 4bpL2FA8-4: SEQ ID NO:115; 4bpL2FA8-11: SEQ ID NO:116; 4bpL2N6: SEQ ID NO:117; 3bpL2N7: SEQ ID NO:118; 3bpL2N6: SEQ ID NO:119; 5bpL2FA8-4: SEQ ID NO:120; 4bpL2FA8-11: SEQ ID NO:121; and 3bpL2N7: SEQ ID NO:122.

Fourteen device libraries based on ribozyme loop replacement were synthesized and pooled together for cell sorting (FIG. 23). Two folinic acid aptamers, FA8-4 and FA8-11, were chosen for their high affinity, short lengths, and unconstrained base stems and replaced either loop I or loop II in device libraries. Library designs were inspired by sequence diversity of natural hammerhead ribozymes, with prevalent combinations of stem and loop lengths used as the basis of designed libraries. Positions within the aptamer domain that had been identified as variable were also randomized. These positions, located near the base stem of the aptamer, were hypothesized to occupy loop positions that would be more likely to be involved in forming tertiary contacts; thus, additional diversity in these privileged positions would potentially lead to functional switches. For switches including aptamer FA8-4, the base stem sequence was derived from the parent ribozyme. For switches including aptamer FA8-11, the first base pair of the base stem sequence was conserved as a U-G base pair as this base pair was observed to be conserved in the functional aptamer.

Figure 24A:
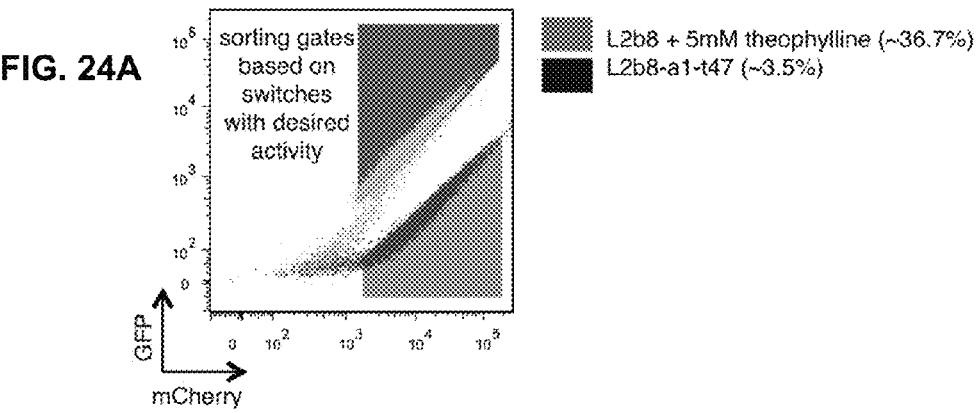
FIG. 24A-24B. Loop replacement screen for folinic acid switches.
Figure 24B:
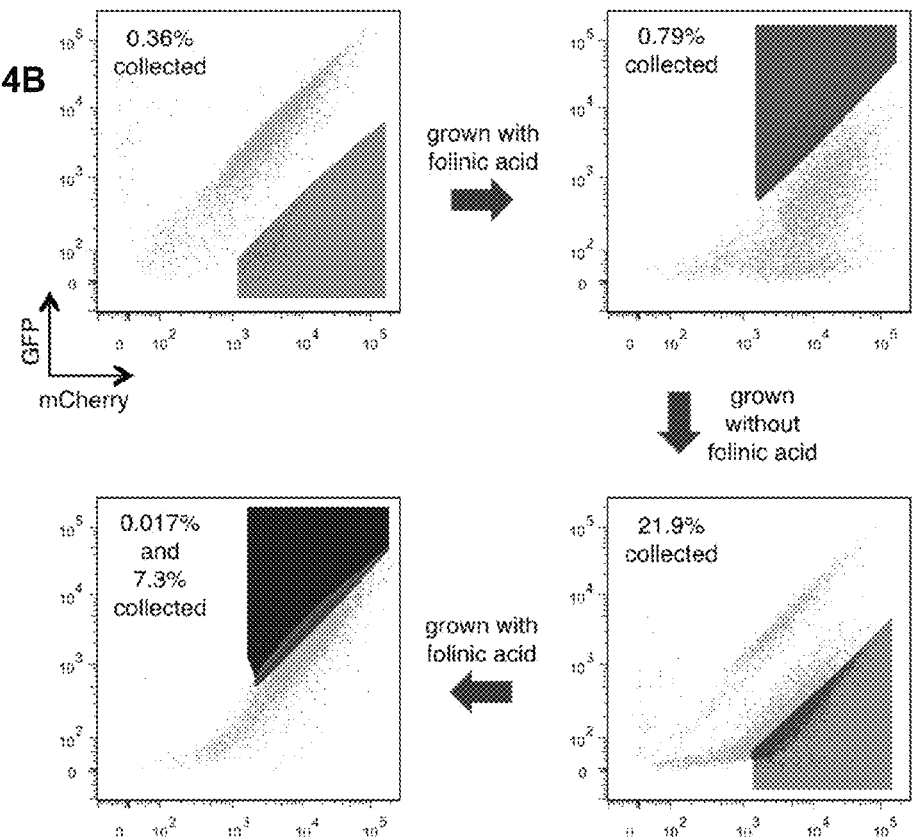
Figure 25A:
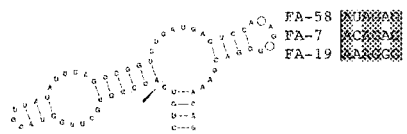
FIG. 25A-25G. Folinic acid-responsive switches isolated from loop replacement screen.
Figure 25B:
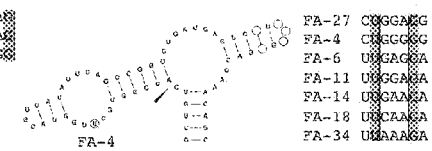
Figure 25C:
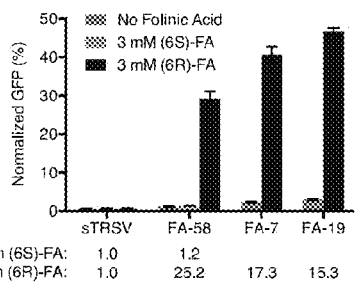
Figure 25D:
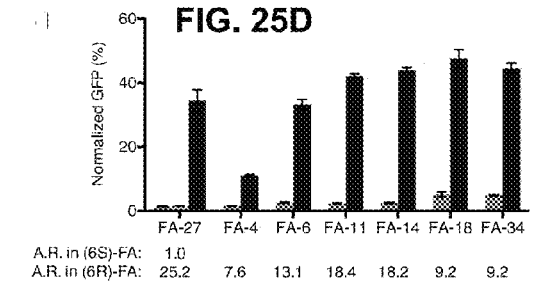
Figure 25E:
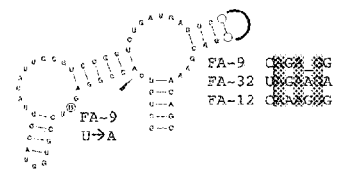
Figure 25F:
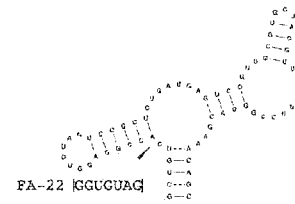
Figure 25G:
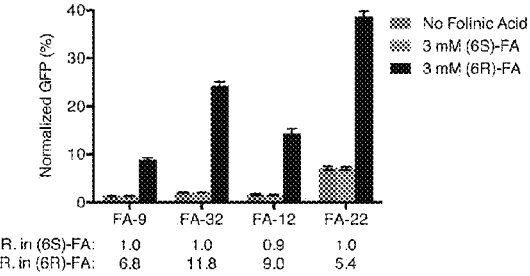

Four rounds of cell sorting were conducted, using sorting collection gates based off of two previously characterized theophylline switches with activities of ~3.5% for the negative sorting gate in the absence of folinic acid and ~36.7% for the positive sorting gate in the presence of folinic acid (FIG. 24a).

Figure 26A:
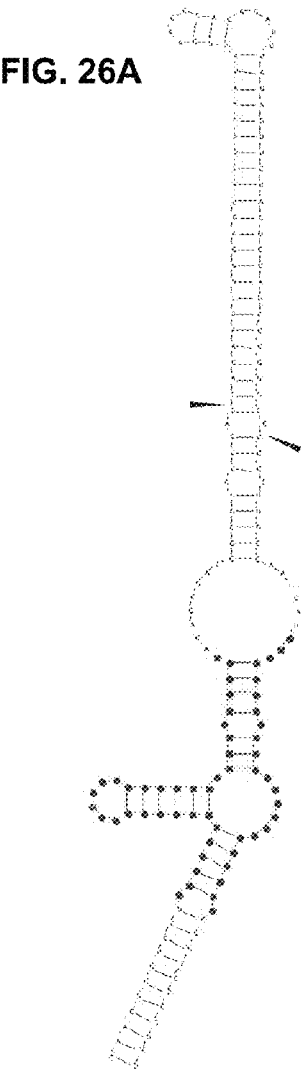
FIG. 26A-26C. Folinic acid-responsive miRNAs.
Figure 26B:
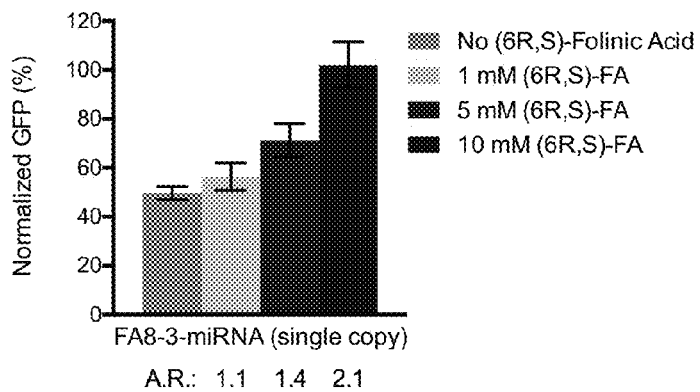

Isolated cells were screened for switching activity, sequenced, and re-cloned from synthesized oligonucleotides into a fresh plasmid backbone for characterization. Interestingly, only a single switch, FA-22, with an aptamer replacing loop II of the ribozyme was identified. This lack of functional solutions with aptamers replacing loop II could reflect fewer natural examples of hammerhead ribozymes with a larger loop II relative to loop I. In addition, aptamer integration within loop I may be kinetically favored, as the aptamer would be fully transcribed before the ribozyme, providing more time for ligand binding before ribozyme cleavage. As the sorts were designed to isolated functional switches and not solely functional ribozymes, it is possible that aptamer integration in loop II could produce active ribozymes but were unfavorable switches compared to loop I integration. Three other families of switches were identified (FIG. 26). The highest performing switches demonstrated up to 25.2-fold activation ratios (ratio of GFP expression in the presence of ligand to expression in the absence of ligand) in the presence of 3 mM (6R)-folinic acid and dynamic ranges of up to 43.6% (difference between GFP expression in the presence and absence of ligand).

More switches incorporating aptamer FA8-11 were isolated. One hypothesis is that aptamer FA8-11 may facilitate greater conformational changes upon ligand binding. The required U-G base pair in this aptamer is necessary for ligand binding; these two nucleotides are also present in aptamer FA8-4 but not contained within a base stem. This base pair, while base paired in the absence of ligand, may open up and form contacts with the ligand upon binding. If true, ligand binding would not only cause local conformation changes within the aptamer but would also disrupt a base pair in a stem of the ribozyme, further impairing tertiary interactions between the two ribozyme loops. This hypothesis can be tested using chemical probing techniques such as SHAPE to assess changes in RNA structure in the absence and presence of folinic acid.

Example 5

Rational Design of microRNA-Based Switches in Mammalian Cells

Ligand-responsive, microRNA (miRNA) switches have been developed that modulate Drosha processing. These switches integrate an aptamer into the basal segments of a miRNA. Internal loop size contained within the basal segments affects Drosha processing and therefore the levels of miRNA-mediated gene silencing. By integrating an aptamer within the basal segments, unbound aptamer can remain relatively unstructured, while ligand binding can sequester nucleotides involved in binding and inhibit Drosha processing.

Figure 26C:
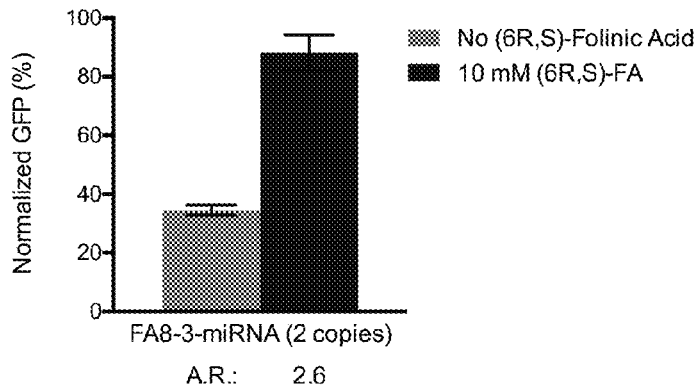

Aptamer integration into this switch platform requires two integration stems; therefore, aptamer FA8-3 was chosen. Separate studies on using this aptamer in a transmitter-based switch observe that an internal loop within the aptamer could be expanded while retaining ligand binding ability. This loop was expanded to the previously identified optimal loop size and integrated into the miRNA switch that targets GFP. A single copy of the miRNA switch enables up to 2.1-fold change in GFP expression (FIG. 26b); including two copies yields up to 2.6-fold change (FIG. 26c). Additional copies of the switch would be expected to further increase the achievable activation ratio, as would specific use of (6R)-folinic acid.

TABLE 7

Sequences for rationally designed and miRNA-based folinic acid-responsive switches and for device libraries based on ribozyme loop replacement strategy and isolated folinic acid-responsive switches.

| Rationally designed switches | DNA sequence |
| --- | --- |
| FA8-4-switch4<br>SEQ ID NO: 52 | 5'-<br>AAACAAACAAAGCTGTCACCGGATGTGCTTTCCGGTCTGATGAGTCCGTTGCTGGCGTT<br>GCGTGGTACGTTATATTCCGGCCAGTTCAGCGGAGGACGAAACAGCAAAAAGAAAAATA<br>AAAA |
| FA8-3-switch9<br>SEQ ID NO: 53 | 5'-<br>AAACAAACAAATTTGCCAACGTCTGGTCACGACCGCTGTCACCGGATGTGCTTTCCGGT<br>CTGATGAGTCCGTGAGGACGAAACAGCACAGCCCCTCGAAATCACGAGGGAGACGAGAT<br>AGGCGGAAAAAAGAAAATAAAAA |
| 8-3-switch1<br>SEQ ID NO: 54 | 5'-<br>AAACAAACAAAGCTGTCACCGGATGTGCTTTCCGGTCTGATGAGTCCGTTGTCCCAACG<br>TCTGGTCACGACCGTAGTACACTACCCCTCGAAATCACGAGGGAGACGAGATAGGGACG<br>GGACGGAGGACGAAACAGCAAAAAGAAAATAAAAA |
| 8-3-switch3<br>SEQ ID NO: 55 | 5'-<br>AAACAAACAAAGCTGTCACCGGATGTGCTTTCCGGTCTGATGAGTCCGTTGAGTCAACG<br>TCTGGTCACGACCGTAGTACACTACCCCTCGAAATCACGAGGGAGACGAGATAGACTGA<br>TTACGGAGGACGAAACAGCAAAAAGAAAATAAAAA |
| 8-3-switch4<br>SEQ ID NO: 56 | 5'-<br>AAACAAACAAAGCTGTCACCGGATGTGCTTTCCGGTCTGATGAGTCCGTTGCTGCAACG<br>TCTGGTCACGACCGTAGTACACTACCCCTCGAAATCACGAGGGAGACGAGATAGCAGTT<br>CAGCGGAGGACGAAACAGCAAAAAGAAAATAAAAA |
| miRNA-based switches | DNA sequence |
| FA8-3-miRNA<br>SEQ ID NO: 57 | 5'-<br>AATAACCGGTGCGATCGCGAACGGGTCCTCACTACCCCTCGAAATCACGAGGGAGACGA<br>GATAAGAGCGACGGCGGAGCGAGCACAAGCTGGAGTACAACTATAGTGAAGCCACAGAT<br>GTATAGTTGTACTCCAGCTTGTGCCCGCCTTGCCAACCATAACGTCTGGTCACGACCGT<br>AGTAAGGGCCCGTTTTTAATTAAATCGATTATT |
| Device libraries | Sequence |
| 6bpL1N6/4bpL2FA8-4<br>SEQ ID NO: 58 | CCTAGGAAACAAACAAAGCTGTCACCGGANNNNNNTCCGGTCTGATGAGTC<br>CGNTGCGTGGTACGTTATATTCCGGGACGAAACAGCAAAAAGAAAATAAA<br>AACTCGAG |
| 6bpL1N7/4bpL2FA8-4<br>SEQ ID NO: 59 | CCTAGGAAACAAACAAAGCTGTCACCGGANNNNNNNTCCGGTCTGATGAGT<br>CCGNTGCGTGGTACGTTATATTCCGGGACGAAACAGCAAAAAGAAAATAA<br>AAACTCGAG |
| 6bpL1FA8-4/3bpL2N6<br>SEQ ID NO: 60 | CCTAGGAAACAAACAAAGCTGTCACCGGAGNTGCGTGGTACGTTATATTCC<br>GTCCGGTCTGATGAGTCNNNNNNGACGAAACAGCAAAAAGAAAATAAAAA<br>CTCGAG |
| 6bpL1FA8-4/3bpL2N7<br>SEQ ID NO: 61 | CCTAGGAAACAAACAAAGCTGTCACCGGAGNTGCGTGGTACGTTATATTCC<br>GTCCGGTCTGATGAGTCNNNNNNNGACGAAACAGCAAAAAGAAAATAAAA<br>ACTCGAG |
| 6bpL1FA8-4/4bpL2N6<br>SEQ ID NO: 62 | CCTAGGAAACAAACAAAGCTGTCACCGGAGNTGCGTGGTACGTTATATTCC<br>GTCCGGTCTGATGAGTCCNNNNNNGGACGAAACAGCAAAAAGAAAATAAA<br>AACTCGAG |
| 6bpL1N6/4bpL2FA8-11<br>SEQ ID NO: 63 | CCTAGGAAACAAACAAAGCTGTCACCGGANNNNNNTCCGGTCTGATGAGTC<br>TGCNTGGTACGTTATATTCRGGACGAAACAGCAAAAAGAAAATAAAAACT<br>CGAG |
| 6bpL1N7/4bpL2FA8-11<br>SEQ ID NO: 64 | CCTAGGAAACAAACAAAGCTGTCACCGGANNNNNNNTCCGGTCTGATGAGT<br>CTGCNTGGTACGTTATATTCRGGACGAAACAGCAAAAAGAAAATAAAAAC<br>TCGAG |
| 6bpL1FA8-11/3bpL2N6<br>SEQ ID NO: 65 | CCTAGGAAACAAACAAAGCTGTCACCGGTGCNTGGTACGTTATATTCRGCC<br>GGTCTGATGAGTCNNNNNNGACGAAACAGCAAAAAGAAAATAAAAACTCG<br>AG |
| 6bpL1FA8-11/3bpL2N7<br>SEQ ID NO: 66 | CCTAGGAAACAAACAAAGCTGTCACCGGTGCNTGGTACGTTATATTCRGCC<br>GGTCTGATGAGTCNNNNNNNGACGAAACAGCAAAAAGAAAATAAAAACTC<br>GAG |

TABLE 7-continued

Sequences for rationally designed and miRNA-based folinic acid-responsive switches and for device libraries based on ribozyme loop replacement strategy and isolated folinic acid-responsive switches.

| | |
|---|---|
| 6bpL1FA8-11/4bpL2N6<br>SEQ ID NO: 67 | CCTAGGAAACAAACAAAGCTGTCACCGGTGCNTGGTACGTTATATTCRGCC<br>GGTCTGATGAGTCCNNNNNNGGACGAAACAGCAAAAAGAAAAATAAAAACT<br>CGAG |
| 5bpL1FA8-4/3bpL2N7<br>SEQ ID NO: 68 | CCTAGGAAACAAACAAAGCTGTCACCGGGNTGCGTGGTACGTTATATTCCG<br>CCGGTCTGATGAGTCNNNNNNNGACGAAACAGCAAAAAGAAAAATAAAAAC<br>TCGAG |
| 3bpL1N7/5bpL2FA8-4<br>SEQ ID NO: 69 | CCTAGGAAACAAACAAAGCTGTCACCNNNNNNNGGTCTGATGAGTCCCGNT<br>GCGTGGTACGTTATATTCCGGGGACGAAACAGCAAAAAGAAAAATAAAAAC<br>TCGAG |
| 5bpL1FA8-11/3bpL2N7<br>SEQ ID NO: 70 | CCTAGGAAACAAACAAAGCTGTCACCGTGCNTGGTACGTTATATTCRGCGG<br>TCTGATGAGTCNNNNNNNGACGAAACAGCAAAAAGAAAAATAAAAACTCGA<br>G |
| 3bpL1N7/5bpFA8-11<br>SEQ ID NO: 71 | cCTAGGAAACAAACAAAGCTGTCACCNNNNNNNGGTCTGATGAGTCCTGCN<br>TGGTACGTTATATTCRGGGACGAAACAGCAAAAAGAAAAATAAAAACTCGA<br>G |

| Loop replacement switch | Sequence |
|---|---|
| FA-4<br>SEQ ID NO: 72 | AAACAAACAAAGCTGTCACCGGTGCATGGTACGTTATATTCAGCCGGTCTG<br>ATGAGTCCTGGGGGACGAAACAGCAAAAAGAAAAATAAAAA |
| FA-6<br>SEQ ID NO: 73 | AAACAAACAAAGCTGTCACCGGTGCTTGGTACGTTATATTCAGCCGGTCTG<br>ATGAGTCTTGAGGAGACGAAACAGCAAAAAGAAAAATAAAAA |
| FA-7<br>SEQ ID NO: 74 | AAACAAACAAAGCTGTCACCGGTGCTTGGTACGTTATATTCAGCCGGTCTG<br>ATGAGTCCACAGAGGGACGAAACAGCAAAAAGAAAAATAAAAA |
| FA-9<br>SEQ ID NO: 75 | AAACAAACAAAGCTGTCACCGGAGATGCGTGGTACGTTATATTCCGTCCGG<br>TCTGATGAGTCCAGAGGGACGAAACAGCAAAAAGAAAAATAAAAA |
| FA-11<br>SEQ ID NO: 76 | AAACAAACAAAGCTGTCACCGGTGCTTGGTACGTTATATTCAGCCGGTCTG<br>ATGAGTCTTGGAGAGACGAAACAGCAAAAAGAAAAATAAAAA |
| FA-12<br>SEQ ID NO: 77 | AAACAAACAAAGCTGTCACCGGAGTTGCGTGGTACGTTATATTCCGTCCGG<br>TCTGATGAGTCCAAAGGGGACGAAACAGCAAAAAGAAAAATAAAAA |
| FA-14<br>SEQ ID NO: 78 | AAACAAACAAAGCTGTCACCGGTGCTTGGTACGTTATATTCAGCCGGTCTG<br>ATGAGTCTTGAAGAGACGAAACAGCAAAAAGAAAAATAAAAA |
| FA-18<br>SEQ ID NO: 79 | AAACAAACAAAGCTGTCACCGGTGCTTGGTACGTTATATTCAGCCGGTCTG<br>ATGAGTCTTCAAGAGACGAAACAGCAAAAAGAAAAATAAAAA |
| FA-19<br>SEQ ID NO: 8- | AAACAAACAAAGCTGTCACCGGTGCTTGGTACGTTATATTCAGCCGGTCTG<br>ATGAGTCCAAAGGGGACGAAACAGCAAAAAGAAAAATAAAAA |
| FA-22<br>SEQ ID NO: 81 | AAACAAACAAAGCTGTCACCGGAGGTGTAGTCCGGTCTGATGAGTCCGTTG<br>CGTGGTACGTTATATTCCGGGACGAAACAGCAAAAAGAAAAATAAAAA |
| FA-27<br>SEQ ID NO: 82 | AAACAAACAAAGCTGTCACCGGTGCTTGGTACGTTATATTCAGCCGGTCTG<br>ATGAGTCCTGGAGGGACGAAACAGCAAAAAGAAAAATAAAAA |
| FA-32<br>SEQ ID NO: 83 | AAACAAACAAAGCTGTCACCGGAGTTGCGTGGTACGTTATATTCCGTCCGG<br>TCTGATGAGTCTAGAAGAGACGAAACAGCAAAAAGAAAAATAAAAA |
| FA-34<br>SEQ ID NO: 84 | AAACAAACAAAGCTGTCACCGGTGCTTGGTACGTTATATTCAGCCGGTCTG<br>ATGAGTCTTAAAGAGACGAAACAGCAAAAAGAAAAATAAAAA |
| FA-58<br>SEQ ID NO: 85 | AAACAAACAAAGCTGTCACCGGTGCTTGGTACGTTATATTCAGCCGGTCTG<br>ATGAGTCCATAGAGGGACGAAACAGCAAAAAGAAAAATAAAAA |

| Ribozyme controls | Sequence |
|---|---|
| sTRSV ContI<br>SEQ ID NO: 86 | AAACAAACAAAGCTGTCACCGGATGTGCTTTCCGGTACGTGAGGTCCGTGA<br>GGACAGAACAGCAAAAAGAAAAATAAAAA |
| sTRSV<br>SEQ ID NO: 87 | AAACAAACAAAGCTGTCACCGGATGTGCTTTCCGGTCTGATGAGTCCGTGA<br>GGACGAAACAGCAAAAAGAAAAATAAAAA |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An aptamer that comprises a sequence having at least 70% identity sequence to FAt8-4 (SEQ ID NO:18), FAt8-11 (SEQ ID NO:20), FAt8-3 (SEQ ID NO:19), FAt6-8 (SEQ ID NO:21), or FAt8-16 (SEQ ID NO:22) and specifically binds to folinic acid, a folate, or a derivative thereof.

2. An aptamer that specifically binds (6R)-folinic acid and comprises a sequence having at least 70% identity sequence to FAt8-4 (SEQ ID NO:18), FAt8-11 (SEQ ID NO:20), FAt8-3 (SEQ ID NO:19), FAt6-8 (SEQ ID NO:21), or FAt8-16 (SEQ ID NO:22).

3. An aptamer, comprising a sequence selected from:
a minimally required sequence of FAt8-4 (i) $N_1$ $N_2$ G $N_3$ U G C G U G G U A C G U U A U A U U C C G $N_4$ $N_5$ (SEQ ID NO:129), where $N_1$ and $N_5$ are any complementary pair of nucleotides; $N_2$ and $N_4$ are any complementary pair of nucleotides; and $N_3$ is any nucleotide;
a minimally required sequence of FAt8-11 (ii) $N_1$ $N_2$ U G C $N_3$ U G G U A C G U U A U A U U C R G $N_4$ $N_5$ (SEQ ID NO:130), where $N_1$ and $N_5$ are any complementary pair of nucleotides; $N_2$ and $N_4$ are any complementary pair of nucleotides; $N_3$ is any nucleotide; and R is an A or G nucleotide;
a minimally required sequence of FAt8-3 (iii) C G U C U G G U C A C G A C C $N_1$ $N_2$-$N_3$ $N_4$ C C C U C G A A A U C A C G A G G G R G A C R A G A Y (SEQ ID NO:131), where $N_1$ and $N_4$ are any complementary pair of nucleotides; $N_2$ and $N_3$ are any complementary pair of nucleotides; R is an A or G nucleotide; Y is a C or U nucleotide; and the dash indicates any intervening sequence of nucleotides or two separate nucleotide strands.

4. The aptamer of claim 2, wherein the aptamer specifically binds to a ligand with a $K_D$ of up to 300 nM.

5. The aptamer of claim 2, operably linked to an actuator to generate an aptamer-regulated device.

6. The aptamer-regulated device of claim 5, wherein the actuator is a ribozyme.

7. The aptamer-regulated device of claim 6, wherein the ribozyme is a hammerhead ribozyme.

8. The aptamer-regulated device of claim 6 comprising a sequence set forth in any of SEQ ID NO:38-43.

9. The aptamer-regulated device of claim 5, wherein the actuator is selected from microRNAs, antisense RNAs, RNAi, CRISPR, splicing, small RNAs, ribosome binding sites, internal ribosome entry sites, aptamers, and any combination thereof.

10. An aptamer-regulated device, the device comprising an aptamer of claim 2, operably linked to an actuator, wherein the actuator is a hammerhead ribozyme and the aptamer and stem III of the hammerhead ribozyme comprise one or more shared base pairs.

11. The aptamer-regulated device of claim 10, wherein the aptamer-regulated device comprises a hammerhead ribozyme intervening sequence of nucleotides within the aptamer sequence.

12. A DNA sequence encoding an aptamer-regulated device according to claim 8.

13. An aptamer that comprises a sequence having at least 95% identity sequence to FAt8-4 (SEQ ID NO:18), FAt8-11 (SEQ ID NO:20), FAt8-3 (SEQ ID NO:19), FAt6-8 (SEQ ID NO:21), or FAt8-16 (SEQ ID NO:22) and specifically binds to folinic acid, a folate, or a derivative thereof.

* * * * *